(12) United States Patent
Sill et al.

(10) Patent No.: US 7,799,339 B2
(45) Date of Patent: Sep. 21, 2010

(54) HYBRID BLOCK COPOLYMER MICELLES WITH MIXED STEREOCHEMISTRY FOR ENCAPSULATION OF HYDROPHOBIC AGENTS

(75) Inventors: Kevin N. Sill, Tampa, FL (US); Habib Skaff, Tampa, FL (US); Kurt Breitenkamp, Tampa, FL (US)

(73) Assignee: Intezyne Technologies, Inc., Tampa, FL (US)

( * ) Notice: Subject to any disclaimer, the term of this patent is extended or adjusted under 35 U.S.C. 154(b) by 84 days.

(21) Appl. No.: 12/112,825

(22) Filed: Apr. 30, 2008

(65) Prior Publication Data

US 2008/0274173 A1 Nov. 6, 2008

Related U.S. Application Data

(60) Provisional application No. 60/914,958, filed on Apr. 30, 2007.

(51) Int. Cl.
*A61K 9/127* (2006.01)
(52) U.S. Cl. .................................. 424/450; 930/290
(58) Field of Classification Search ........................ None
See application file for complete search history.

(56) References Cited

U.S. PATENT DOCUMENTS

| | | | |
|---|---|---|---|
| 4,650,750 | A | 3/1987 | Giese |
| 4,709,016 | A | 11/1987 | Giese |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 2006/0142506 | A1 | 6/2006 | Breitenkamp et al. |
| 2006/0172914 | A1 | 8/2006 | Breitenkamp et al. |
| 2006/0240092 | A1* | 10/2006 | Breitenkamp et al. ....... 424/450 |
| 2008/0207913 | A1 | 8/2008 | Breitenkamp et al. |

FOREIGN PATENT DOCUMENTS

| WO | 2006047419 | 10/2004 |
|---|---|---|
| WO | 2006074202 | 7/2006 |

OTHER PUBLICATIONS

Ikeda, et al. "The Structure of Copolymers of L-Proline with gamma-Benzyl-L-Glutamate in Organic solvents," Bull. Chem. Soc. Japan 1969, 42, 1332-1336.
Paulillo, et al, "Nuclear Magnetic Resonance and Optical Spectroscopic Studies of Copolymers of Polypeptides. II. Randon Copoly(Benzyl-L-Glutamate: Benzyl-L-Aspartate) and (Benzyl-D-Glutamate: Benzyl-L-Aspartate)" Biopolymers 1972, 11, 2043-2052.
Cho, et al. "Synthesis and characterization of di- and triblock copolymers of poly(ethylene oxide) and poly (DL-valine-co-DL-leucine" Polymer 2003, 44, 5497-5500.
Bakar, et al. "The chemical speciation of zinc in human saliva: possible correlation with reduction of the symptoms of the common cold produced by zinc gluconate-containing lozenges" Chem. Spec. Bioavail. 1999, 11, 95-101.
Eby, "Zinc ion availability—the determinant of efficacy in zinc lozenge treatment of common colds" J. Antimicrob. Chemo. 1997, 40, 483-493.
Tezcan, et al, "Controlling Protein—Protein Interactions through Metal Coordination: Assembly of a 16-Helix Bundle Protein"J. Am. Chem. Soc. 2007, 129, 13374-13375.
Kibrick, et al., "Complex Formation between Carboxylic Acids and Divalent Metal Cations" J. Am. Chem. Soc. 1938, 60, 2314-2320.
Wooley, et al., "Folic acid-conjugated nanostructured materials designed for cancer cell targeting" Chem. Commun. 2003, 2400-2401.
Gabizon, "Tumor cell targeting of liposome-entrapped drugs with phospholipid-anchored folic acid-PEG conjugates" Advanced Drug Deliver Reviews 2004, 56, 1177-1202.
Curiel, "Insertion of an RGD motif into the HI loop of adenovirus fiber protein alters the distribution of transgene expression of the systemically administered vector" Gene Ther. 1999, 6, 1336-1339.
De Witte, "Transferrin-conjugated liposome targeting of photosensitizer AIPcS4 to rat bladder carcinoma cells" J. Nat. Cancer Inst. 2004, 96, 1620-30.
Gao, "cRGD-functionalized polymer micelles for targeted doxorubicin delivery" Angew. Chem. Int. Ed. 2004, 43, 6323-6327.
Kataoka, et al., "Lactose-installed poly(ethylene glycol)-poly(D,L-lactide) block copolymer micelles exhibit fast-rate binding and high affinity toward a protein bed simulating a cell surface. A surface plasmon resonance study" Bioconj. Chem. 2003, 14, 177-186.
Lilie, et al, "Conjugation of an antibody Fv fragment to a virus coat protein: cell-specific targeting of recombinant polyoma-virus-like particles" Biochem. J. 2001, 356, 867-873.
Kurschus, "Killing of target cells by redirected granzyme B in the absence of perforin" FEBS Lett. 2004, 562, 87-92.
Jones, et al., "Antibodies for targeted gene therapy: extracellular gene targeting and intracellular expression" Adv. Drug Del. Rev. 1998, 31, 153-170.
Sharpless, et al., "Click chemistry: Diverse chemical function from a few good reactions" Angew. Chem. Int. Ed. 2001, 40, 2004-2021.
Finn, et al., "Bioconjugation by copper(I)-catalyzed azide-alkyne [3+2] cycloaddition" J. Am. Chem. Soc. 2003, 125, 3192-3193.
Tirrell, et al., "Presentation and detection of azide functionality in bacterial cell surface proteins" J. Am. Chem. Soc. 2004, 126, 10598-10602.
Schultz, et al., "Adding amino acids with novel reactivity to the genetic code of *Saccharomyces cerevisiae*" J. Am. Chem. Soc. 2003, 125, 11782-11783.
Eisenberg et al., "Nano-engineering block copolymer aggregates for drug delivery" Colloid Surface B 1999, 16, 3-27.

\* cited by examiner

*Primary Examiner*—Frederick Krass
*Assistant Examiner*—Isaac Shomer
(74) *Attorney, Agent, or Firm*—Choate Hall & Stewart LLP; Andrea L. C. Robidoux

(57) ABSTRACT

The present invention relates to the field of polymer chemistry and more particularly to multiblock copolymers and micelles comprising the same.

1 Claim, 13 Drawing Sheets

HYBRID BLOCK COPOLYMER MICELLES WITH MIXED STEREOCHEMISTRY FOR ENCAPSULATION OF HYDROPHOBIC AGENTS

CROSS-REFERENCE TO RELATED APPLICATIONS

The present application claims priority to U.S. provisional patent application Ser. No. 60/914,958, filed Apr. 30, 2007, the entirety of which is hereby incorporated herein by reference.

FIELD OF THE INVENTION

The present invention relates to the field of polymer chemistry and more particularly to multiblock copolymers and uses thereof.

BACKGROUND OF THE INVENTION

The development of new therapeutic agents has dramatically improved the quality of life and survival rate of patients suffering from a variety of disorders. However, drug delivery innovations are needed to improve the success rate of these treatments. Specifically, delivery systems are still needed which effectively minimize premature excretion and/or metabolism of therapeutic agents and deliver these agents specifically to diseased cells thereby reducing their toxicity to healthy cells.

Rationally-designed, nanoscopic drug carriers, or "nanovectors," offer a promising approach to achieving these goals due to their inherent ability to overcome many biological barriers. Moreover, their multi-functionality permits the incorporation of cell-targeting groups, diagnostic agents, and a multitude of drugs in a single delivery system. Polymer micelles, formed by the molecular assembly of functional, amphiphilic block copolymers, represent one notable type of multifunctional nanovector.

Polymer micelles are particularly attractive due to their ability to deliver large payloads of a variety of drugs (e.g. small molecule, proteins, and DNA/RNA therapeutics), their improved in vivo stability as compared to other colloidal carriers (e.g. liposomes), and their nanoscopic size which allows for passive accumulation in diseased tissues, such as solid tumors, by the enhanced permeation and retention (EPR) effect. Using appropriate surface functionality, polymer micelles are further decorated with cell-targeting groups and permeation enhancers that can actively target diseased cells and aid in cellular entry, resulting in improved cell-specific delivery.

While self assembly represents a convenient method for the bottom-up design of nanovectors, the forces that drive and sustain the assembly of polymer micelles are concentration dependent and inherently reversible. In clinical applications, where polymer micelles are rapidly diluted following administration, this reversibility, along with high concentrations of micelle-destabilizing blood components (e.g. proteins, lipids, and phospholipids), often leads to premature dissociation of the drug-loaded micelle before active or passive targeting is effectively achieved. For polymer micelles to fully reach their cell-targeting potential and exploit their envisioned multi-functionality, in vivo circulation time must be improved. Drug delivery vehicles are needed, which are infinitely stable to post-administration dilution, can avoid biological barriers (e.g. reticuloendothelial system (RES) uptake), and deliver drugs in response to the physiological environment encountered in diseased tissues, such as solid tumors.

DETAILED DESCRIPTION OF CERTAIN EMBODIMENTS OF THE INVENTION

1. General Description

Figure 1:
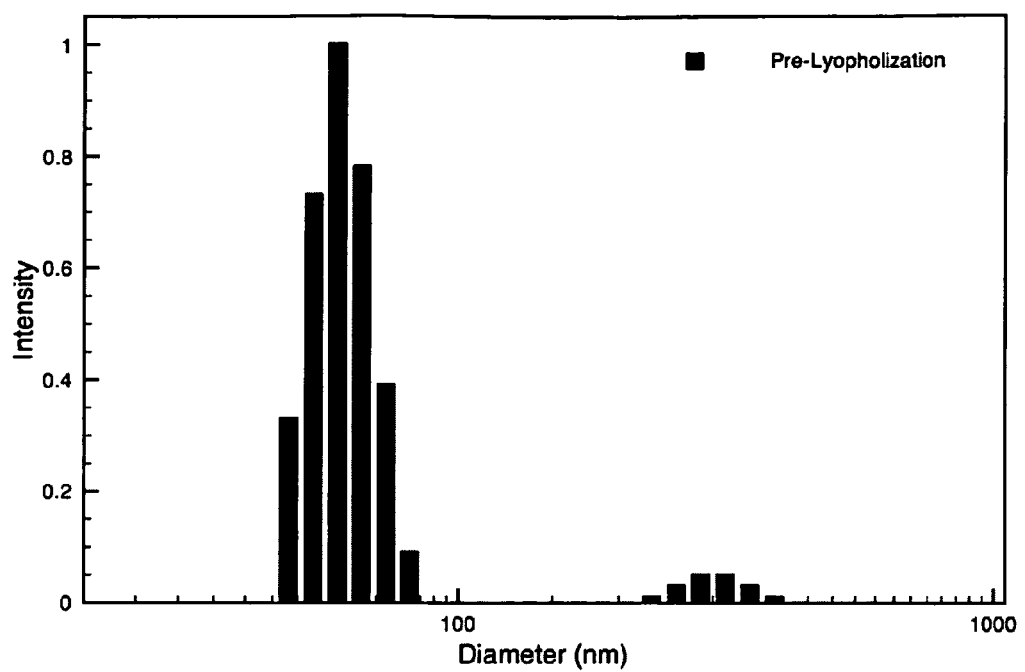
FIG. 1 depicts the results of dynamic light scattering of $Fe_2O_3$ encapsulated micelles.

According to one embodiment, the present invention provides a micelle comprising a multiblock copolymer which comprises a polymeric hydrophilic block, optionally a crosslinkable or crosslinked poly(amino acid block), and a hydrophobic D,L-mixed poly(amino acid) block, characterized in that said micelle has an inner core, optionally a crosslinkable or crosslinked outer core, and a hydrophilic shell. It will be appreciated that the polymeric hydrophilic block corresponds to the hydrophilic shell, the optionally crosslinkable or crosslinked poly(amino acid block) corresponds to the optionally crosslinked outer core, and the hydrophobic D,L-mixed poly(amino acid) block corresponds to the inner core.

The "hydrophobic D,L-mixed poly(amino acid)" block, as described herein, consists of a mixture of D and L enantiomers to facilitate the encapsulation of hydrophobic moieties. It is well established that homopolymers and copolymers of amino acids, consisting of a single stereoisomer, may exhibit secondary structures such as the α-helix or β-sheet. See *α-Aminoacid-N-Caroboxy-Anhydrides and Related Hetero-*

*cycles*, H. R. Kricheldorf, Springer-Verlag, 1987. For example, poly(L-benzyl glutatmate) typically exhibits an α-helical conformation; however this secondary structure can be disrupted by a change of solvent or temperature (see *Advances in Protein Chemistry XVI*, P. Urnes and P. Doty, Academic Press, New York 1961). The secondary structure can also be disrupted by the incorporation of structurally dissimilar amino acids such as β-sheet forming amino acids (e.g. proline) or through the incorporation of amino acids with dissimilar stereochemistry (e.g. mixture of D and L stereoisomers), which results in poly(amino acids) with a random coil conformation. See Sakai, R.; Ikeda; S.; Isemura, T. *Bull Chem. Soc. Japan* 1969, 42, 1332-1336, Paolillo, L.; Temussi, P. A.; Bradbury, E. M.; Crane-Robinson, C. *Biopolymers* 1972, 11, 2043-2052, and Cho, I.; Kim, J. B.; Jung, H. J. *Polymer* 2003, 44, 5497-5500.

While the methods to influence secondary structure of poly(amino acids) have been known for some time, it has been suprisingly discovered that block copolymers possessing a random coil conformation are particularly useful for the encapsulation of hydrophobic molecules and nanoparticles when compared to similar block copolymers possessing a helical segment. Without wishing to be bound to any particular theory, it is believed that provided block copolymers having a coil-coil conformation allow for efficient packing and loading of hydrophobic moieties within the micelle core, while the steric demands of a rod-coil conformation for a helix-containing block copolymer results in less effective encapsulation.

2. Definitions

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As used herein, the term "sequential polymerization", and variations thereof, refers to the method wherein, after a first monomer (e.g. NCA, lactam, or imide) is incorporated into the polymer, thus forming an amino acid "block", a second monomer (e.g. NCA, lactam, or imide) is added to the reaction to form a second amino acid block, which process may be continued in a similar fashion to introduce additional amino acid blocks into the resulting multi-block copolymers.

As used herein, the term "multiblock copolymer" refers to a polymer comprising one synthetic polymer portion and two or more poly(amino acid) portions. Such multi-block copolymers include those having the format W—X'—X", wherein W is a synthetic polymer portion and X and X' are poly(amino acid) chains or "amino acid blocks". In certain embodiments, the multiblock copolymers of the present invention are triblock copolymers. As described herein, one or more of the amino acid blocks may be "mixed blocks", meaning that these blocks can contain a mixture of amino acid monomers thereby creating multiblock copolymers of the present invention. In some embodiments, the multiblock copolymers of the present invention comprise a mixed amino acid block and are tetrablock copolymers.

As used herein, the term "triblock copolymer" refers to a polymer comprising one synthetic polymer portion and two poly(amino acid) portions.

As used herein, the term "tetrablock copolymer" refers to a polymer comprising one synthetic polymer portion and either two poly(amino acid) portions, wherein 1 poly(amino acid) portion is a mixed block or a polymer comprising one synthetic polymer portion and three poly(amino acid) portions.

As used herein, the term "inner core" as it applies to a micelle of the present invention refers to the center of the micelle formed by the hydrophobic D,L-mixed poly(amino acid) block. In accordance with the present invention, the inner core is not crosslinked. By way of illustration, in a triblock polymer of the format W—X'—X", as described above, the inner core corresponds to the X" block.

As used herein, the term "outer core" as it applies to a micelle of the present invention refers to the layer formed by the first poly(amino acid) block. The outer core lies between the inner core and the hydrophilic shell. In accordance with the present invention, the outer core is either crosslinkable or is cross-linked. By way of illustration, in a triblock polymer of the format W—X'—X", as described above, the outer core corresponds to the X' block. It is contemplated that the X' block can be a mixed block.

As used herein, the terms "drug-loaded" and "encapsulated", and derivatives thereof, are used interchangeably. In accordance with the present invention, a "drug-loaded" micelle refers to a micelle having a drug, or therapeutic agent, situated within the core of the micelle. This is also referred to as a drug, or therapeutic agent, being "encapsulated" within the micelle.

As used herein, the term "polymeric hydrophilic block" refers to a polymer that is not a poly(amino acid) and is hydrophilic in nature. Such hydrophilic polymers are well known in the art and include polyethyleneoxide (also referred to as polyethylene glycol or PEG), and derivatives thereof, poly(N-vinyl-2-pyrolidone), and derivatives thereof, poly(N-isopropylacrylamide), and derivatives thereof, poly(hydroxyethyl acrylate), and derivatives thereof, poly(hydroxylethyl methacrylate), and derivatives thereof, and polymers of N-(2-hydroxypropoyl)methacrylamide (HMPA) and derivatives thereof.

As used herein, the term "poly(amino acid)" or "amino acid block" refers to a covalently linked amino acid chain wherein each monomer is an amino acid unit. Such amino acid units include natural and unnatural amino acids. In certain embodiments, each amino acid unit of the optionally a crosslinkable or crosslinked poly(amino acid block)is in the L-configuration. Such poly(amino acids) include those having suitably protected functional groups. For example, amino acid monomers may have hydroxyl or amino moieties which are optionally protected by a suitable hydroxyl protecting group or a suitable amine protecting group, as appropriate. Such suitable hydroxyl protecting groups and suitable amine protecting groups are described in more detail herein, infra. As used herein, an amino acid block comprises one or more monomers or a set of two or more monomers. In certain embodiments, an amino acid block comprises one or more monomers such that the overall block is hydrophilic. In still other embodiments, amino acid blocks of the present invention include random amino acid blocks, ie blocks comprising a mixture of amino acid residues.

As used herein, the term "D,L-mixed poly(amino acid) block" refers to a poly(amino acid) block wherein the poly (amino acid) consists of a mixture of amino acids in both the D- and L-configurations. In certain embodiments, the D,L-mixed poly(amino acid) block is hydrophobic. In other embodiments, the D,L-mixed poly(amino acid) block consists of a mixture of D-configured hydrophobic amino acids and L-configured hydrophilic amino acid side-chain groups such that the overall poly(amino acid) block comprising is hydrophobic.

Exemplary poly(amino acids) include poly(benzyl glutamate), poly(benzyl aspartate), poly(L-leucine-co-tyrosine), poly(D-leucine-co-tyrosine), poly(L-phenylalanine-co-tyrosine), poly(D-phenylalanine-co-tyrosine), poly(L-leucine-coaspartic acid), poly(D-leucine-co-aspartic acid), poly(L-phenylalanine-co-aspartic acid), poly(D-phenylalanine-co-aspartic acid), poly(L-benzyl aspartate-co-aspartic acid), poly(D-benzyl aspartate-co-aspartic acid), poly(L-benzyl aspartate-co-tyrosine), poly(D-benzyl aspartate-co-tyrosine).

As used herein, the phrase "natural amino acid side-chain group" refers to the side-chain group of any of the 20 amino acids naturally occurring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group.

As used herein, the phrase "unnatural amino acid side-chain group" refers to amino acids not included in the list of 20 amino acids naturally occurring in proteins, as described above. Such amino acids include the D-isomer of any of the 20 naturally occurring amino acids. Unnatural amino acids also include homoserine, DOPA (also referred to as levodopa or 3,4-dihydroxy phenyl alanine), ornithine, and thyroxine. Other unnatural amino acids side-chains are well know to one of ordinary skill in the art and include unnatural aliphatic side chains. Other unnatural amino acids include modified amino acids, including those that are N-alkylated, cyclized, phosphorylated, acetylated, amidated, azidylated, labelled, and the like.

As used herein, the term "tacticity" refers to the stereochemistry of the poly(amino acid) hydrophobic block. A poly(amino acid) block consisting of a single stereoisomer (e.g. all L isomer) is referred to as "isotactic". A poly(amino acid) consisting of a random incorporation of D and L amino acid monomers is referred to as an "atactic" polymer. A poly(amino acid) with alternating stereochemistry (e.g. . . . DLDLDL . . . ) is referred to as a "syndiotactic" polymer. Polymer tacticity is described in more detail in "Principles of Polymerization", 3rd Ed., G. Odian, John Wiley & Sons, New York: 1991, the entire contents of which are hereby incorporated by reference.

As used herein, the phrase "living polymer chain-end" refers to the terminus resulting from a polymerization reaction which maintains the ability to react further with additional monomer or with a polymerization terminator.

As used herein, the term "termination" refers to attaching a terminal group to a polymer chain-end by the reaction of a living polymer with an appropriate compound. Alternatively, the term "termination" may refer to attaching a terminal group to an amine or hydroxyl end, or derivative thereof, of the polymer chain.

As used herein, the term "polymerization terminator" is used interchangeably with the term "polymerization terminating agent" and refers to a compound that reacts with a living polymer chain-end to afford a polymer with a terminal group. Alternatively, the term "polymerization terminator" may refer to a compound that reacts with an amine or hydroxyl end, or derivative thereof, of the polymer chain, to afford a polymer with a terminal group.

As used herein, the term "polymerization initiator" refers to a compound, which reacts with, or whose anion or free base form reacts with, the desired monomer in a manner which results in polymerization of that monomer. In certain embodiments, the polymerization initiator is the compound that reacts with an alkylene oxide to afford a polyalkylene oxide block. In other embodiments, the polymerization initiator is an amine salt as described herein. In certain embodiments, the polymerization initiator is a trifluoroacetic acid amine salt.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R$^+$)— as in N— substituted pyrrolidinyl.

The term "unsaturated", as used herein, means that a moiety has one or more units of unsaturation.

As used herein, the term "bivalent, saturated or unsaturated, straight or branched $C_{1-12}$ hydrocarbon chain", refers to bivalent alkylene, alkenylene, and alkynylene chains that are straight or branched as defined herein.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(CR*$_2$)$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A suitable tetravalent substituent that is bound to vicinal substitutable methylene carbons of an "optionally substituted" group is the dicobalt hexacarbonyl cluster represented by

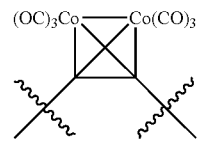

when depicted with the methylenes which bear it.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, propionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy) methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, 0-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable monoprotected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

A "crown ether moiety" is the radical of a crown ether. A crown ether is a monocyclic polyether comprised of repeating units of —$CH_2CH_2O$—. Examples of crown ethers include 12-crown-4, 15-crown-5, and 18-crown-6.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as in neutron scattering experiments, as analytical tools or probes in biological assays.

As used herein, the term "detectable moiety" is used interchangeably with the term "label" and relates to any moiety capable of being detected (e.g., primary labels and secondary labels). A "detectable moiety" or "label" is the radical of a detectable compound.

"Primary" labels include radioisotope-containing moieties (e.g., moieties that contain $^{32}P$, $^{33}P$, $^{35}S$, or $^{14}C$), mass-tags, and fluorescent labels, and are signal-generating reporter groups which can be detected without further modifications.

Other primary labels include those useful for positron emission tomography including molecules containing radioisotopes (e.g. $^{18}F$) or ligands with bound radioactive metals (e.g. $^{62}Cu$). In other embodiments, primary labels are contrast agents for magnetic resonance imaging such as gadolinium, gadolinium chelates, or iron oxide (e.g $Fe_3O_4$ and $Fe_2O_3$) particles. Similarly, semiconducting nanoparticles (e.g. cadmium selenide, cadmium sulfide, cadmium telluride) are useful as fluorescent labels. Other metal nanoparticles (e.g colloidal gold) also serve as primary labels.

"Secondary" labels include moieties such as biotin, or protein antigens, that require the presence of a second compound to produce a detectable signal. For example, in the case of a biotin label, the second compound may include streptavidin-enzyme conjugates. In the case of an antigen label, the second compound may include an antibody-enzyme conjugate. Additionally, certain fluorescent groups can act as secondary labels by transferring energy to another compound or group in a process of nonradiative fluorescent resonance energy transfer (FRET), causing the second compound or group to then generate the signal that is detected.

Unless otherwise indicated, radioisotope-containing moieties are optionally substituted hydrocarbon groups that contain at least one radioisotope. Unless otherwise indicated, radioisotope-containing moieties contain from 1-40 carbon atoms and one radioisotope. In certain embodiments, radioisotope-containing moieties contain from 1-20 carbon atoms and one radioisotope.

The terms "fluorescent label", "fluorescent group", "fluorescent compound", "fluorescent dye", and "fluorophore", as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethylrhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The term "substrate", as used herein, refers to any material or macromolecular complex to which a functionalized end-group of a block copolymer can be attached. Examples of commonly used substrates include, but are not limited to, glass surfaces, silica surfaces, plastic surfaces, metal surfaces, surfaces containing a metalic or chemical coating, membranes (eg., nylon, polysulfone, silica), micro-beads (eg., latex, polystyrene, or other polymer), porous polymer matrices (eg., polyacrylamide gel, polysaccharide, polymethacrylate), macromolecular complexes (eg., protein, polysaccharide).

3. Description of Exemplary Embodiments

A. Multiblock Copolymers

As described generally above, one embodiment of the present invention provides a micelle comprising a multiblock copolymer which comprises a polymeric hydrophilic block, optionally a poly(amino acid block) that may be crosslinked, and a hydrophobic D,L-mixed poly(amino acid) block, characterized in that said micelle has an inner core, optionally a crosslinkable outer core, and a hydrophilic shell.

Amphiphilic multiblock copolymers, as described herein, can self-assemble in aqueous solution to form nano- and micron-sized structures. In water, these amphiphilic multiblock copolymers assemble by multi-molecular micellization when present in solution above the critical micelle concentration (CMC). Without wishing to be bound by any particular theory, it is believed that the hydrophobic poly(amino acid) portion or "block" of the copolymer collapses to form the micellar core, while the hydrophilic PEG block forms a peripheral corona and imparts water solubility. In certain embodiments, the multiblock copolymers in accordance with the present invention possess distinct hydrophobic and hydrophilic segments that form micelles. In addition, these multiblock polymers optionally comprise a poly(amino acid) block which contains functionality suitable for crosslinking. It will be appreciated that this functionality is found on the corresponding amino acid side-chain.

In certain embodiments, the PEG block possesses a molecular weight of approx. 10,000 Da (225 repeat units) and contains at least one terminal amine hydrochloride salt used to initiate the synthesis of poly(amino acid) multi-block copolymers. In other embodiments, the PEG block possesses a molecular weight of approx. 12,000 Da (270 repeat units) and contains at least one terminal amine difluoroacetic acid ("DFA") salt used to initiate the synthesis of poly(amino acid) multi-block copolymers. Without wishing to be bound by theory, it is believed that this particular PEG chain length imparts adequate water-solubility to the micelles and provides relatively long in vivo circulation times.

In certain embodiments, the present invention provides a micelle comprising a multiblock copolymer of formula I:

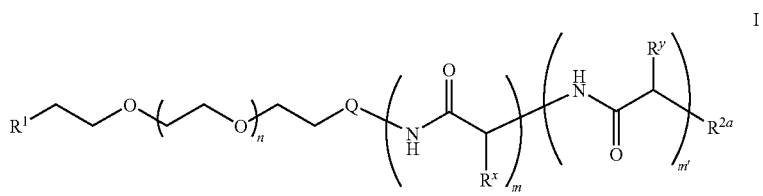

wherein:

n is 10-2500;

m is 0 to 1000;

m' is 2 to 1000;

$R^x$ is a natural or unnatural amino acid side-chain group that is capable of crosslinking;

$R^y$ forms a hydrophobic D,L-mixed poly(amino acid) block;

$R^1$ is —Z(CH$_2$CH$_2$Y)$_p$(CH$_2$)$_t$R$^3$, wherein:

Z is —O—, —S—, —C≡C—, or —CH$_2$—;

each Y is independently —O— or —S—;

p is 0-10;

t is 0-10; and $R^3$ is hydrogen, —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched C$_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and each $R^4$ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:

two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

According to another embodiment, the present invention provides compounds of formula I, as described above, wherein said compounds have a polydispersity index ("PDI") of about 1.0 to about 1.2. According to another embodiment, the present invention provides compounds of formula I, as described above, wherein said compound has a polydispersity index ("PDI") of about 1.03 to about 1.15. According to yet another embodiment, the present invention provides compounds of formula I, as described above, wherein said compound has a polydispersity index ("PDI") of about 1.10 to about 1.20. According to other embodiments, the present invention provides compounds of formula I having a PDI of less than about 1.10.

As defined generally above, the n group of formula I is 10-2500. In certain embodiments, the present invention provides compounds of formula I, as described above, wherein n is about 225. In other embodiments, n is about 270. In other embodiments, n is about 350. In other embodiments, n is about 10 to about 40. In other embodiments, n is about 40 to about 60. In other embodiments, n is about 60 to about 90. In still other embodiments, n is about 90 to about 150. In other embodiments, n is about 150 to about 200. In still other embodiments, n is about 200 to about 250. In other embodiments, n is about 300 to about 375. In other embodiments, n is about 400 to about 500. In still other embodiments, n is about 650 to about 750. In certain embodiments, n is selected from 50±10. In other embodiments, n is selected from 80±10, 115±10, 180±10, 225±10, 275±10, 315±10, or 340±10.

In certain embodiments, the m' group of formula I is about 5 to about 500. In certain embodiments, the m' group of formula I is about 10 to about 250. In other embodiments, m' is about 10 to about 50. According to yet another embodiment, m' is about 15 to about 40. In other embodiments, m' is about 20 to about 40. According to yet another embodiment, m' is about 50 to about 75. According to other embodiments, m and m' are independently about 10 to about 100.

In some embodiments, m is 0. In certain embodiments, m is 5-50. In other embodiments, m is 5-25. In certain embodiments, m' is 5-50. In certain embodiments, m' is 5-10. In other embodiments, m' is 10-20. In other embodiments, m and m' add up to about 30 to about 60. In still other embodiments, m is 1-20 repeat units and m' is 10-50 repeat units.

In certain embodiments, the $R^3$ moiety of the $R^1$ group of formula I is —N$_3$.

In other embodiments, the $R^3$ moiety of the $R^1$ group of formula I is —CN.

In some embodiments, the $R^3$ moiety of the $R^1$ group of formula I is hydrogen.

In still other embodiments, the $R^3$ moiety of the $R^1$ group of formula I is a mono-protected amine or a di-protected amine.

In certain embodiments, the $R^3$ moiety of the $R^1$ group of formula I is an optionally substituted aliphatic group. Examples include methyl, t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said $R^3$ moiety is an optionally substituted alkyl group. In other embodiments, said $R^3$ moiety is an optionally substituted alkynyl or alkenyl group. When said $R^3$ moiety is a substituted aliphatic group, suitable substituents on $R^3$ include CN, N$_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the $R^1$ group is 2-(N-methyl-N-(ethynylcarbonyl)amino)ethoxy, 4-ethynylbenzyloxy, or 2-(4-ethynylphenoxy)ethoxy.

In certain embodiments, the $R^3$ moiety of the $R^1$ group of formula I is an optionally substituted aryl group. Examples include optionally substituted phenyl and optionally substituted pyridyl. When said $R^3$ moiety is a substituted aryl group, suitable substituents on $R^3$ include CN, N$_3$, NO$_2$, —CH$_3$, —CH$_2$N$_3$, —CH═CH$_2$, —C≡CH, Br, I, F, bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, the R$^3$ moiety is an aryl group substituted with a suitably protected amino group. According to another aspect, the R$^3$ moiety is phenyl substituted with a suitably protected amino group.

In other embodiments, the R$^3$ moiety of the R$^1$ group of formula I is a protected hydroxyl group. In certain embodiments the protected hydroxyl of the R$^3$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ether, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the R$^3$ moiety of the R$^1$ group of formula I is a mono-protected or di-protected amino group. In certain embodiments R$^3$ is a mono-protected amine. In certain embodiments R$^3$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments R$^3$ is a di-protected amine. Exemplary di-protected amines include dibenzylamine, di-allylamine, phthalimide, maleimide, succinimide, pyrrole, 2,2,5,5-tetramethyl-[1,2,5]azadisilolidine, and azide. In certain embodiments, the R$^3$ moiety is phthalimido. In certain embodiments, the R$^3$ moiety is mono- or di-benzylamino or mono- or di-allylamino. In certain embodiments, the R$^1$ group is 2-dibenzylaminoethoxy.

In other embodiments, the R$^3$ moiety of the R$^1$ group of formula I is a protected aldehyde group. In certain embodiments the protected aldehydo moiety of R$^3$ is an acyclic acetal, a cyclic acetal, a hydrazone, or an imine. Exemplary R$^3$ groups include dimethyl acetal, diethyl acetal, diisopropyl acetal, dibenzyl acetal, bis(2-nitrobenzyl)acetal, 1,3-dioxane, 1,3-dioxolane, and semicarbazone. In certain embodiments, R$^3$ is an acyclic acetal or a cyclic acetal. In other embodiments, R$^3$ is a dibenzyl acetal.

In yet other embodiments, the R$^3$ moiety of the R$^1$ group of formula I is a protected carboxylic acid group. In certain embodiments, the protected carboxylic acid moiety of R$^3$ is an optionally substituted ester selected from C$_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of R$^3$ is an oxazoline or an ortho ester. Examples of such protected carboxylic acid moieties include oxazolin-2-yl and 2-methoxy-[1,3]dioxin-2-yl. In certain embodiments, the R$^1$ group is oxazolin-2-ylmethoxy or 2-oxazolin-2-yl-1-propoxy.

According to another embodiments, the R$^3$ moiety of the R$^1$ group of formula I is a protected thiol group. In certain embodiments, the protected thiol of R$^3$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, R$^3$ is an optionally substituted thioether selected from alkyl, benzyl, or triphenylmethyl, or trichloroethoxycarbonyl thioester. In certain embodiments, R$^3$ is —S—S-pyridin-2-yl, —S—SBn, —S—SCH$_3$, or —S—S(p-ethynylbenzyl). In other embodiments, R$^3$ is —S—S-pyridin-2-yl. In still other embodiments, the R$^1$ group is 2-triphenylmethylsulfanyl-ethoxy.

In certain embodiments, the R$^3$ moiety of the R$^1$ group of formula I is a crown ether. Examples of such crown ethers include 12-crown-4, 15-crown-5, and 18-crown-6.

In still other embodiments, the R$^3$ moiety of the R$^1$ group of formula I is a detectable moiety. According to one aspect of the invention, the R$^3$ moiety of the R$^1$ group of formula I is a fluorescent moiety. Such fluorescent moieties are well known in the art and include coumarins, quinolones, benzoisoquinolones, hostasol, and Rhodamine dyes, to name but a few. Exemplary fluorescent moieties of the R$^3$ group of R$^1$ include anthracen-9-yl, pyren-4-yl, 9-H-carbazol-9-yl, the carboxylate of rhodamine B, and the carboxylate of coumarin 343. In certain embodiments, the R$^3$ moiety of the R$^1$ group of formula I is a detectable moiety selected from:

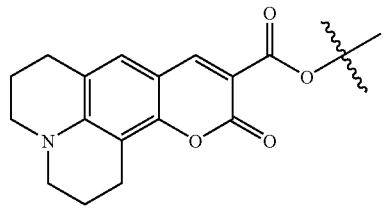

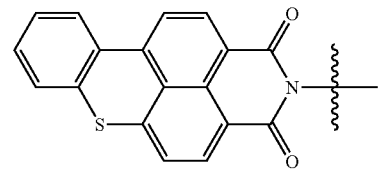

-continued

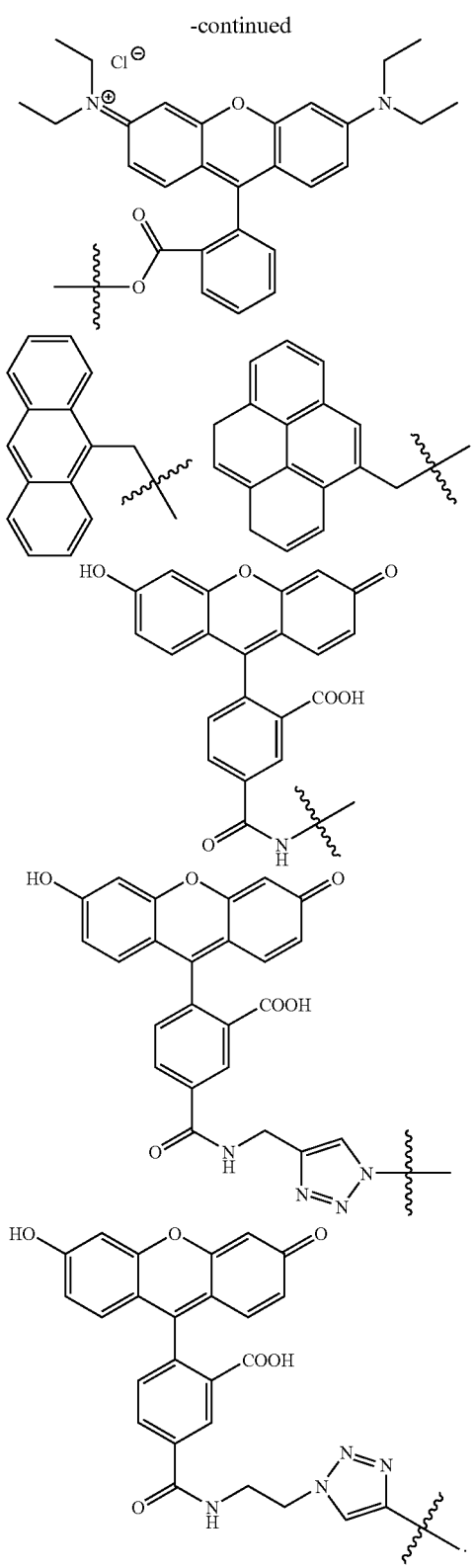

In certain embodiments, the R³ moiety of the R¹ group of formula I is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain R³ moieties of the present invention are suitable for Click chemistry.

Compounds of formula I having R³ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the R¹ groups of a compound of formula I to a macromolecule via Click chemistry. Yet another embodiment of the present invention provides a macromolecule conjugated to a compound of formula I via the R¹ group.

According to one embodiment, the R³ moiety of the R¹ group of formula I is an azide-containing group. According to another embodiment, the R³ moiety of the R¹ group of formula I is an alkyne-containing group. In certain embodiments, the R³ moiety of the R¹ group of formula I has a terminal alkyne moiety. In other embodiments, R³ moiety of the R¹ group of formula I is an alkyne moiety having an electron withdrawing group. Accordingly, in such embodiments, the R³ moiety of the R¹ group of formula I is

wherein E is an electron withdrawing group and y is 0-6. Such electron withdrawing groups are known to one of ordinary skill in the art. In certain embodiments, E is an ester. In other embodiments, the R³ moiety of the R¹ group of formula I is

wherein E is an electron withdrawing group, such as a —C(O)O— group and y is 0-6.

As defined generally above, Q is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO₂—, —NHSO₂—, —SO₂NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, Q is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, $R^x$ is a crosslinkable amino acid side-chain group. Such crosslinkable amino acid side-chain groups include tyrosine, serine, cysteine, threonine, aspartic acid (also known as aspartate, when charged), glutamic acid (also known as glutamate, when charged), asparagine, histidine, lysine, arginine, glutamine, or a benzimidazole-functionalized amino acid.

As defined above, $R^x$ is a natural or unnatural amino acid side-chain group capable of forming cross-links. It will be appreciated that a variety of amino acid side-chain functional groups are capable of such cross-linking, including, but not limited to, carboxylate, hydroxyl, thiol, and amino groups. Examples of $R^x$ moieties having functional groups capable of forming cross-links include a glutamic acid side-chain, —CH$_2$C(O)OH, an aspartic acid side-chain, —CH$_2$CH$_2$C(O)OH, a cystein side-chain, —CH$_2$SH, a serine side-chain, —CH$_2$OH, an aldehyde containing side-chain, —CH$_2$C(O)H, a lysine side-chain, —(CH$_2$)$_4$NH$_2$, an arginine side-chain, —(CH$_2$)$_3$NHC(=NH)NH$_2$, a histidine side-chain, —CH$_2$-imidazol-4-yl.

As defined above, $R^y$ forms a hydrophobic D,L-mixed amino acid block. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboylate functional groups of $R^x$ and $R^y$ are as described herein.

In other embodiments, $R^y$ consists of a mixture of D-hydrophobic and L-hydrophilic amino acid side-chain groups such that the overall poly(amino acid) block comprising $R^y$ is hydrophobic and is a mixture of D- and L-configured amino acids. Such mixtures of amino acid side-chain groups include L-tyrosine and D-leucine, L-tyrosine and D-phenylalanine, L-serine and D-phenylalanine, L-aspartic acid and D-phenylalanine, L-glutamic acid and D-phenylalanine, L-tyrosine and D-benzyl glutamate, L-tyrosine and D-benzyl aspartate, L-serine and D-benzyl glutamate, L-serine and D-benzyl aspartate, L-aspartic acid and D-benzyl glutamate, L-aspartic acid and D-benzyl aspartate, L-glutamic acid and D-benzyl glutamate, L-glutamic acid and D-benzyl aspartate, L-aspartic acid and D-leucine, and L-glutamic acid and D-leucine. Ratios (D-hydrophobic to L-hydrophilic) of such amino acid combinations can range between 5-95 mol %.

In certain embodiments, $R^y$ consists of a mixture of D-hydrophobic and L-hydrophobic amino acids. Such mixtures include D-benzyl glutamate and L-benzyl glutamate, D-benzyl aspartate and L-benzyl aspartate, D-benzyl aspartate and L-benzyl glutamate, or D-benzyl glutamate and L-benzyl aspartate. Exemplary compounds are set forth below.

As defined generally above, the $R^{2a}$ group of formula I is a mono-protected amine, a di-protected amine, —NHR$^4$, —N(R$^4$)$_2$, —NHC(O)R$^4$, —NR$^4$C(O)R$^4$, —NHC(O)NHR$^4$, —NHC(O)N(R$^4$)$_2$, —NR$^4$C(O)NHR$^4$, —NR$^4$C(O)N(R$^4$)$_2$, —NHC(O)OR$^4$, —NR$^4$C(O)OR$^4$, —NHSO$_2$R$^4$, or —NR$^4$SO$_2$R$^4$, wherein each R$^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two R$^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

In certain embodiments, the $R^{2a}$ group of formula I is —NHR$^4$ or —N(R$^4$)$_2$ wherein each R$^4$ is an optionally substituted aliphatic group. One exemplary R$^4$ group is 5-norbornen-2-yl-methyl. According to yet another aspect of the present invention, the $R^{2a}$ group of formula I is —NHR$^4$ wherein R$^4$ is a $C_{1-6}$ aliphatic group substituted with N$_3$. Examples include —CH$_2$N$_3$. In some embodiments, R$^4$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, R$^4$ is an optionally substituted $C_{2-6}$ alkenyl group. Examples include vinyl, allyl, crotyl, 2-propenyl, and but-3-enyl. When R$^4$ group is a substituted aliphatic group, suitable substituents on R$^4$ include N$_3$, CN, and halogen. In certain embodiments, R$^4$ is —CH$_2$CN, —CH$_2$CH$_2$CN, —CH$_2$CH(OCH$_3$)$_2$, 4-(bisbenzyloxymethyl)phenylmethyl, and the like.

According to another aspect of the present invention, the $R^{2a}$ group of formula I is —NHR$^4$ wherein R$^4$ is an optionally substituted $C_{2-6}$ alkynyl group. Examples include —CC≡CH, —CH$_2$C≡CH, —CH$_2$C≡CCH$_3$, and —CH$_2$CH$_2$C≡CH.

In certain embodiments, the $R^{2a}$ group of formula I is —NHR$^4$ wherein R$^4$ is an optionally substituted 5-8-membered aryl ring. In certain embodiments, R$^4$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^{2a}$ is 4-t-butoxycarbonylaminophenylamino, 4-azidomethylphenamino, or 4-propargyloxyphenylamino.

In certain embodiments, the $R^{2a}$ group of formula I is —NHR$^4$ wherein R$^4$ is an optionally substituted phenyl ring. Suitable substituents on the R$^4$ phenyl ring include halogen; —(CH$_2$)$_{0-4}$R°; —(CH$_2$)$_{0-4}$OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —(CH$_2$)$_{0-4}$SC(O)R°; —(CH$_2$)$_{0-4}$C(O)NR°$_2$; —C(S)NR°$_2$; —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; SiR°$_3$; wherein each independent occurrence of R° is as defined herein supra. In other embodiments, the $R^{2a}$ group of formula I is —NHR$^4$ wherein R$^4$ is phenyl substituted with one or more optionally substituted C$_{1-6}$ aliphatic groups. In still other embodiments, R$^4$ is phenyl substituted with vinyl, allyl, acetylenyl, —CH$_2$N$_3$, —CH$_2$CH$_2$N$_3$, —CH$_2$C≡CCH$_3$, or —CH$_2$C≡CH.

In certain embodiments, the $R^{2a}$ group of formula I is —NHR$^4$ wherein R$^4$ is phenyl substituted with N$_3$, N(R°)$_2$, CO$_2$R°, or C(O)R° wherein each R° is independently as defined herein supra.

In certain embodiments, the $R^{2a}$ group of formula I is —N(R$^4$)$_2$ wherein each R$^4$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^{2a}$ group of formula I is —N(R$^4$)$_2$ wherein the two R$^4$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two R$^4$ groups are taken together to form a 5-6-membered saturated or partially unsaturated ring having one nitrogen wherein said ring is substituted with one or two oxo groups. Such $R^{2a}$ groups include, but are not limited to, phthalimide, maleimide and succinimide.

In certain embodiments, the $R^{2a}$ group of formula I is a mono-protected or di-protected amino group. In certain embodiments $R^{2a}$ is a mono-protected amine. In certain embodiments $R^{2a}$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^{2a}$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^{2a}$ moiety is phthalimido. In other embodiments, the $R^{2a}$ moiety is mono- or di-benzylamino or mono- or di-allylamino.

In certain embodiments, the $R^{2a}$ group of formula I comprises a group suitable for Click chemistry. One of ordinary skill in the art would recognize that certain $R^{2a}$ groups of the present invention are suitable for Click chemistry.

Compounds of formula I having $R^{2a}$ groups comprising groups suitable for Click chemistry are useful for conjugating said compounds to biological systems such as proteins, viruses, and cells, to name but a few. After conjugation to a biomolecule, drug, cell, substrate, or the like, the other end-group functionality, corresponding to the R$^1$ moiety of formula I, can be used to attach targeting groups for cell specific delivery including, but not limited to, fluorescent dyes, covalent attachment to surfaces, and incorporation into hydrogels. Thus, another embodiment of the present invention provides a method of conjugating the $R^{2a}$ group of a compound of formula I to a fluorescent dye, small molecule drug, or macromolecule via Click chemistry. Yet another embodiment of the present invention provides a macromolecule conjugated to a compound of formula I via the $R^{2a}$ group.

According to one embodiment, the $R^{2a}$ group of formula I is an azide-containing group. According to another embodiment, the $R^{2a}$ group of formula I is an alkyne-containing group.

In certain embodiments, the $R^{2a}$ group of formula I has a terminal alkyne moiety. In other embodiments, the $R^{2a}$ group of formula I is an alkyne-containing moiety having an electron withdrawing group. Accordingly, in such embodiments, the $R^{2a}$ group of formula I is

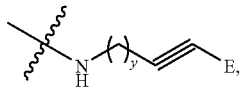

wherein E is an electron withdrawing group and y is 0-6. Such electron withdrawing groups are known to one of ordinary skill in the art. In certain embodiments, E is an ester. In other embodiments, the $R^{2a}$ group of formula I is

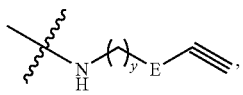

wherein E is an electron withdrawing group, such as a —C(O)O— group and y is 0-6.

Table 1 sets forth exemplary compounds of the present invention having the formula:

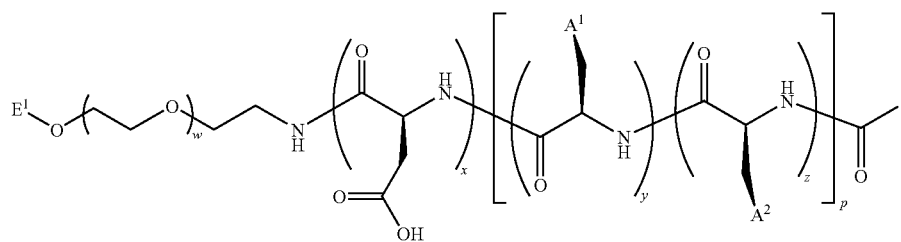

wherein w is 50 to 400, x is 0-30, y is 1-50, z is 1-50, and p is the sum of y and z.

TABLE 1

| Compound | A¹ | A² | E¹ |
|---|---|---|---|
| 1 | benzyl ester | 4-hydroxyphenyl | propargyl |
| 2 | benzyl ester | 4-hydroxyphenyl | azidoethyl |
| 3 | benzyl ester | 4-hydroxyphenyl | aminoethyl |
| 4 | benzyl ester | 4-hydroxyphenyl | oxobutyl (aldehyde) |
| 5 | benzyl ester | carboxymethyl | propargyl |
| 6 | benzyl ester | carboxymethyl | azidoethyl |
| 7 | benzyl ester | carboxymethyl | aminoethyl |

TABLE 1-continued

| Compound | A¹ | A² | E¹ |
|---|---|---|---|
| 8 | benzyl ester -CH2-C(=O)-O-CH2-Ph | -CH2-COOH | -CH2-CHO |
| 9 | benzyl ester -CH2-C(=O)-O-CH2-Ph | -OH | -C≡CH |
| 10 | benzyl ester -CH2-C(=O)-O-CH2-Ph | -OH | -CH2-N3 |
| 11 | benzyl ester -CH2-C(=O)-O-CH2-Ph | -OH | -CH2-NH2 |
| 12 | benzyl ester -CH2-C(=O)-O-CH2-Ph | -OH | -CH2-CHO |
| 13 | phenyl | 4-hydroxyphenyl | -C≡CH |
| 14 | phenyl | 4-hydroxyphenyl | -CH2-N3 |
| 15 | phenyl | 4-hydroxyphenyl | -CH2-NH2 |
| 16 | phenyl | 4-hydroxyphenyl | -CH2-CHO |
| 17 | phenyl | -CH2-COOH | -C≡CH |
| 18 | phenyl | -CH2-COOH | -CH2-N3 |
| 19 | phenyl | -CH2-COOH | -CH2-NH2 |

TABLE 1-continued

| Compound | A¹ | A² | E¹ |
|---|---|---|---|
| 20 | phenyl | -CH₂-COOH | -CH₂-CHO |
| 21 | phenyl | -OH | -CH₂-C≡CH |
| 22 | phenyl | -OH | -CH₂-CH₂-N₃ |
| 23 | phenyl | -OH | -CH₂-CH₂-NH₂ |
| 24 | phenyl | -OH | -CH₂-CHO |
| 25 | benzyl ester (-C(O)O-CH₂-C₆H₅) | 4-hydroxyphenyl | -CH₂-C≡CH |
| 26 | benzyl ester | 4-hydroxyphenyl | -CH₂-CH₂-N₃ |
| 27 | benzyl ester | 4-hydroxyphenyl | -CH₂-CH₂-NH₂ |
| 28 | benzyl ester | 4-hydroxyphenyl | -CH₂-CHO |
| 29 | benzyl ester | -CH₂-COOH | -CH₂-C≡CH |
| 30 | benzyl ester | -CH₂-COOH | -CH₂-CH₂-N₃ |

TABLE 1-continued

| Compound | A¹ | A² | E¹ |
|---|---|---|---|
| 31 | benzyl ester (–C(O)O–CH₂–C₆H₅) | –CH₂–C(O)OH | H₂N–CH₂–CH₂– |
| 32 | benzyl ester | –CH₂–C(O)OH | OHC–CH₂–CH₂– |
| 33 | benzyl ester | –OH | HC≡C–CH₂– |
| 34 | benzyl ester | –OH | N₃–CH₂–CH₂– |
| 35 | benzyl ester | –OH | H₂N–CH₂–CH₂– |
| 36 | benzyl ester | –OH | OHC–CH₂–CH₂– |
| 37 | benzyl ester | –C(O)OH | HC≡C–CH₂– |
| 38 | benzyl ester | –C(O)OH | N₃–CH₂–CH₂– |
| 39 | benzyl ester | –C(O)OH | H₂N–CH₂–CH₂– |
| 40 | benzyl ester | –C(O)OH | OHC–CH₂–CH₂– |

TABLE 1-continued

| Compound | A¹ | A² | E¹ |
|---|---|---|---|
| 41 | phenyl | −COOH | alkyne (propargyl) |
| 42 | phenyl | −COOH | −CH₂CH₂N₃ |
| 43 | phenyl | −COOH | H₂N−CH₂CH₂− |
| 44 | phenyl | −COOH | −CH₂CH₂CHO |
| 45 | isopropyl | −COOH | alkyne (propargyl) |
| 46 | isopropyl | −COOH | −CH₂CH₂N₃ |
| 47 | isopropyl | −COOH | H₂N−CH₂CH₂− |
| 48 | isopropyl | −COOH | −CH₂CH₂CHO |
| 49 | isopropyl | 4-hydroxyphenyl | alkyne (propargyl) |
| 50 | isopropyl | 4-hydroxyphenyl | −CH₂CH₂N₃ |
| 51 | isopropyl | 4-hydroxyphenyl | H₂N−CH₂CH₂− |
| 52 | isopropyl | 4-hydroxyphenyl | −CH₂CH₂CHO |
| 53 | isopropyl | −CH₂COOH | alkyne (propargyl) |
| 54 | isopropyl | −CH₂COOH | −CH₂CH₂N₃ |

TABLE 1-continued

| Compound | A¹ | A² | E¹ |
|---|---|---|---|
| 55 | isobutyl | CH₂COOH | H₂N-CH₂CH₂- |
| 56 | isobutyl | CH₂COOH | OHC-CH₂CH₂- |
| 57 | isobutyl | CH₂OH | HC≡C-CH₂- |
| 58 | isobutyl | CH₂OH | N₃-CH₂CH₂- |
| 59 | isobutyl | CH₂OH | H₂N-CH₂CH₂- |
| 60 | isobutyl | CH₂OH | OHC-CH₂CH₂- |

Table 2 sets forth exemplary compounds of the present invention having the formula:

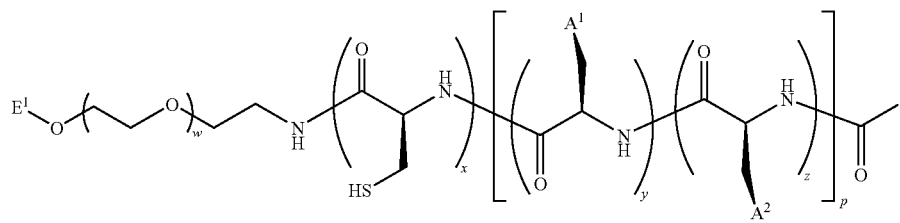

wherein w is 50 to 400, x is 0-30, y is 1-50, z is 1-50, and p is the sum of y and z.

TABLE 2

| Compound | A¹ | A² | E¹ |
|---|---|---|---|
| 61 | -CH₂C(O)OCH₂-C₆H₅ | -C₆H₄-OH | HC≡C-CH₂- |
| 62 | -CH₂C(O)OCH₂-C₆H₅ | -C₆H₄-OH | N₃-CH₂CH₂- |

TABLE 2-continued

| Compound | A¹ | A² | E¹ |
|---|---|---|---|
| 63 | benzyl ester -CH2-C(=O)-O-CH2-C6H5 | 4-hydroxyphenyl | H2N-CH2CH2- |
| 64 | benzyl ester | 4-hydroxyphenyl | OHC-CH2CH2- |
| 65 | benzyl ester | -CH2-COOH | HC≡C-CH2- |
| 66 | benzyl ester | -CH2-COOH | N3-CH2CH2- |
| 67 | benzyl ester | -CH2-COOH | H2N-CH2CH2- |
| 68 | benzyl ester | -CH2-COOH | OHC-CH2CH2- |
| 69 | benzyl ester | -OH | HC≡C-CH2- |
| 70 | benzyl ester | -OH | N3-CH2CH2- |
| 71 | benzyl ester | -OH | H2N-CH2CH2- |
| 72 | benzyl ester | -OH | OHC-CH2CH2- |

TABLE 2-continued

| Compound | A¹ | A² | E¹ |
|---|---|---|---|
| 73 | phenyl | 4-hydroxyphenyl | ethynyl (–C≡CH) |
| 74 | phenyl | 4-hydroxyphenyl | 2-azidoethyl (N₃–CH₂CH₂–) |
| 75 | phenyl | 4-hydroxyphenyl | 2-aminoethyl (H₂N–CH₂CH₂–) |
| 76 | phenyl | 4-hydroxyphenyl | 3-oxopropyl (OHC–CH₂CH₂–) |
| 77 | phenyl | –CH₂–C(=O)OH | ethynyl |
| 78 | phenyl | –CH₂–C(=O)OH | 2-azidoethyl |
| 79 | phenyl | –CH₂–C(=O)OH | 2-aminoethyl |
| 80 | phenyl | –CH₂–C(=O)OH | 3-oxopropyl |
| 81 | phenyl | –CH₂OH | ethynyl |
| 82 | phenyl | –CH₂OH | 2-azidoethyl |
| 83 | phenyl | –CH₂OH | 2-aminoethyl |
| 84 | phenyl | –CH₂OH | 3-oxopropyl |
| 85 | benzyloxycarbonyl (–C(=O)OCH₂Ph) | 4-hydroxyphenyl | ethynyl |

TABLE 2-continued

| Compound | A¹ | A² | E¹ |
|---|---|---|---|
| 86 | benzyl ester (–C(=O)O–CH₂–C₆H₅) | 4-hydroxyphenyl | N₃–CH₂CH₂– |
| 87 | benzyl ester | 4-hydroxyphenyl | H₂N–CH₂CH₂– |
| 88 | benzyl ester | 4-hydroxyphenyl | OHC–CH₂CH₂– |
| 89 | benzyl ester | –CH₂–C(=O)OH | HC≡C–CH₂– |
| 90 | benzyl ester | –CH₂–C(=O)OH | N₃–CH₂CH₂– |
| 91 | benzyl ester | –CH₂–C(=O)OH | H₂N–CH₂CH₂– |
| 92 | benzyl ester | –CH₂–C(=O)OH | OHC–CH₂CH₂– |
| 93 | benzyl ester | –CH₂–OH | HC≡C–CH₂– |
| 94 | benzyl ester | –CH₂–OH | N₃–CH₂CH₂– |
| 95 | benzyl ester | –CH₂–OH | H₂N–CH₂CH₂– |

TABLE 2-continued

| Compound | A¹ | A² | E¹ |
|---|---|---|---|
| 96 | benzyl ester (-C(O)OCH₂Ph) | -OH (methanol) | -CH₂C(O)H |
| 97 | benzyl ester | -C(O)OH | -CH₂C≡CH |
| 98 | benzyl ester | -C(O)OH | -CH₂CH₂N₃ |
| 99 | benzyl ester | -C(O)OH | -CH₂CH₂NH₂ |
| 100 | benzyl ester | -C(O)OH | -CH₂C(O)H |
| 101 | phenyl | -C(O)OH | -CH₂C≡CH |
| 102 | phenyl | -C(O)OH | -CH₂CH₂N₃ |
| 103 | phenyl | -C(O)OH | -CH₂CH₂NH₂ |
| 104 | phenyl | -C(O)OH | -CH₂C(O)H |
| 105 | isobutyl | -C(O)OH | -CH₂C≡CH |
| 106 | isobutyl | -C(O)OH | -CH₂CH₂N₃ |
| 107 | isobutyl | -C(O)OH | -CH₂CH₂NH₂ |

TABLE 2-continued
| Compound | A¹ | A² | E¹ |
|---|---|---|---|
| 108 | 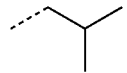 | 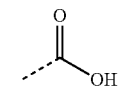 | 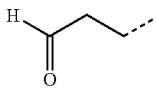 |
| 109 | 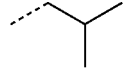 | 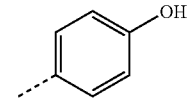 | 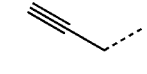 |
| 110 | 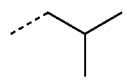 | 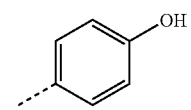 | 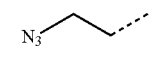 |
| 111 | 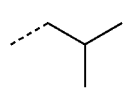 | 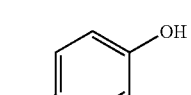 | 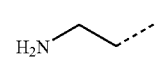 |
| 112 | 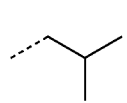 | 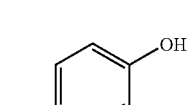 | 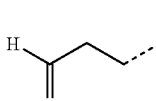 |
| 113 | 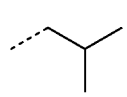 | 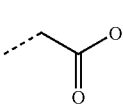 | 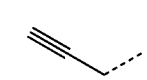 |
| 114 | 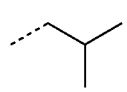 | 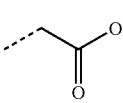 | 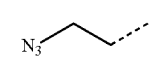 |
| 115 | 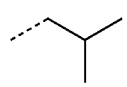 | 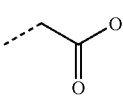 | 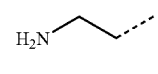 |
| 116 | 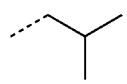 | 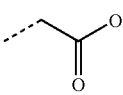 | 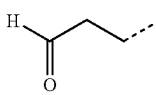 |
| 117 | 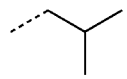 |  | 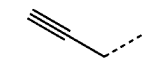 |
| 118 | 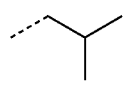 |  | 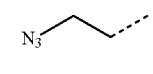 |
| 119 | 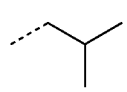 |  | 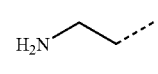 |
| 120 | 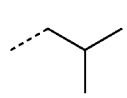 |  | 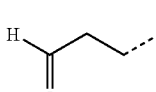 |

Table 3 sets forth exemplary compounds of the present invention having the formula:

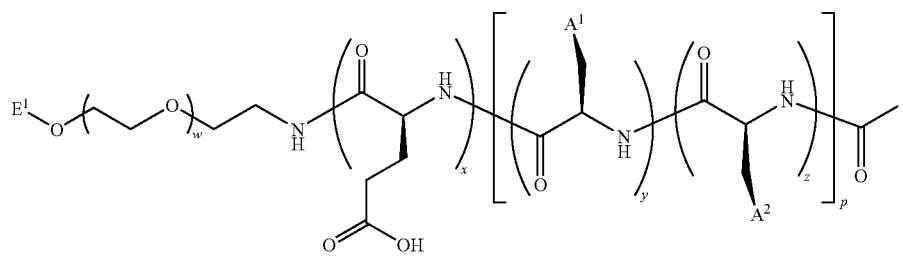

wherein w is 50 to 400, x is 0-30, y is 1-50, z is 1-50, and p is the sum of y and z.

TABLE 3

| Compound | A$^1$ | A$^2$ | E$^1$ |
|---|---|---|---|
| 121 | benzyl ester | 4-hydroxyphenyl | propargyl |
| 122 | benzyl ester | 4-hydroxyphenyl | N$_3$-CH$_2$CH$_2$- |
| 123 | benzyl ester | 4-hydroxyphenyl | H$_2$N-CH$_2$CH$_2$- |
| 124 | benzyl ester | 4-hydroxyphenyl | OHC-CH$_2$CH$_2$- |
| 125 | benzyl ester | carboxyl | propargyl |
| 126 | benzyl ester | carboxyl | N$_3$-CH$_2$CH$_2$- |
| 127 | benzyl ester | carboxyl | H$_2$N-CH$_2$CH$_2$- |

TABLE 3-continued

| Compound | A$^1$ | A$^2$ | E$^1$ |
|---|---|---|---|
| 128 | benzyl ester (–CH$_2$–C(O)O–CH$_2$–C$_6$H$_5$) | –CH$_2$–C(O)OH | –CH$_2$–CHO |
| 129 | benzyl ester | –OH | –C≡CH (propargyl) |
| 130 | benzyl ester | –OH | –CH$_2$–N$_3$ |
| 131 | benzyl ester | –OH | –CH$_2$–NH$_2$ |
| 132 | benzyl ester | –OH | –CH$_2$–CHO |
| 133 | phenyl | 4-hydroxyphenyl | –C≡CH |
| 134 | phenyl | 4-hydroxyphenyl | –CH$_2$–N$_3$ |
| 135 | phenyl | 4-hydroxyphenyl | –CH$_2$–NH$_2$ |
| 136 | phenyl | 4-hydroxyphenyl | –CH$_2$–CHO |
| 137 | phenyl | –CH$_2$–C(O)OH | –C≡CH |
| 138 | phenyl | –CH$_2$–C(O)OH | –CH$_2$–N$_3$ |

TABLE 3-continued

| Compound | A¹ | A² | E¹ |
|---|---|---|---|
| 139 | phenyl | -CH₂C(O)OH | H₂N-CH₂CH₂- |
| 140 | phenyl | -CH₂C(O)OH | OHC-CH₂CH₂- |
| 141 | phenyl | -OH (methoxy) | HC≡C-CH₂- |
| 142 | phenyl | -OH (methoxy) | N₃-CH₂CH₂- |
| 143 | phenyl | -OH (methoxy) | H₂N-CH₂CH₂- |
| 144 | phenyl | -OH (methoxy) | OHC-CH₂CH₂- |
| 145 | benzyl ester | 4-hydroxyphenyl | HC≡C-CH₂- |
| 146 | benzyl ester | 4-hydroxyphenyl | N₃-CH₂CH₂- |
| 147 | benzyl ester | 4-hydroxyphenyl | H₂N-CH₂CH₂- |
| 148 | benzyl ester | 4-hydroxyphenyl | OHC-CH₂CH₂- |
| 149 | benzyl ester | -CH₂C(O)OH | HC≡C-CH₂- |

TABLE 3-continued

| Compound | A¹ | A² | E¹ |
|---|---|---|---|
| 150 | benzyl ester (−C(O)O−CH₂−C₆H₅) | −CH₂−C(O)OH | N₃−CH₂CH₂− |
| 151 | benzyl ester | −CH₂−C(O)OH | H₂N−CH₂CH₂− |
| 152 | benzyl ester | −CH₂−C(O)OH | OHC−CH₂CH₂− |
| 153 | benzyl ester | −CH₂−OH | HC≡C−CH₂− |
| 154 | benzyl ester | −CH₂−OH | N₃−CH₂CH₂− |
| 155 | benzyl ester | −CH₂−OH | H₂N−CH₂CH₂− |
| 156 | benzyl ester | −CH₂−OH | OHC−CH₂CH₂− |
| 157 | benzyl ester | −C(O)OH | HC≡C−CH₂− |
| 158 | benzyl ester | −C(O)OH | N₃−CH₂CH₂− |
| 159 | benzyl ester | −C(O)OH | H₂N−CH₂CH₂− |

TABLE 3-continued

| Compound | A¹ | A² | E¹ |
|---|---|---|---|
| 160 | benzyl ester (–C(O)O–CH₂–C₆H₅) | –COOH | –CH₂CH₂–CHO |
| 161 | phenyl | –COOH | –CH₂–C≡CH |
| 162 | phenyl | –COOH | –CH₂CH₂–N₃ |
| 163 | phenyl | –COOH | –CH₂CH₂–NH₂ |
| 164 | phenyl | –COOH | –CH₂CH₂–CHO |
| 165 | isobutyl | –COOH | –CH₂–C≡CH |
| 166 | isobutyl | –COOH | –CH₂CH₂–N₃ |
| 167 | isobutyl | –COOH | –CH₂CH₂–NH₂ |
| 168 | isobutyl | –COOH | –CH₂CH₂–CHO |
| 169 | isobutyl | 4-hydroxyphenyl | –CH₂–C≡CH |
| 170 | isobutyl | 4-hydroxyphenyl | –CH₂CH₂–N₃ |
| 171 | isobutyl | 4-hydroxyphenyl | –CH₂CH₂–NH₂ |
| 172 | isobutyl | 4-hydroxyphenyl | –CH₂CH₂–CHO |

TABLE 3-continued

| Compound | A¹ | A² | E¹ |
|---|---|---|---|
| 173 | isopropyl | CH₂COOH | propargyl |
| 174 | isopropyl | CH₂COOH | N₃-CH₂CH₂- |
| 175 | isopropyl | CH₂COOH | H₂N-CH₂CH₂- |
| 176 | isopropyl | CH₂COOH | OHC-CH₂CH₂- |
| 177 | isopropyl | CH₂OH | propargyl |
| 178 | isopropyl | CH₂OH | N₃-CH₂CH₂- |
| 179 | isopropyl | CH₂OH | H₂N-CH₂CH₂- |
| 180 | isopropyl | CH₂OH | OHC-CH₂CH₂- |

Table 4 sets forth exemplary compounds of the present invention having the formula:

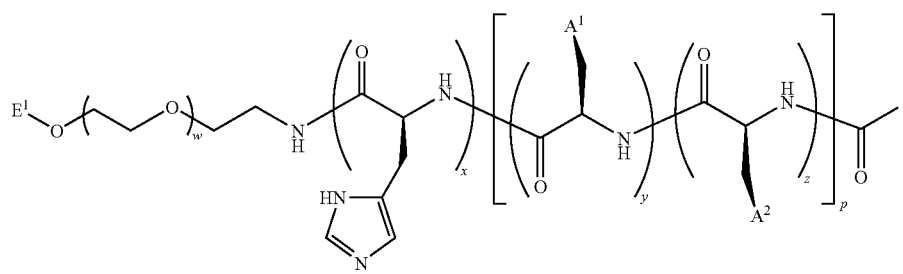

wherein w is 50 to 400, x is 0-30, y is 1-50, z is 1-50, and p is the sum of y and z.

TABLE 4

| Compound | A¹ | A² | E¹ |
|---|---|---|---|
| 181 | -CH₂-C(O)-O-CH₂-C₆H₅ | -C₆H₄-OH | propargyl |

TABLE 4-continued

| Compound | A¹ | A² | E¹ |
|---|---|---|---|
| 182 | benzyl ester (-CH₂-C(=O)-O-CH₂-C₆H₅) | 4-hydroxyphenyl | N₃-CH₂CH₂- |
| 183 | benzyl ester | 4-hydroxyphenyl | H₂N-CH₂CH₂- |
| 184 | benzyl ester | 4-hydroxyphenyl | OHC-CH₂CH₂- |
| 185 | benzyl ester | -CH₂-C(=O)-OH | HC≡C-CH₂- |
| 186 | benzyl ester | -CH₂-C(=O)-OH | N₃-CH₂CH₂- |
| 187 | benzyl ester | -CH₂-C(=O)-OH | H₂N-CH₂CH₂- |
| 188 | benzyl ester | -CH₂-C(=O)-OH | OHC-CH₂CH₂- |
| 189 | benzyl ester | -CH₂-OH | HC≡C-CH₂- |
| 190 | benzyl ester | -CH₂-OH | N₃-CH₂CH₂- |

TABLE 4-continued
| Compound | A¹ | A² | E¹ |
|---|---|---|---|
| 191 | 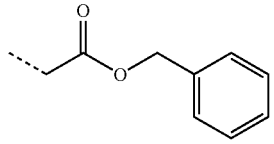 |  | 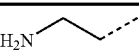 |
| 192 | 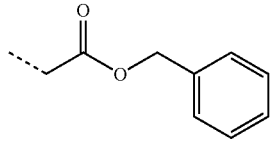 |  | 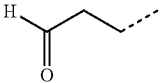 |
| 193 | 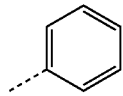 | 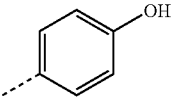 | 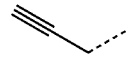 |
| 194 | 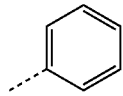 | 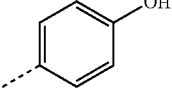 | 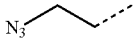 |
| 195 | 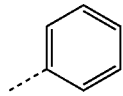 | 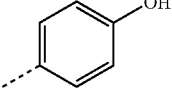 | 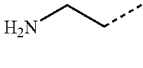 |
| 196 | 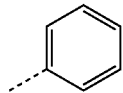 | 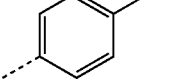 | 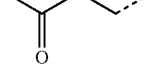 |
| 197 | 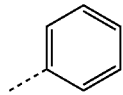 | 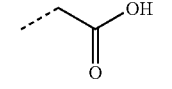 | 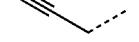 |
| 198 | 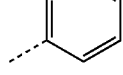 | 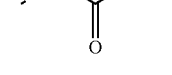 |  |
| 199 | 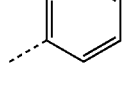 | 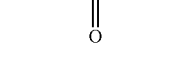 |  |
| 200 | 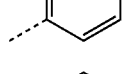 | 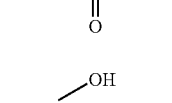 | 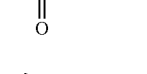 |
| 201 | 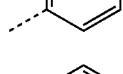 |  |  |
| 202 | 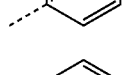 |  |  |
| 203 | 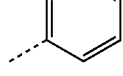 |  |  |

TABLE 4-continued

| Compound | A¹ | A² | E¹ |
|---|---|---|---|
| 204 | phenyl | –OH (methoxy) | propanal |
| 205 | benzyl ester | 4-hydroxyphenyl | alkyne |
| 206 | benzyl ester | 4-hydroxyphenyl | azidoethyl |
| 207 | benzyl ester | 4-hydroxyphenyl | aminoethyl |
| 208 | benzyl ester | 4-hydroxyphenyl | propanal |
| 209 | benzyl ester | carboxymethyl | alkyne |
| 210 | benzyl ester | carboxymethyl | azidoethyl |
| 211 | benzyl ester | carboxymethyl | aminoethyl |
| 212 | benzyl ester | carboxymethyl | propanal |
| 213 | benzyl ester | –OH (methoxy) | alkyne |

TABLE 4-continued
| Compound | A¹ | A² | E¹ |
|---|---|---|---|
| 214 |  | —OH |  N₃ |
| 215 |  | —OH |  H₂N |
| 216 |  | —OH |  |
| 217 |  |  OH |  |
| 218 |  |  OH |  N₃ |
| 219 |  |  OH |  H₂N |
| 220 |  |  OH |  |
| 221 |  |  OH |  |
| 222 |  |  OH |  N₃ |
| 223 |  |  OH |  H₂N |
| 224 |  |  OH |  |

TABLE 4-continued

| Compound | A¹ | A² | E¹ |
|---|---|---|---|
| 225 | isopropyl | -COOH | -C≡CH |
| 226 | isopropyl | -COOH | -CH₂CH₂N₃ |
| 227 | isopropyl | -COOH | -CH₂CH₂NH₂ |
| 228 | isopropyl | -COOH | -CH₂CH₂C(O)H |
| 229 | isopropyl | -C₆H₄-OH | -C≡CH |
| 230 | isopropyl | -C₆H₄-OH | -CH₂CH₂N₃ |
| 231 | isopropyl | -C₆H₄-OH | -CH₂CH₂NH₂ |
| 232 | isopropyl | -C₆H₄-OH | -CH₂CH₂C(O)H |
| 233 | isopropyl | -CH₂COOH | -C≡CH |
| 234 | isopropyl | -CH₂COOH | -CH₂CH₂N₃ |
| 235 | isopropyl | -CH₂COOH | -CH₂CH₂NH₂ |
| 236 | isopropyl | -CH₂COOH | -CH₂CH₂C(O)H |
| 237 | isopropyl | -CH₂OH | -C≡CH |
| 238 | isopropyl | -CH₂OH | -CH₂CH₂N₃ |
| 239 | isopropyl | -CH₂OH | -CH₂CH₂NH₂ |

TABLE 4-continued

| Compound | A¹ | A² | E¹ |
|---|---|---|---|
| 240 | (isobutyl) | —OH | (4-oxobutyl, H-C(=O)-CH₂-CH₂-) |

Table 5 sets forth exemplary compounds of the present invention having the formula:

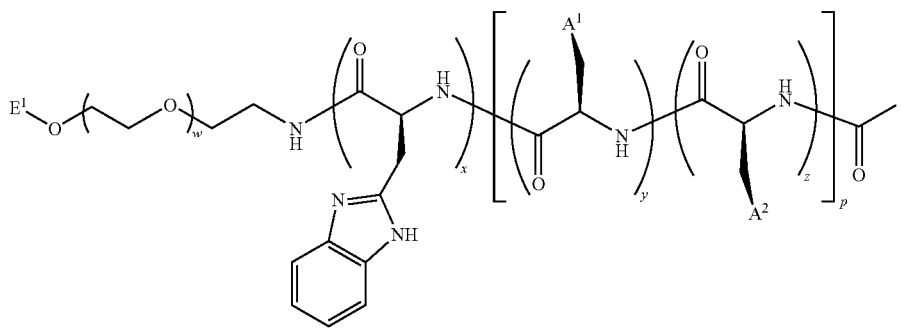

wherein w is 50 to 400, x is 0-30, y is 1-50, z is 1-50, and p is the sum of y and z.

TABLE 5

| Compound | A¹ | A² | E¹ |
|---|---|---|---|
| 241 | —CH₂—C(=O)—O—CH₂—C₆H₅ | 4-hydroxyphenyl | propargyl (HC≡C—CH₂—) |
| 242 | —CH₂—C(=O)—O—CH₂—C₆H₅ | 4-hydroxyphenyl | $N_3$—CH₂CH₂— |
| 243 | —CH₂—C(=O)—O—CH₂—C₆H₅ | 4-hydroxyphenyl | $H_2N$—CH₂CH₂— |
| 244 | —CH₂—C(=O)—O—CH₂—C₆H₅ | 4-hydroxyphenyl | H-C(=O)-CH₂-CH₂- |
| 245 | —CH₂—C(=O)—O—CH₂—C₆H₅ | —CH₂—C(=O)—OH | HC≡C—CH₂— |

TABLE 5-continued
| Compound | A¹ | A² | E¹ |
|---|---|---|---|
| 246 | 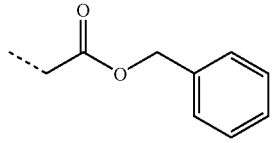 | 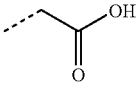 | 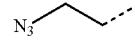 |
| 247 | 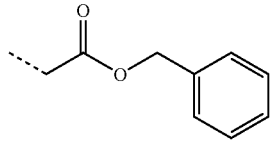 | 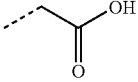 | 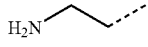 |
| 248 | 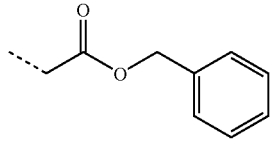 | 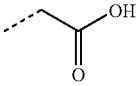 | 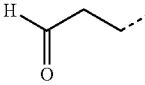 |
| 249 | 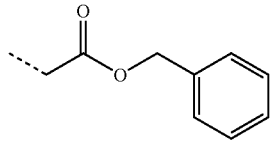 |  | 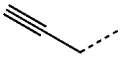 |
| 250 | 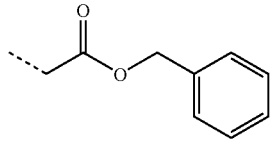 |  |  |
| 251 | 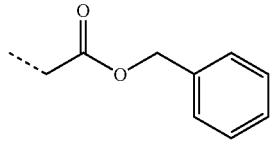 |  | 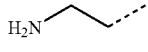 |
| 252 | 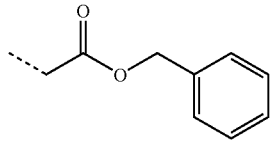 |  | 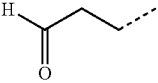 |
| 253 | 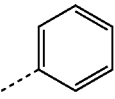 | 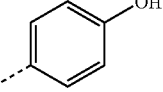 | 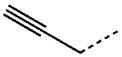 |
| 254 | 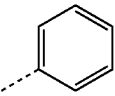 | 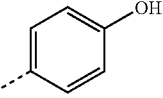 | 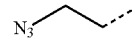 |
| 255 | 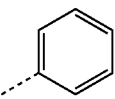 | 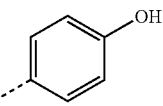 | 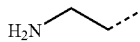 |

TABLE 5-continued

| Compound | A¹ | A² | E¹ |
|---|---|---|---|
| 256 | phenyl | 4-hydroxyphenyl | -CH₂CH₂CHO |
| 257 | phenyl | -CH₂COOH | -CH₂C≡CH |
| 258 | phenyl | -CH₂COOH | -CH₂CH₂N₃ |
| 259 | phenyl | -CH₂COOH | -CH₂CH₂NH₂ |
| 260 | phenyl | -CH₂COOH | -CH₂CH₂CHO |
| 261 | phenyl | -CH₂OH | -CH₂C≡CH |
| 262 | phenyl | -CH₂OH | -CH₂CH₂N₃ |
| 263 | phenyl | -CH₂OH | -CH₂CH₂NH₂ |
| 264 | phenyl | -CH₂OH | -CH₂CH₂CHO |
| 265 | benzyloxycarbonyl | 4-hydroxyphenyl | -CH₂C≡CH |
| 266 | benzyloxycarbonyl | 4-hydroxyphenyl | -CH₂CH₂N₃ |
| 267 | benzyloxycarbonyl | 4-hydroxyphenyl | -CH₂CH₂NH₂ |

TABLE 5-continued

| Compound | A¹ | A² | E¹ |
|---|---|---|---|
| 268 | benzyl ester | 4-hydroxyphenyl | -CH₂CH₂CHO |
| 269 | benzyl ester | -CH₂COOH | -CH₂C≡CH |
| 270 | benzyl ester | -CH₂COOH | -CH₂CH₂N₃ |
| 271 | benzyl ester | -CH₂COOH | -CH₂CH₂NH₂ |
| 272 | benzyl ester | -CH₂COOH | -CH₂CH₂CHO |
| 273 | benzyl ester | -CH₂OH | -CH₂C≡CH |
| 274 | benzyl ester | -CH₂OH | -CH₂CH₂N₃ |
| 275 | benzyl ester | -CH₂OH | -CH₂CH₂NH₂ |
| 276 | benzyl ester | -CH₂OH | -CH₂CH₂CHO |
| 277 | benzyl ester | -COOH | -CH₂C≡CH |

TABLE 5-continued

| Compound | A¹ | A² | E¹ |
|---|---|---|---|
| 278 | benzyl ester | COOH | N₃-CH₂CH₂- |
| 279 | benzyl ester | COOH | H₂N-CH₂CH₂- |
| 280 | benzyl ester | COOH | OHC-CH₂CH₂- |
| 281 | phenyl | COOH | HC≡C-CH₂- |
| 282 | phenyl | COOH | N₃-CH₂CH₂- |
| 283 | phenyl | COOH | H₂N-CH₂CH₂- |
| 284 | phenyl | COOH | OHC-CH₂CH₂- |
| 285 | isobutyl | COOH | HC≡C-CH₂- |
| 286 | isobutyl | COOH | N₃-CH₂CH₂- |
| 287 | isobutyl | COOH | H₂N-CH₂CH₂- |
| 288 | isobutyl | COOH | OHC-CH₂CH₂- |
| 289 | isobutyl | 4-hydroxyphenyl | HC≡C-CH₂- |
| 290 | isobutyl | 4-hydroxyphenyl | N₃-CH₂CH₂- |

TABLE 5-continued

| Compound | A¹ | A² | E¹ |
|---|---|---|---|
| 291 | isopropyl | 4-hydroxyphenylmethyl | H₂N-CH₂CH₂- |
| 292 | isopropyl | 4-hydroxyphenylmethyl | OHC-CH₂CH₂- |
| 293 | isopropyl | -CH₂-C(=O)-OH | HC≡C-CH₂- |
| 294 | isopropyl | -CH₂-C(=O)-OH | N₃-CH₂CH₂- |
| 295 | isopropyl | -CH₂-C(=O)-OH | H₂N-CH₂CH₂- |
| 296 | isopropyl | -CH₂-C(=O)-OH | OHC-CH₂CH₂- |
| 297 | isopropyl | -CH₂-OH | HC≡C-CH₂- |
| 298 | isopropyl | -CH₂-OH | N₃-CH₂CH₂- |
| 299 | isopropyl | -CH₂-OH | H₂N-CH₂CH₂- |
| 300 | isopropyl | -CH₂-OH | OHC-CH₂CH₂- |

Table 6 sets forth exemplary compounds of the present invention having the formula:

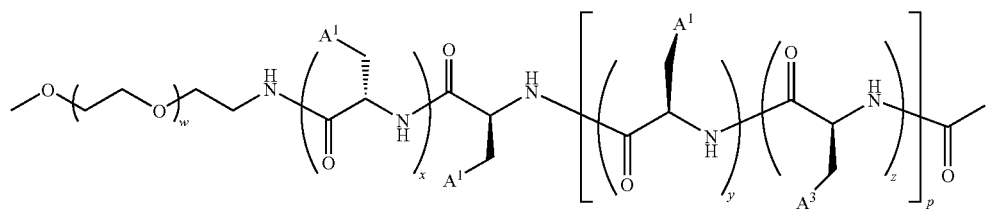

wherein w is 50 to 400, x is 0-30, y is 1-50, z is 1-50, and p is the sum of y and z.

TABLE 6

| Compound | A¹ | A² | A³ |
|---|---|---|---|
| 301 | -COOH | -CH₂C(=O)O-CH₂-C₆H₅ | -COOH |
| 302 | -COOH | -C(=O)O-CH₂-C₆H₅ | -COOH |
| 303 | -COOH | -C₆H₅ | -COOH |
| 304 | -COOH | -CH₂C(=O)O-CH₂-C₆H₅ | -CH₂OH |
| 305 | -COOH | -C(=O)O-CH₂-C₆H₅ | -CH₂OH |
| 306 | -COOH | -C₆H₅ | -CH₂OH |
| 307 | -COOH | -CH₂C(=O)O-CH₂-C₆H₅ | -CH₂COOH |
| 308 | -COOH | -C(=O)O-CH₂-C₆H₅ | -CH₂COOH |
| 309 | -COOH | -C₆H₅ | -CH₂COOH |
| 310 | -COOH | -CH₂C(=O)O-CH₂-C₆H₅ | -C₆H₄-OH |

TABLE 6-continued

| Compound | A¹ | A² | A³ |
|---|---|---|---|
| 311 | -COOH | -C(O)OCH₂Ph | -C₆H₄-OH |
| 312 | -COOH | -Ph | -C₆H₄-OH |
| 313 | -CH₂COOH | -CH₂C(O)OCH₂Ph | -CH₂COOH |
| 314 | -CH₂COOH | -CH₂C(O)OCH₂Ph | -CH₂COOH |
| 315 | -CH₂COOH | -Ph | -CH₂COOH |
| 316 | -CH₂COOH | -CH₂C(O)OCH₂Ph | -OH |
| 317 | -CH₂COOH | -CH₂C(O)OCH₂Ph | -OH |
| 318 | -CH₂COOH | -Ph | -OH |
| 319 | -CH₂COOH | -CH₂C(O)OCH₂Ph | -CH₂COOH |
| 320 | -CH₂COOH | -CH₂C(O)OCH₂Ph | -CH₂COOH |
| 321 | -CH₂COOH | -Ph | -CH₂COOH |

TABLE 6-continued
| Compound | A¹ | A² | A³ |
|---|---|---|---|
| 322 | 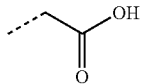 | 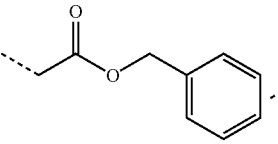 | 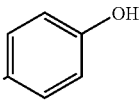 |
| 323 | 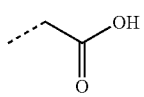 | 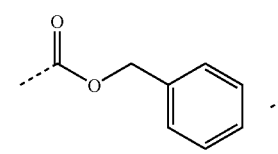 | 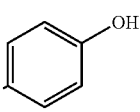 |
| 324 | 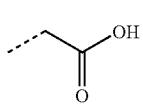 | 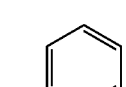 | 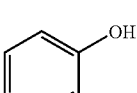 |
| 325 | —SH |  | 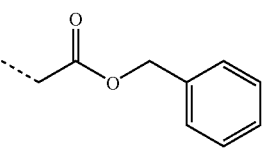 |
| 326 | —SH | 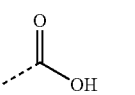 |  |
| 327 | —SH | 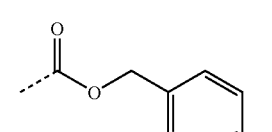 | 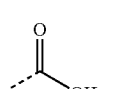 |
| 328 | —SH |  | —OH |
| 329 | —SH | 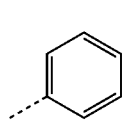 | —OH |
| 330 | —SH | 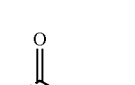 | —OH |
| 331 | —SH |  | 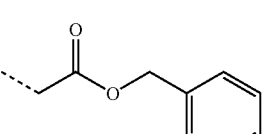 |

TABLE 6-continued

| Compound | A¹ | A² | A³ |
|---|---|---|---|
| 332 | —SH | —C(=O)O—CH₂—C₆H₅ | —CH₂—C(=O)OH |
| 333 | —SH | —C₆H₅ | —CH₂—C(=O)OH |
| 334 | —SH | —CH₂—C(=O)O—CH₂—C₆H₄— | —C₆H₄—OH |
| 335 | —SH | —C(=O)O—CH₂—C₆H₅ | —C₆H₄—OH |
| 336 | —SH | —C₆H₅ | —C₆H₄—OH |
| 337 | 4-imidazolyl | —CH₂—C(=O)O—CH₂—C₆H₅ | —CH₂—C(=O)OH |
| 338 | 4-imidazolyl | —C(=O)O—CH₂—C₆H₅ | —CH₂—C(=O)OH |
| 339 | 4-imidazolyl | —C₆H₅ | —CH₂—C(=O)OH |
| 340 | 4-imidazolyl | —CH₂—C(=O)O—CH₂—C₆H₅ | —OH |
| 341 | 4-imidazolyl | —C(=O)O—CH₂—C₆H₅ | —OH |
| 342 | 4-imidazolyl | —C₆H₅ | —OH |

TABLE 6-continued

| Compound | A¹ | A² | A³ |
|---|---|---|---|
| 343 | imidazole | benzyl propanoate ester | acetic acid |
| 344 | imidazole | benzyl ester | acetic acid |
| 345 | imidazole | phenyl | acetic acid |
| 346 | imidazole | benzyl propanoate ester | 4-hydroxyphenyl |
| 347 | imidazole | benzyl ester | 4-hydroxyphenyl |
| 348 | imidazole | phenyl | 4-hydroxyphenyl |
| 349 | acetic acid | isopropyl | acetic acid |
| 350 | acetic acid | isopropyl | acetic acid |
| 351 | SH | isopropyl | acetic acid |
| 352 | imidazole | isopropyl | acetic acid |
| 353 | 2-ethyl-benzimidazole | isopropyl | acetic acid |
| 354 | acetic acid | isopropyl | 4-hydroxyphenyl |

TABLE 6-continued

| Compound | A¹ | A² | A³ |
|---|---|---|---|
| 355 | -CH₂-C(=O)-OH | isopropyl | 4-hydroxyphenyl |
| 356 | -SH | isopropyl | 4-hydroxyphenyl |
| 357 | 1H-imidazol-4-yl | isopropyl | 4-hydroxyphenyl |
| 358 | 1H-benzimidazol-2-yl-methyl | isopropyl | 4-hydroxyphenyl |
| 359 | -C(=O)-OH | isopropyl | -CH₂-C(=O)-OH |
| 360 | -CH₂-C(=O)-OH | isopropyl | -CH₂-C(=O)-OH |
| 361 | -SH | isopropyl | -CH₂-C(=O)-OH |
| 362 | 1H-imidazol-4-yl | isopropyl | -CH₂-C(=O)-OH |
| 363 | 1H-benzimidazol-2-yl-methyl | isopropyl | -CH₂-C(=O)-OH |
| 364 | -C(=O)-OH | isopropyl | -OH |
| 365 | -CH₂-C(=O)-OH | isopropyl | -OH |
| 366 | -SH | isopropyl | -OH |
| 367 | 1H-imidazol-4-yl | isopropyl | -OH |
| 368 | 1H-benzimidazol-2-yl-methyl | isopropyl | -OH |

TABLE 6-continued

| Compound | A¹ | A² | A³ |
| --- | --- | --- | --- |
| 369 | benzimidazol-2-yl | -CH₂C(O)OCH₂Ph | -C(O)OH |
| 370 | benzimidazol-2-yl | -C(O)OCH₂Ph | -C(O)OH |
| 371 | benzimidazol-2-yl | phenyl | -C(O)OH |
| 372 | benzimidazol-2-yl | -CH₂C(O)OCH₂Ph | -OH |
| 373 | benzimidazol-2-yl | -C(O)OCH₂Ph | -OH |
| 374 | benzimidazol-2-yl | phenyl | -OH |
| 375 | benzimidazol-2-yl | -CH₂C(O)OCH₂Ph | -CH₂C(O)OH |
| 376 | benzimidazol-2-yl | -C(O)OCH₂Ph | -CH₂C(O)OH |
| 377 | benzimidazol-2-yl | phenyl | -CH₂C(O)OH |
| 378 | benzimidazol-2-yl | -CH₂C(O)OCH₂(C₆H₄)- | 4-hydroxyphenyl |

TABLE 6-continued

| Compound | A¹ | A² | A³ |
|---|---|---|---|
| 379 | benzimidazole-CH₂- | -C(O)O-CH₂-phenyl | -phenyl-OH |
| 380 | benzimidazole-CH₂- | -phenyl | -phenyl-OH |

In certain embodiments, the present invention provides a micelle comprising a multiblock copolymer of formula I, wherein m is 0 thus forming a compound of formula I-a:

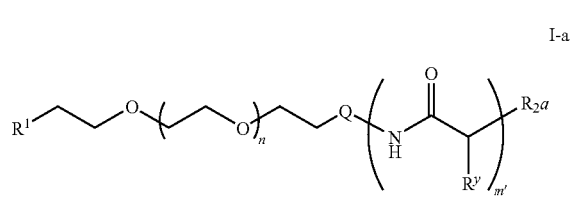

I-a wherein:

n is 10-2500;

m' is 2 to 1000;

$R^y$ forms a hydrophobic D,L-mixed poly(amino acid) block;

$R^1$ is —Z(CH₂CH₂Y)$_p$(CH₂)$_t$R³, wherein:
  Z is —O—, —S—, —C≡C—, or —CH₂—;
  each Y is independently —O— or —S—;
  p is 0-10;
  t is 0-10; and $R^3$ is hydrogen, —N₃, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched C₁₋₁₂ hydrocarbon chain, wherein 0-6 methylene units of Q are independently replaced by -Cy-, —O—, —NH—, —S—, —OC(O)—, —C(O)O—, —C(O)—, —SO—, —SO₂—, —NHSO₂—, —SO₂NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N(R⁴)₂, —NR⁴C(O)R⁴, —NR⁴C(O)N(R⁴)₂, —NR⁴C(O)OR⁴, or —NR⁴SO₂R⁴; and each R⁴ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:

two R⁴ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur, wherein each of R¹, n, m', $R^y$, and $R^{2a}$, is as described herein singly and in combination.

According to another embodiment, the present invention provides compounds of formula I-a, as described above, wherein said compounds have a polydispersity index ("PDI") of about 1.0 to about 1.2. According to another embodiment, the present invention provides compounds of formula I-a, as described above, wherein said compound has a polydispersity index ("PDI") of about 1.03 to about 1.15. According to yet another embodiment, the present invention provides compounds of formula I-a, as described above, wherein said compound has a polydispersity index ("PDI") of about 1.10 to about 1.20. According to other embodiments, the present invention provides compounds of formula I-a having a PDI of less than about 1.10.

Table 7 sets forth exemplary compounds of the present invention having the formula:

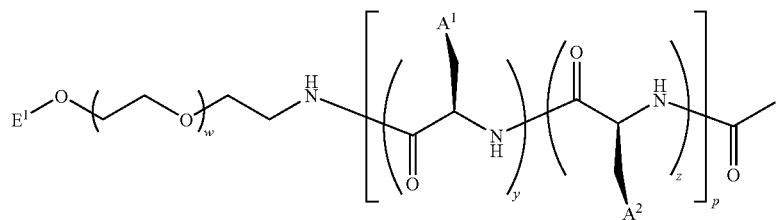

wherein w is 50 to 400, y is 1-50, z is 1-50, and p is the sum of y and z.

TABLE 7

| Compound | E¹ | A¹ | A² |
|---|---|---|---|
| 381 | H₃C— | isopropyl | 4-hydroxyphenyl |
| 382 | HC≡C–CH₂– | isopropyl | 4-hydroxyphenyl |
| 383 | H₂N–CH₂CH₂– | isopropyl | 4-hydroxyphenyl |
| 384 | N₃–CH₂CH₂– | isopropyl | 4-hydroxyphenyl |
| 385 | OHC–CH₂CH₂– | isopropyl | 4-hydroxyphenyl |
| 386 | H– | isopropyl | 4-hydroxyphenyl |
| 387 | HS–CH₂CH₂– | isopropyl | 4-hydroxyphenyl |
| 388 | H₃C— | isopropyl | –CH₂–COOH |
| 381 | HC≡C–CH₂– | isopropyl | –CH₂–COOH |
| 382 | H₂N–CH₂CH₂– | isopropyl | –CH₂–COOH |

TABLE 7-continued

| Compound | E¹ | A¹ | A² |
|---|---|---|---|
| 383 | N₃-CH₂CH₂- | -CH(CH₃)₂ | -COOH |
| 384 | OHC-CH₂CH₂- | -CH(CH₃)₂ | -COOH |
| 385 | -H | -CH(CH₃)₂ | -COOH |
| 386 | HS-CH₂CH₂- | -CH(CH₃)₂ | -COOH |
| 387 | H₃C- | -CH(CH₃)₂ | -OH |
| 388 | HC≡C-CH₂- | -CH(CH₃)₂ | -OH |
| 389 | H₂N-CH₂CH₂- | -CH(CH₃)₂ | -OH |
| 390 | N₃-CH₂CH₂- | -CH(CH₃)₂ | -OH |
| 391 | OHC-CH₂CH₂- | -CH(CH₃)₂ | -OH |
| 392 | -H | -CH(CH₃)₂ | -OH |
| 393 | HS-CH₂CH₂- | -CH(CH₃)₂ | -OH |
| 394 | H₃C- | -CH(CH₃)₂ | -CH₂COOH |
| 395 | HC≡C-CH₂- | -CH(CH₃)₂ | -CH₂COOH |
| 396 | H₂N-CH₂CH₂- | -CH(CH₃)₂ | -CH₂COOH |
| 397 | N₃-CH₂CH₂- | -CH(CH₃)₂ | -CH₂COOH |
| 398 | OHC-CH₂CH₂- | -CH(CH₃)₂ | -CH₂COOH |

TABLE 7-continued

| Compound | E¹ | A¹ | A² |
|---|---|---|---|
| 399 | H | isobutyl | CH₂COOH |
| 400 | HS-CH₂CH₂- | isobutyl | CH₂COOH |
| 401 | H₃C- | phenyl | 4-hydroxyphenyl |
| 402 | HC≡C-CH₂- | phenyl | 4-hydroxyphenyl |
| 403 | H₂N-CH₂CH₂- | phenyl | 4-hydroxyphenyl |
| 404 | N₃-CH₂CH₂- | phenyl | 4-hydroxyphenyl |
| 405 | OHC-CH₂CH₂- | phenyl | 4-hydroxyphenyl |
| 406 | H | phenyl | 4-hydroxyphenyl |
| 407 | HS-CH₂CH₂- | phenyl | 4-hydroxyphenyl |
| 408 | H₃C- | phenyl | COOH |
| 409 | HC≡C-CH₂- | phenyl | COOH |
| 410 | H₂N-CH₂CH₂- | phenyl | COOH |
| 411 | N₃-CH₂CH₂- | phenyl | COOH |
| 412 | OHC-CH₂CH₂- | phenyl | COOH |

TABLE 7-continued

| Compound | E¹ | A¹ | A² |
|---|---|---|---|
| 413 | H | phenyl | -C(=O)OH |
| 414 | HS-CH₂CH₂- | phenyl | -C(=O)OH |
| 415 | H₃C- | phenyl | -OH |
| 416 | HC≡C-CH₂- | phenyl | -OH |
| 417 | H₂N-CH₂CH₂- | phenyl | -OH |
| 418 | N₃-CH₂CH₂- | phenyl | -OH |
| 419 | OHC-CH₂CH₂- | phenyl | -OH |
| 420 | H | phenyl | -OH |
| 421 | HS-CH₂CH₂- | phenyl | -OH |
| 422 | H₃C- | phenyl | -CH₂C(=O)OH |
| 423 | HC≡C-CH₂- | phenyl | -CH₂C(=O)OH |
| 424 | H₂N-CH₂CH₂- | phenyl | -CH₂C(=O)OH |
| 425 | N₃-CH₂CH₂- | phenyl | -CH₂C(=O)OH |
| 426 | OHC-CH₂CH₂- | phenyl | -CH₂C(=O)OH |

TABLE 7-continued

| Compound | E¹ | A¹ | A² |
|---|---|---|---|
| 427 | H | phenyl | CH₂C(O)OH |
| 428 | HS-CH₂CH₂- | phenyl | CH₂C(O)OH |
| 429 | H₃C- | -C(O)O-CH₂-phenyl- | -phenyl-OH (4-) |
| 430 | HC≡C-CH₂- | -C(O)O-CH₂-phenyl- | -phenyl-OH (4-) |
| 431 | H₂N-CH₂CH₂- | -C(O)O-CH₂-phenyl- | -phenyl-OH (4-) |
| 432 | N₃-CH₂CH₂- | -C(O)O-CH₂-phenyl- | -phenyl-OH (4-) |
| 433 | OHC-CH₂CH₂- | -C(O)O-CH₂-phenyl- | -phenyl-OH (4-) |
| 434 | H | -C(O)O-CH₂-phenyl- | -phenyl-OH (4-) |
| 435 | HS-CH₂CH₂- | -C(O)O-CH₂-phenyl- | -phenyl-OH (4-) |
| 436 | H₃C- | -C(O)O-CH₂-phenyl- | C(O)OH |

TABLE 7-continued

| Compound | E¹ | A¹ | A² |
|---|---|---|---|
| 437 | HC≡C-CH₂- | -C(=O)-O-CH₂-C₆H₅ | -C(=O)-OH |
| 438 | H₂N-CH₂-CH₂- | -C(=O)-O-CH₂-C₆H₅ | -C(=O)-OH |
| 439 | N₃-CH₂-CH₂- | -C(=O)-O-CH₂-C₆H₅ | -C(=O)-OH |
| 440 | OHC-CH₂-CH₂- | -C(=O)-O-CH₂-C₆H₅ | -C(=O)-OH |
| 441 | -H | -C(=O)-O-CH₂-C₆H₅ | -C(=O)-OH |
| 442 | HS-CH₂-CH₂- | -C(=O)-O-CH₂-C₆H₅ | -C(=O)-OH |
| 443 | H₃C- | -C(=O)-O-CH₂-C₆H₅ | -OH |
| 444 | HC≡C-CH₂- | -C(=O)-O-CH₂-C₆H₅ | -OH |
| 445 | H₂N-CH₂-CH₂- | -C(=O)-O-CH₂-C₆H₅ | -OH |
| 446 | N₃-CH₂-CH₂- | -C(=O)-O-CH₂-C₆H₅ | -OH |

TABLE 7-continued

| Compound | E¹ | A¹ | A² |
|---|---|---|---|
| 447 | OHC-CH₂-CH₂- | -C(=O)O-CH₂-C₆H₅ (benzyl ester) | -CH₂-OH |
| 448 | -H | -C(=O)O-CH₂-C₆H₅ | -CH₂-OH |
| 449 | HS-CH₂-CH₂- | -C(=O)O-CH₂-C₆H₅ | -CH₂-OH |
| 450 | H₃C- | -C(=O)O-CH₂-C₆H₅ | -CH₂-C(=O)OH |
| 451 | HC≡C-CH₂- | -C(=O)O-CH₂-C₆H₅ | -CH₂-C(=O)OH |
| 452 | H₂N-CH₂-CH₂- | -C(=O)O-CH₂-C₆H₅ | -CH₂-C(=O)OH |
| 453 | N₃-CH₂-CH₂- | -C(=O)O-CH₂-C₆H₅ | -CH₂-C(=O)OH |
| 454 | OHC-CH₂-CH₂- | -C(=O)O-CH₂-C₆H₅ | -CH₂-C(=O)OH |
| 455 | -H | -C(=O)O-CH₂-C₆H₅ | -CH₂-C(=O)OH |

TABLE 7-continued

| Compound | E¹ | A¹ | A² |
|---|---|---|---|
| 456 | HS−CH₂CH₂− | −CH₂C(O)O−CH₂−C₆H₅ | −CH₂C(O)OH |
| 457 | H₃C− | −CH₂C(O)O−CH₂−C₆H₄− | −C₆H₄−OH |
| 458 | HC≡C−CH₂− | −CH₂C(O)O−CH₂−C₆H₄− | −C₆H₄−OH |
| 459 | H₂N−CH₂CH₂− | −CH₂C(O)O−CH₂−C₆H₄− | −C₆H₄−OH |
| 460 | N₃−CH₂CH₂− | −CH₂C(O)O−CH₂−C₆H₄− | −C₆H₄−OH |
| 461 | OHC−CH₂− | −CH₂C(O)O−CH₂−C₆H₄− | −C₆H₄−OH |
| 462 | −H | −CH₂C(O)O−CH₂−C₆H₄− | −C₆H₄−OH |
| 463 | HS−CH₂CH₂− | −CH₂C(O)O−CH₂−C₆H₄− | −C₆H₄−OH |
| 464 | H₃C− | −CH₂C(O)O−CH₂−C₆H₅ | −C(O)OH |
| 465 | HC≡C−CH₂− | −CH₂C(O)O−CH₂−C₆H₅ | −C(O)OH |

TABLE 7-continued

| Compound | E¹ | A¹ | A² |
|---|---|---|---|
| 466 | H₂N–CH₂CH₂– | –CH₂C(=O)O–CH₂–C₆H₅ | –C(=O)OH |
| 467 | N₃–CH₂CH₂– | –CH₂C(=O)O–CH₂–C₆H₅ | –C(=O)OH |
| 468 | H(C=O)–CH₂CH₂– | –CH₂C(=O)O–CH₂–C₆H₅ | –C(=O)OH |
| 469 | –H | –CH₂C(=O)O–CH₂–C₆H₅ | –C(=O)OH |
| 470 | HS–CH₂CH₂– | –CH₂C(=O)O–CH₂–C₆H₅ | –C(=O)OH |
| 471 | H₃C– | –CH₂C(=O)O–CH₂–C₆H₅ | –OH |
| 472 | HC≡C–CH₂– | –CH₂C(=O)O–CH₂–C₆H₅ | –OH |
| 473 | H₂N–CH₂CH₂– | –CH₂C(=O)O–CH₂–C₆H₅ | –OH |
| 474 | N₃–CH₂CH₂– | –CH₂C(=O)O–CH₂–C₆H₅ | –OH |

TABLE 7-continued

| Compound | E¹ | A¹ | A² |
|---|---|---|---|
| 475 | OHC-CH₂-CH₂- | -CH₂-C(=O)-O-CH₂-C₆H₅ | -CH₂-OH |
| 476 | -H | -CH₂-C(=O)-O-CH₂-C₆H₅ | -CH₂-OH |
| 477 | HS-CH₂-CH₂- | -CH₂-C(=O)-O-CH₂-C₆H₅ | -CH₂-OH |
| 478 | H₃C- | -CH₂-C(=O)-O-CH₂-C₆H₅ | -CH₂-C(=O)OH |
| 479 | HC≡C-CH₂- | -CH₂-C(=O)-O-CH₂-C₆H₅ | -CH₂-C(=O)OH |
| 480 | H₂N-CH₂-CH₂- | -CH₂-C(=O)-O-CH₂-C₆H₅ | -CH₂-C(=O)OH |
| 481 | N₃-CH₂-CH₂- | -CH₂-C(=O)-O-CH₂-C₆H₅ | -CH₂-C(=O)OH |
| 482 | OHC-CH₂-CH₂- | -CH₂-C(=O)-O-CH₂-C₆H₅ | -CH₂-C(=O)OH |
| 483 | -H | -CH₂-C(=O)-O-CH₂-C₆H₅ | -CH₂-C(=O)OH |
| 484 | HS-CH₂-CH₂- | -CH₂-C(=O)-O-CH₂-C₆H₅ | -CH₂-C(=O)OH |

In other embodiments, the present invention provides a micelle comprising a multiblock copolymer of formula II:

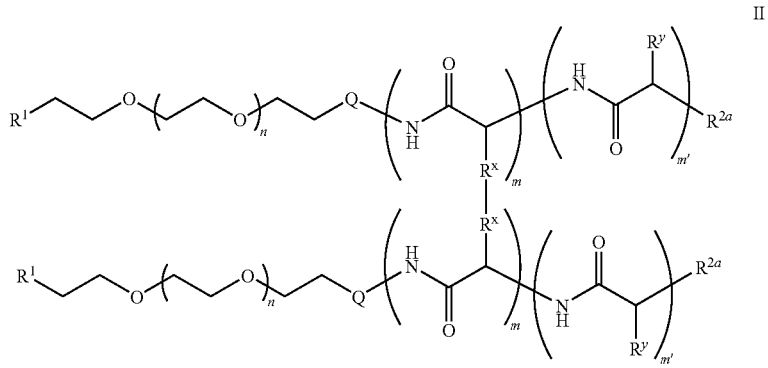

wherein:

n is 10-2500;

m is 1 to 1000;

m' is 2 to 1000;

$R^x$ is a crosslinked natural or unnatural amino acid side-chain group;

$R^y$ forms a hydrophobic D,L-mixed poly(amino acid) block;

$R^1$ is $-Z(CH_2CH_2Y)_p(CH_2)_tR^3$, wherein:
Z is $-O-$, $-S-$, $-C{\equiv}C-$, or $-CH_2-$;
each Y is independently $-O-$ or $-S-$;
p is 0-10;
t is 0-10; and $R^3$ is $-N_3$, $-CN$, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched $C_{1-12}$ hydrocarbon chain, wherein 0-6 methylene units of Q are independently replaced by -Cy-, $-O-$, $-NH-$, $-S-$, $-OC(O)-$, $-C(O)O-$, $-C(O)-$, $-SO-$, $-SO_2-$, $-NHSO_2-$, $-SO_2NH-$, $-NHC(O)-$, $-C(O)NH-$, $-OC(O)NH-$, or $-NHC(O)O-$, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, $-N(R^4)_2$, $-NR^4C(O)R^4$, $-NR^4C(O)N(R^4)_2$, $-NR^4C(O)OR^4$, or $-NR^4SO_2R^4$; and each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur, wherein each of $R^1$, n, m, m', $R^x$, $R^y$, and $R^{2a}$, is as described herein singly and in combination.

According to another embodiment, the present invention provides compounds of formula II, as described above, wherein said compounds have a polydispersity index ("PDI") of about 1.0 to about 1.2. According to another embodiment, the present invention provides compounds of formula II, as described above, wherein said compound has a polydispersity index ("PDI") of about 1.03 to about 1.15. According to yet another embodiment, the present invention provides compounds of formula II, as described above, wherein said compound has a polydispersity index ("PDI") of about 1.10 to about 1.20. According to other embodiments, the present invention provides compounds of formula II having a PDI of less than about 1.10.

In certain embodiments, the present invention provides a compound selected from:

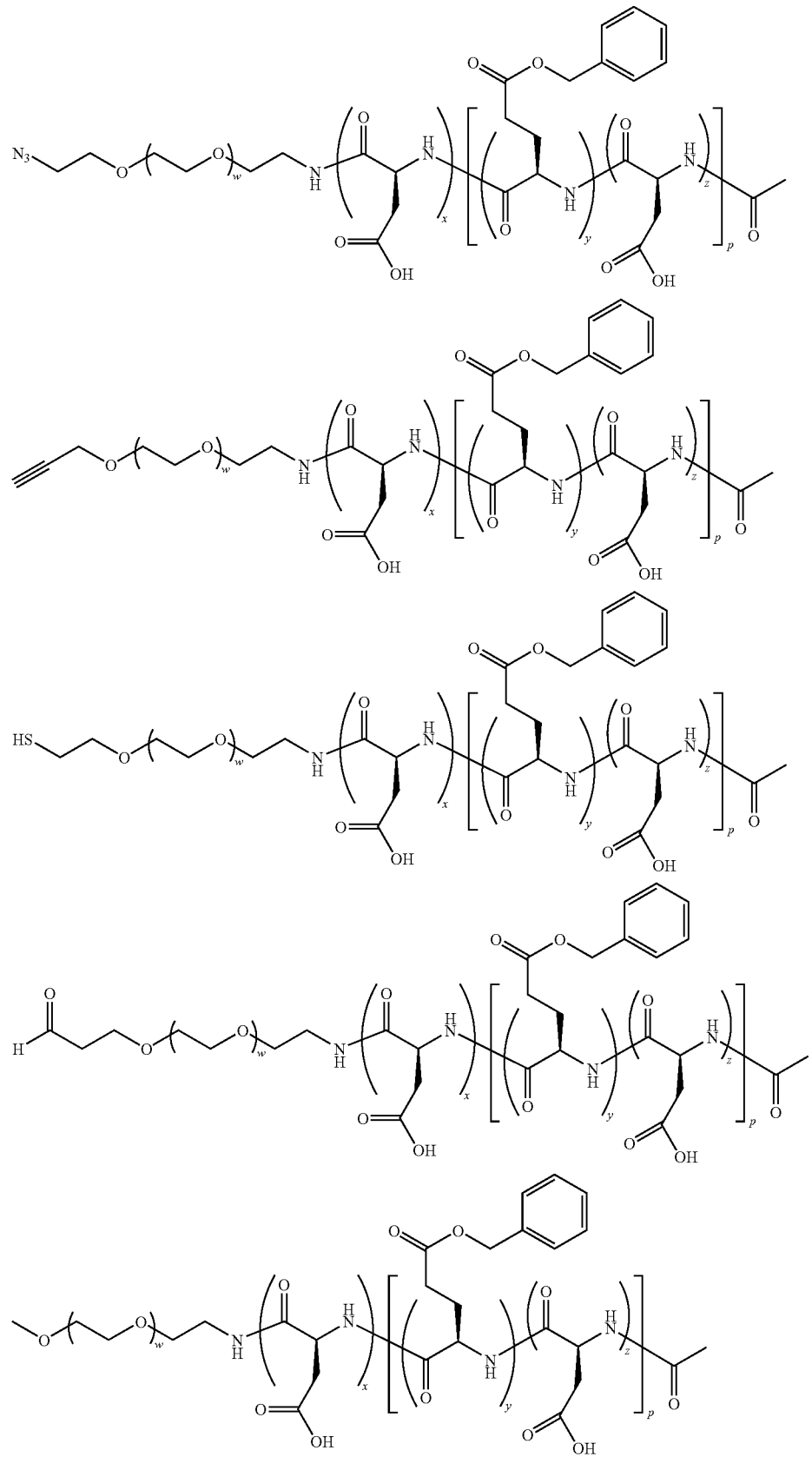

wherein each w is independently, 50 to 400, each x is independently, 0-30, each y is independently 1-50, each z is independently 1-50, and each p is the sum of y and z.

In certain embodiments, the present invention provides a compound selected from:

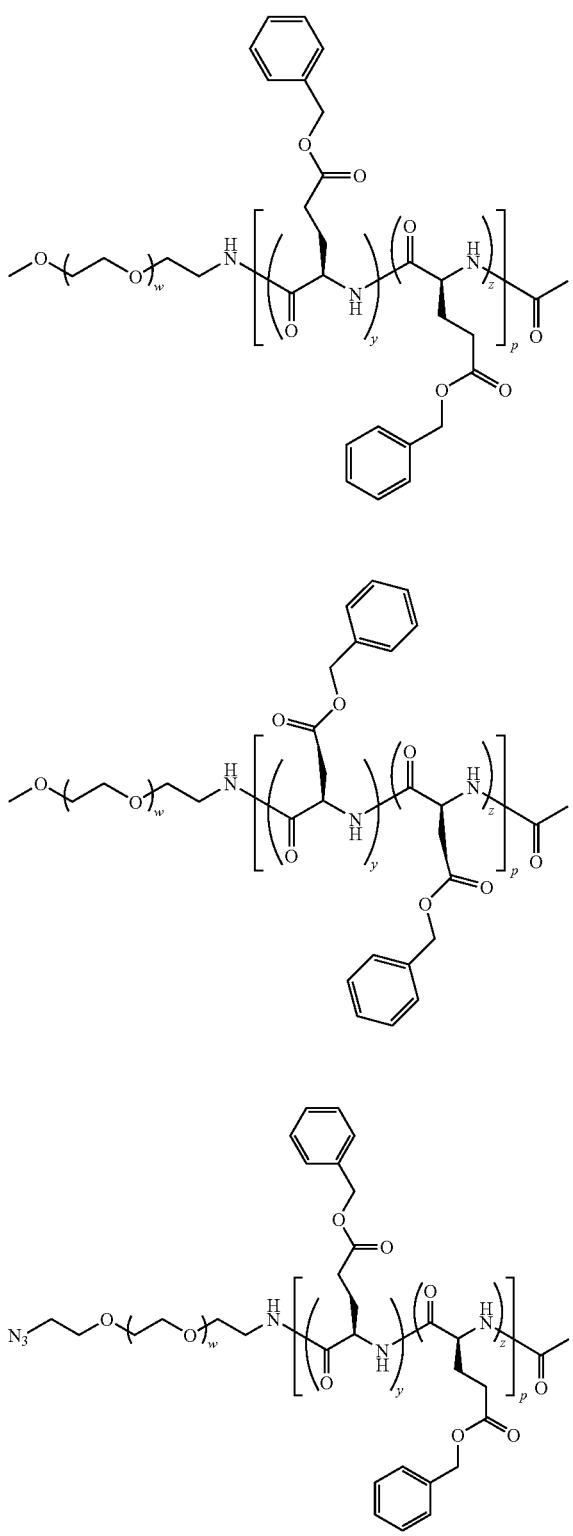

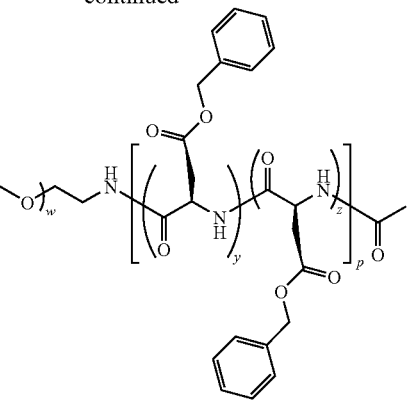

-continued

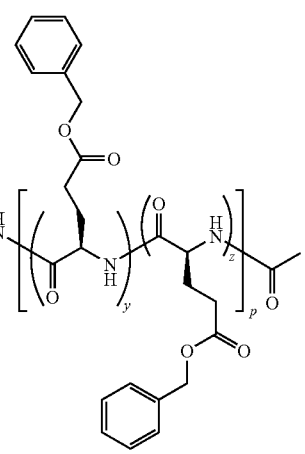

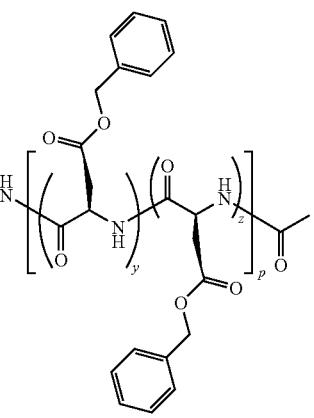

wherein each w is independently, 50 to 400, each y is independently 1-50, each z is independently 1-50, and each p is the sum of y and z.

B. Crosslinking Chemistries

In certain embodiments, the present invention provides crosslinked micelles which effectively encapsulate hydrophobic or ionic therapeutic agents at pH 7.4 (blood) but dissociate and release the drug at targeted, acidic pH values ranging from 5.0 (endosomal pH) to 6.8 (extracellular tumor pH). In yet other embodiments, the pH value can be adjusted between 4.0 and 7.4. These pH-targeted nanovectors will dramatically improve the cancer-specific delivery of chemotherapeutic agents and minimize the harmful side effects commonly encountered with potent chemotherapy drugs. In addition, the utilization of chemistries which can be tailored to dissociate across a range of pH values make these drug-loaded micelles applicable in treating solid tumors and malignancies that have become drug resistant.

In certain embodiments, micelles of the present invention comprise a crosslinked multiblock polymer of formula III:

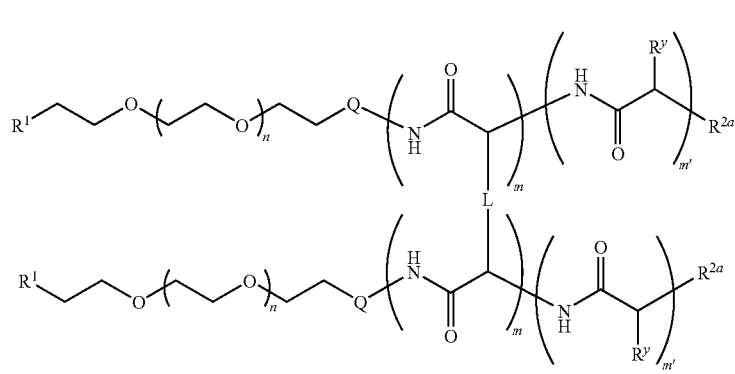

III wherein:
n is 10-2500;
m is 1 to 1000;
m' is 2 to 1000;
L is a bivalent, saturated or unsaturated, straight or branched $C_{1-12}$ hydrocarbon chain, wherein 0-6 methylene units of L are independently replaced by -M-, -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-M- is a suitable bivalent metal;
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^y$ forms a hydrophobic D,L-mixed poly(amino acid) block;
$R^1$ is —Z(CH$_2$CH$_2$Y)$_p$(CH$_2$)$_t$R$^3$, wherein:
Z is —O—, —S—, —C≡C—, or —CH$_2$—;
each Y is independently —O— or —S—;
p is 0-10;
t is 0-10; and
$R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
Q is a valence bond or a bivalent, saturated or unsaturated, straight or branched $C_{1-12}$ alkylene chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and
each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur, wherein each of $R^1$, n, m, m', $R^y$, and $R^{2a}$, is as described in classes and subclasses herein singly and in combination.

According to another embodiment, the present invention provides compounds of formula III, as described above, wherein said compounds have a polydispersity index ("PDI") of about 1.0 to about 1.2. According to another embodiment, the present invention provides compounds of formula III, as described above, wherein said compound has a polydispersity index ("PDI") of about 1.03 to about 1.15. According to yet another embodiment, the present invention provides compounds of formula I, as described above, wherein said compound has a polydispersity index ("PDI") of about 1.10 to about 1.20. According to other embodiments, the present invention provides compounds of formula III having a PDI of less than about 1.10.

As defined generally above, the L group of formula III is a bivalent, saturated or unsaturated, straight or branched $C_{1-12}$ hydrocarbon chain, wherein 0-6 methylene units of L are independently replaced by -M-, Cy, —O—, NH—, —S—, —C(O)—, —SO—, —SO2-, NHC(O)—, C(O)NH—, OC(O)NH—, or —NHC(O)O—, wherein -M- is a suitable bivalent metal, and -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. It will be appreciated that the L group of formula III represents crosslinked amino acid side-chain groups. In certain embodiments, the crosslinked amino acid side-chain groups correspond to the $R^x$ moiety of compounds of formulae I and II as described herein. In certain embodiments, the L group of formula III represents a metal crosslinked amino acid side-chain group, a hydrazone crosslinked amino acid side-chain group, an ester crosslinked amino acid side-chain group, an amide crosslinked side-chain group, an imine (e.g. Schiff base) crosslinked side-chain group, or a disulfide crosslinked side-chain group.

In certain embodiments, the L group of formula III comprises -M-. In other embodiments, -M- is zinc, calcium, iron or aluminum. In yet other embodiments, -M- is strontium, manganese, palladium, silver, gold, cadmium, chromium, indium, or lead.

In other embodiments, the L group of formula III is a bivalent, saturated or unsaturated, straight or branched $C_{1-12}$ hydrocarbon chain wherein 2 methylene units of L are independently replaced by —C(O)—, —C(O)NH—, —NHC(O)—, —S—, —C(O)O—, —OC(O)—, —C(O)NHN—, —=NNHC(O)—, —=N—, —N=—, -M-OC(O)—, or —C(O)O-M-. According to another embodiment, the L group of formula III is a bivalent, saturated or unsaturated, straight or branched $C_{1-6}$ hydrocarbon chain, wherein two methylene units of L are replaced by —C(O)— or —C(O)NH—. In other embodiments, the L group of formula III is a bivalent, saturated or unsaturated, straight or branched $C_{1-12}$ hydrocarbon chain having at least 2 units of unsaturation. According to yet another embodiment, the L group of formula III is a bivalent, saturated or unsaturated, straight or branched $C_{1-12}$ alkylene chain wherein two methylene units of L are replaced by —NH—. According to yet another embodiment, the L group of formula III is a bivalent, saturated or unsaturated, straight or branched $C_{1-12}$ alkylene chain wherein two methylene units of L are replaced by —C(O)NHN.

In certain embodiments, the -M- moiety of the L group of formula III is zinc. In other embodiments, L forms a zinc-dicarboxylate crosslinking moiety. In certain embodiments, the crosslinking utilizes zinc-mediated coupling of carboxylic acids, a highly selective and pH-sensitive reaction that is performed in water. This reaction, which is widely used in cough lozenge applications, involves the association of zinc ions with carboxylic acids at basic pH. See Bakar, N. K. A.; Taylor, D. M.; Williams, D. R. *Chem. Spec. Bioavail.* 1999, 11, 95-101; and Eby, G. A. *J. Antimicrob. Chemo.* 1997, 40, 483-493. These zinc-carboxylate bonds readily dissociate in the presence of acid.

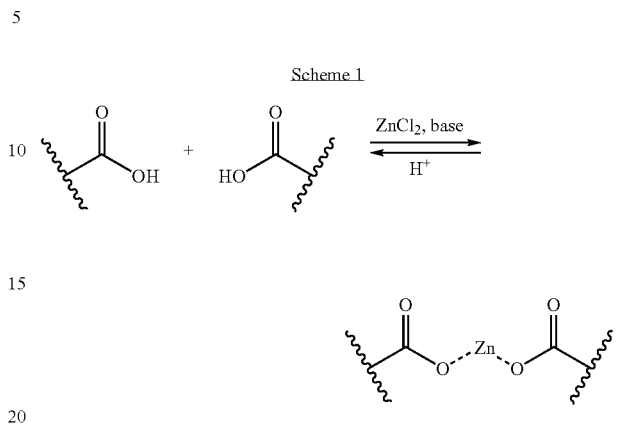

Scheme 1

Scheme 1 above illustrates the reaction of an aqueous zinc ion (e.g. from zinc chloride) with two equivalents of an appropriate carboxylic acid to form the zinc dicarboxylate. This reaction occurs rapidly and irreversibly in a slightly basic pH environment but upon acidification, is reversible within a tunable range of pH 4.0-6.8 to reform $ZnX_2$, where X is the conjugate base. One of ordinary skill in the art will recognize that a variety of natural and unnatural amino acid side-chains have a carboxylic acid moeity that can be crosslinked by zinc or another suitable metal.

In certain embodiments, L represents aspartic acid side-chains crosslinked with zinc. Without wishing to be bound by theory, it is believed that the zinc aspartate crosslinks are stable in the blood compartment (pH 7.4), allowing for effective accumulation of the drug-loaded micelles in solid tumors by passive and active targeting mechanisms. In the presence of lactic acid concentrations commonly encountered in solid tumors or in acidic organelles of cancer cells, rapid degradation of the metal crosslinks leading to micelle dissociation and release of the drug at the tumor site. Preliminary, qualitative studies have shown that crosslinked zinc aspartate segments are reversible in the presence of α-hydroxyacids.

In certain embodiments, the -M- moiety of the L group of formula III is zinc. In some embodiments, L forms a zinc-imidazole crosslinking moiety. In certain embodiments, the crosslinking utilizes zinc-mediated coupling of imidazoles.

Scheme 2

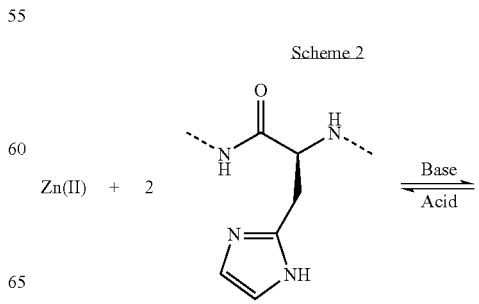

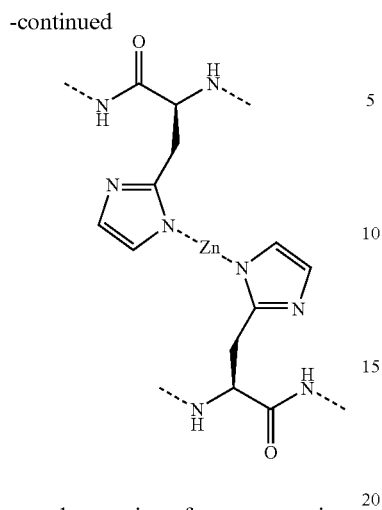

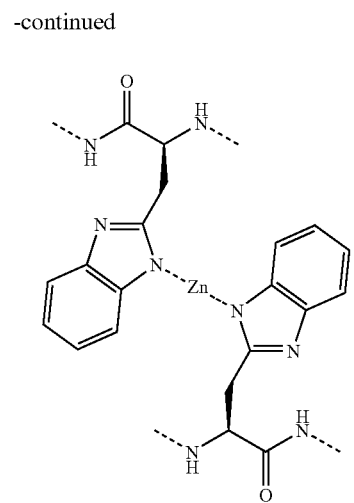

Scheme 2 above illustrates the reaction of an aqueous zinc (II) ion (e.g. from zinc chloride or zinc acetate) with two equivalents of an appropriate imidazole (e.g. histidine) to form a zinc-histidine complex. This reaction occurs rapidly in a slightly basic pH environment and is reversible upon acidification to pH less than 6. (Tezcan, et. al. J. Am. Chem. Soc. 2007, 129, 13347-13375.)

In certain embodiments, $R^x$ is a histidine side-chain crosslinked with zinc. Without wishing to be bound by any particular theory, it is believed that zinc-histidine crosslinks are stable in the blood compartment (pH 7.4), allowing for effective accumulation of therapeutic loaded micelles in solid tumors by passive and/or active targeting mechanisms. In the presence of lactic acid concentrations commonly encountered in solid tumors or hydrochloric acid in acidic organelles of cancer cells, rapid degradation of the metal crosslinks occurs which leads to micelle dissociation and release of the polynucleotide at the tumor site.

Scheme 3 above illustrates the reaction of an aqueous zinc (II) ion (e.g. from zinc chloride or zinc acetate) with two equivalents of an appropriate imidazole (e.g. benzimidazole) to form a zinc-benzimidazole complex.

In certain embodiments, $R^x$ is a benzimidazole side-chain crosslinked with zinc. Without wishing to be bound by any particular theory, it is believed that zinc-benzimidazole crosslinks are stable in the blood compartment (pH 7.4), allowing for effective accumulation of therapeutic loaded micelles in solid tumors by passive and/or active targeting mechanisms. In the presence of lactic acid concentrations commonly encountered in solid tumors or hydrochloric acid in acidic organelles of cancer cells, rapid degradation of the metal crosslinks occurs which leads to micelle dissociation and release of the polynucleotide at the tumor site.

It will be appreciated that such imidazole- and benzimidazole-containing side-chains can be incorporated into a provided multiblock copolymer during preparation of a compound of formula I by virtue of incorporation of the $R^x$ group. Alternatively, such imidazole- and benzimidazole-containing side-chains can be incorporated into said compound of formula I after polymerization, i.e. post-polymerization. Such post-polymerization incorporation of imidazole- and benzimidazole-containing side-chains is depicted in Schemes 4 and 5, below. Other methods of post-polymerization modification will be apparent to one of ordinary skill in the art.

Scheme 3

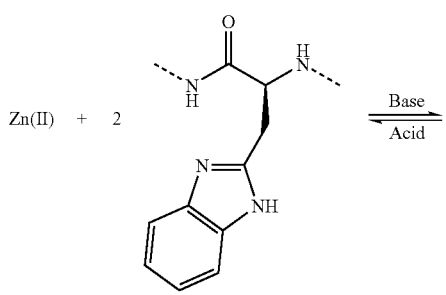

Scheme 4

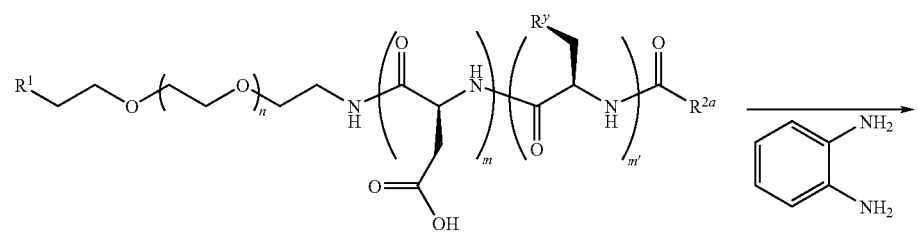

-continued

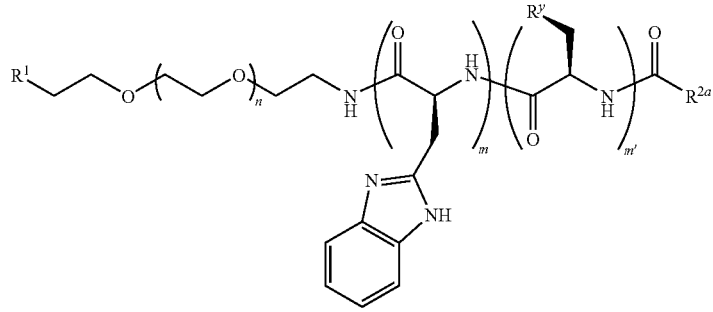

Scheme 5

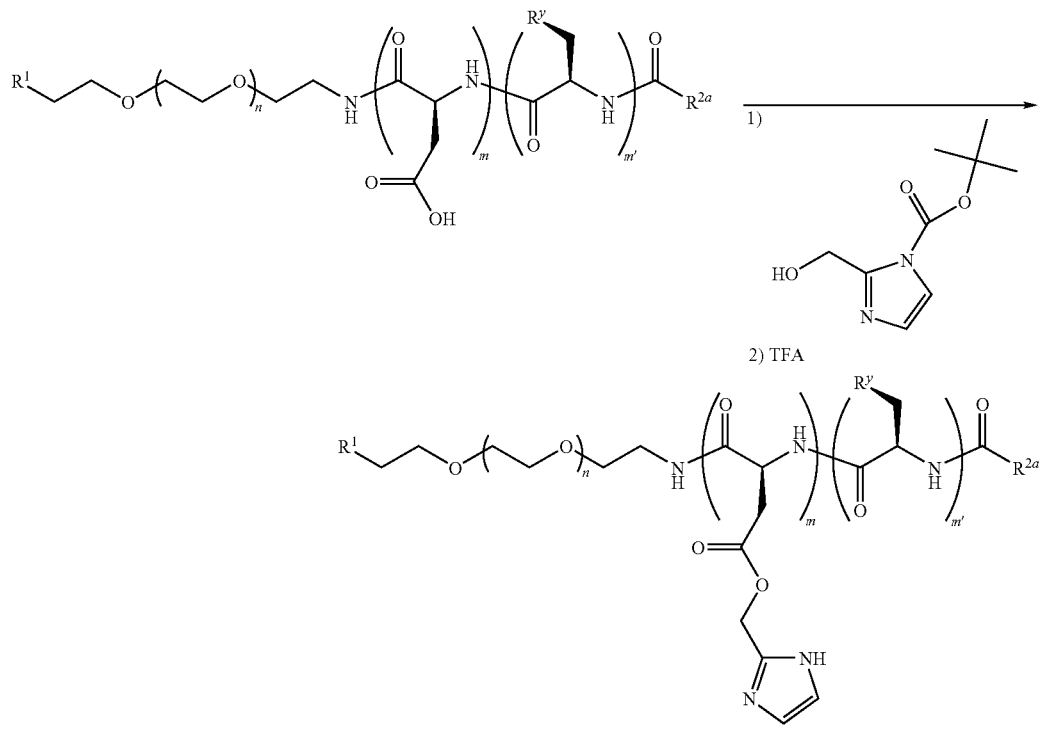

The choice of zinc as a crosslinking metal is advantageous for effective micelle crosslinking. Zinc chloride and the zinc lactate by-product are generally recognized as non-toxic, and other safety concerns are not anticipated. Pharmaceutical grade zinc chloride is commonly used in mouthwash and as a chlorophyll stabilizer in vegetables while zinc lactate is used as an additive in toothpaste and drug preparation. The reaction is reversible within a tunable pH range, selective toward carboxylic acids, and should not alter the encapsulated chemotherapy agents. While zinc has been chosen as an exemplary metal for micelle crosslinking, it should be noted that many other metals undergo acid sensitive coupling with carboxylic acids. These metals include calcium, iron and aluminum, to name but a few. One or more of these metals can be substituted for zinc.

The ultimate goal of metal-mediated crosslinking is to ensure micelle stability when diluted in the blood (pH 7.4) followed by rapid dissolution and drug release in response to a finite pH change such as those found in cancer cells. Previous reports suggest a widely variable and tunable dissociation pH for zinc-acid bonds (from approximately 2.0 to 7.0) depending on the carboxylic acid used and number of bonds formed. See Cannan, R. K.; Kibrick, A. *J. Am. Chem. Soc.* 1938, 60, 2314-2320. Without wishing to be bound by theory, it is believed that the concentration of zinc chloride and the number of aspartic acid, or other carboxylic acid-containing amino acid, repeat units in the crosslinking block will ultimately control the pH at which complete micelle disassembly occurs. The synthetic versatility of the block copolymer design is advantageous since one or more variables are tuned to achieve the desired pH reversibility. By simple adjustment of zinc chloride/polymer stoichiometry, pH-reversible crosslinking is finely tuned across the pH range of interest. For example, higher zinc concentrations yield more zinc crosslinks which require higher acid concentrations (i.e. lower pH) to dissociate. Adjustments in zinc/polymer stoichiometry will yield the desired pH reversibility, however other variables such as increasing the poly(aspartic acid) block length (i.e. 15-25 repeat units) further tune the reversible crosslinking reaction if necessary.

In other embodiments, L comprises a mixture of crosslinked hydrophilic amino acid side-chain groups. Such mixtures of amino acid side-chain groups include those having a carboxylic acid functionality, a hydroxyl functionality, a thiol functionality, and/or amine functionality. It will be appreciated that when L comprises a mixture of crosslinked hydrophilic amino acid side-chain functionalities, then multiple crosslinking can occur. For example, when L comprises a carboxylic acid-containing side-chain (e.g., aspartic acid or glutamic acid) and a thiol-containing side-chain (e.g., cysteine), then the amino acid block can have both zinc crosslinking and cysteine crosslinking (dithiol). This sort of mixed crosslinked block is advantageous for the delivery of therapeutic drugs to the cytosol of diseased cells because a second stimuli must be present to allow for drug release. For example, micelles possessing both carboxylic acid-zinc crosslinking and cysteine dithiol crosslinking would be required to enter an acidic environment (e.g. a tumor) and enter an environment with a high concentration of glutathione (e.g. in the cell cytoplasm). When L comprises an amine-containing side-chain (e.g., lysine or arginine) and a thiol-containing side-chain (e.g., cysteine), then the amino acid block can have both imine (e.g. Schiff base) crosslinking and cysteine crosslinking (dithiol). The zinc and ester crosslinked carboxylic acid functionality and the imine (e.g. Schiff base) crosslinked amine functionality are reversible in acidic organelles (i.e. endosomes, lysosome) while disulfides are reduced in the cytosol by glutathione or other reducing agents resulting in drug release exclusively in the cytoplasm.

Exemplary $R^1$ groups of any of formulae I, I-a, II, and III are set forth in Table 8, below.

TABLE 8

Representative $R^1$ Groups

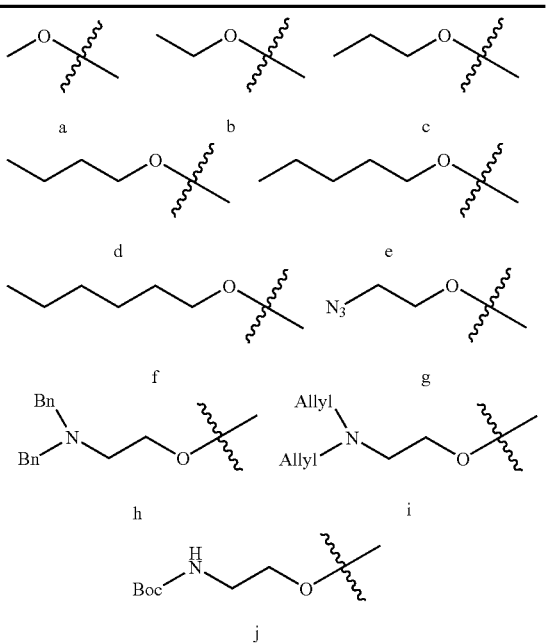

TABLE 8-continued

Representative $R^1$ Groups

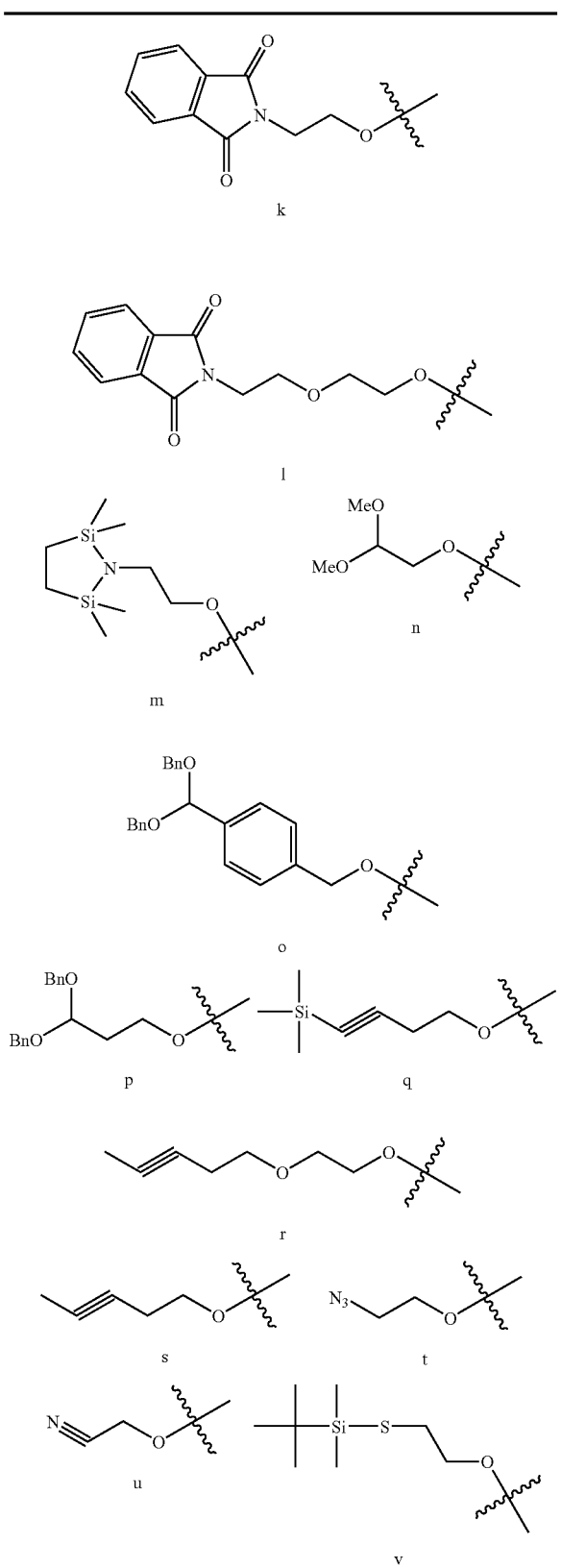

TABLE 8-continued
Representative R¹ Groups
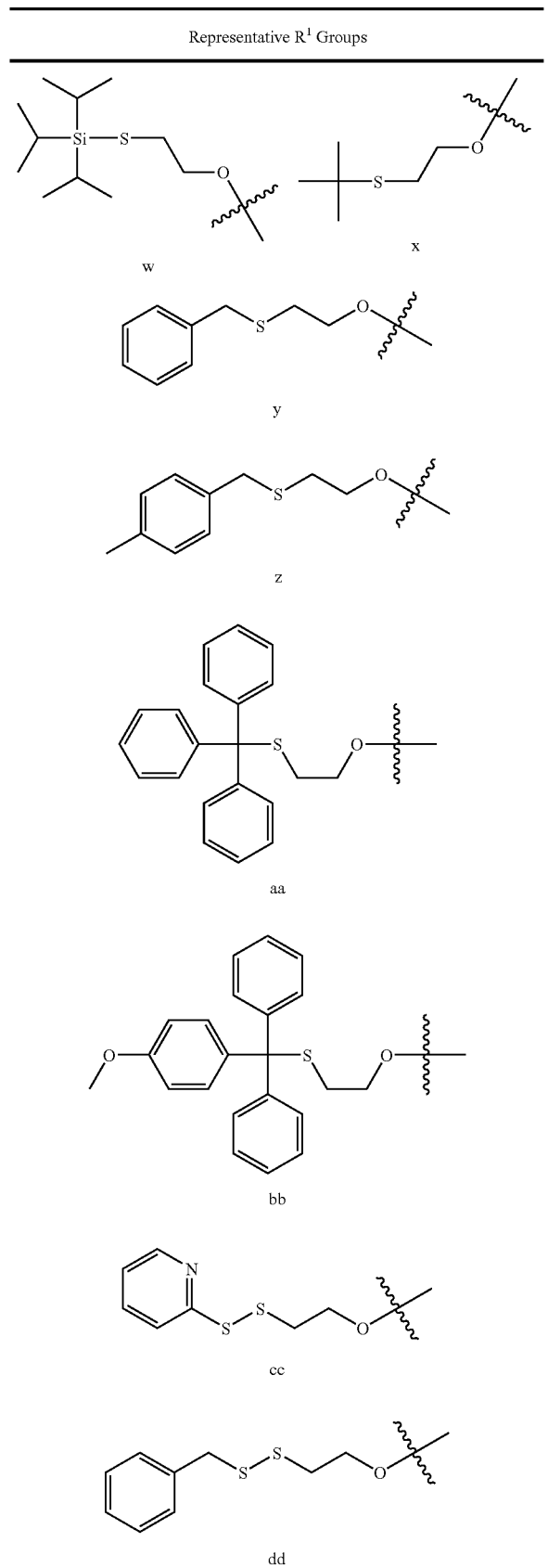
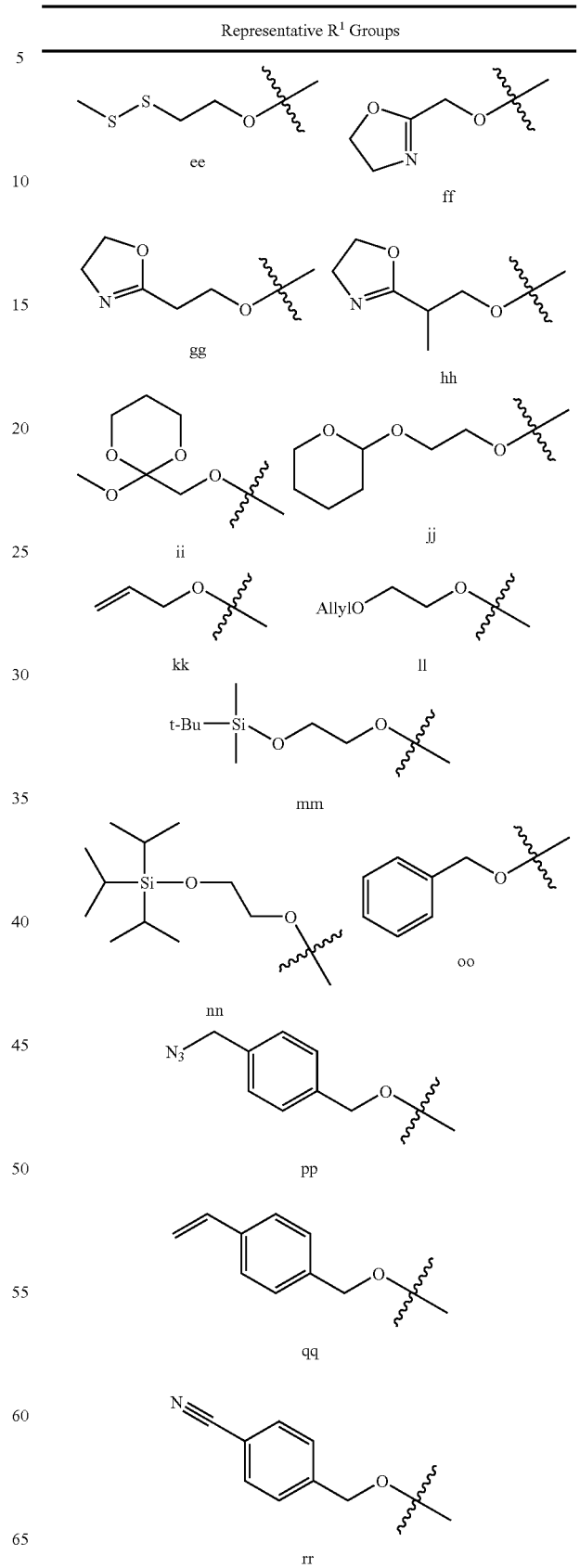

TABLE 8-continued
Representative R¹ Groups
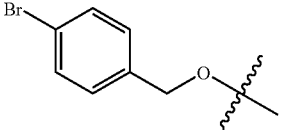
ss
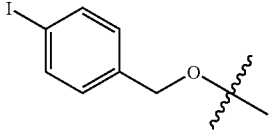
tt
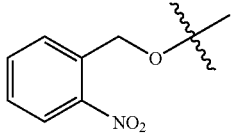
uu
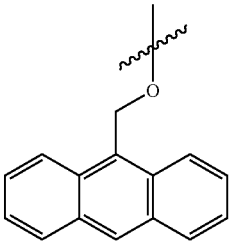
vv
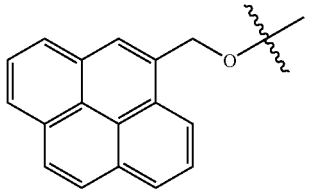
ww
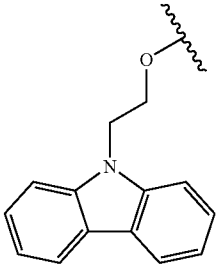
xx
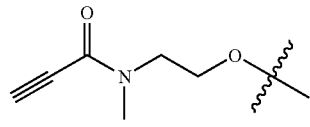
yy
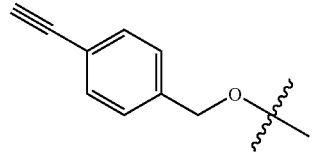
zz
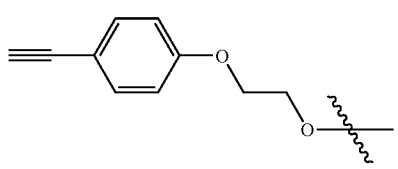
aaa
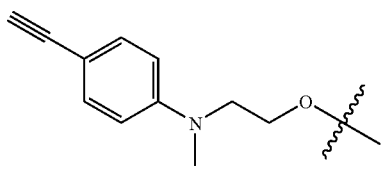
bbb
TABLE 8-continued
Representative R¹ Groups
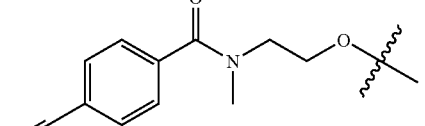
ccc
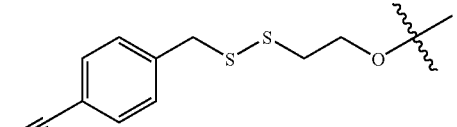
ddd
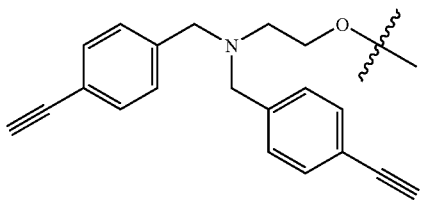
eee
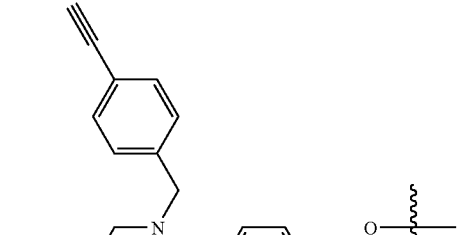
fff
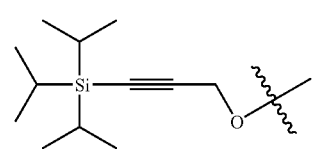
ggg
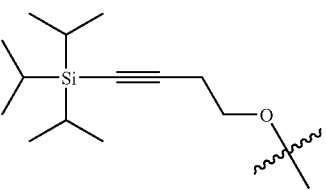
hhh TABLE 8-continued Representative R¹ Groups iii jjj kkk lll mmm nnn ooo ppp qqq rrr TABLE 8-continued Representative R¹ Groups sss ttt uuu vvv www xxx yyy zzz One of ordinary skill in the art would recognize that certain R¹ groups depicted in Tables 1-8 are protected groups, e.g. protected amine, protected hydroxyl, protected thiol, protected carboxylic acid, or protected alkyne groups. Each of these protected groups is readily deprotected (see, for example, Green). Accordingly, the deprotected groups corresponding to the protected groups set forth in Table 8 are also contemplated. According to another embodiment, the R¹ group of any of formulae I, I-a, II, and III is selected from a deprotected group of Table 8.

Additional exemplary R¹ groups of any of formulae I, I-a, II, and III are set forth in Table 8a, below.

TABLE 8a
Representative R¹ Groups
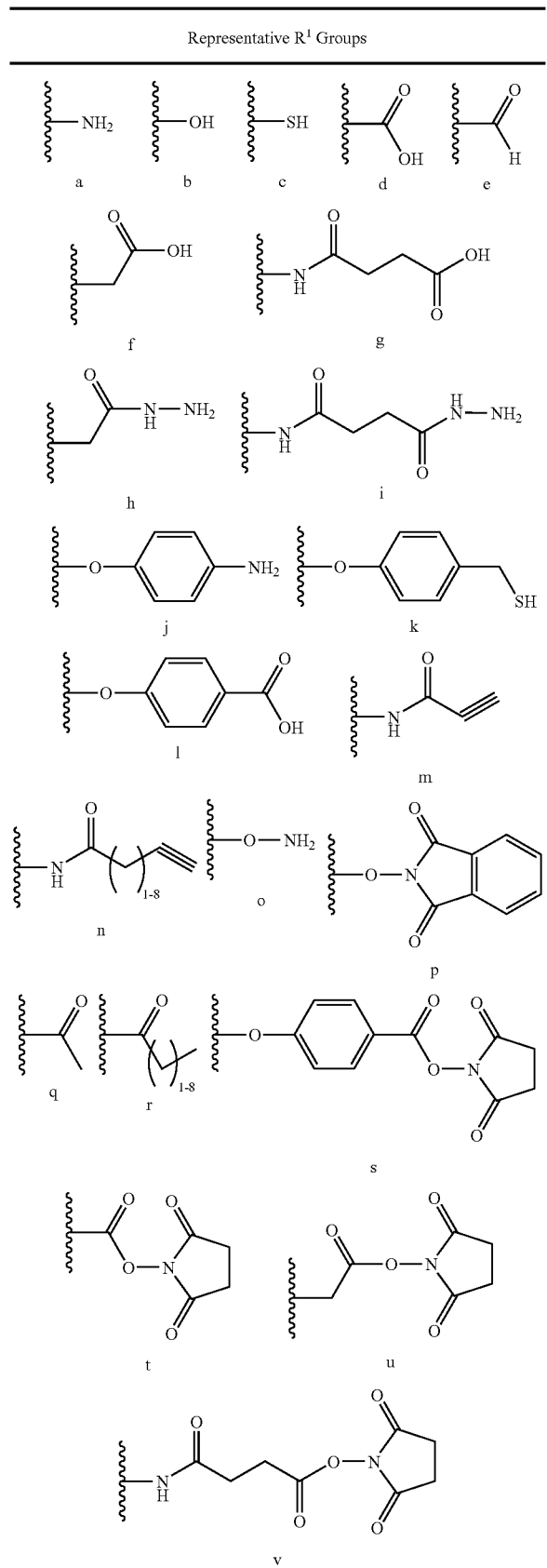
TABLE 8a-continued
Representative R¹ Groups
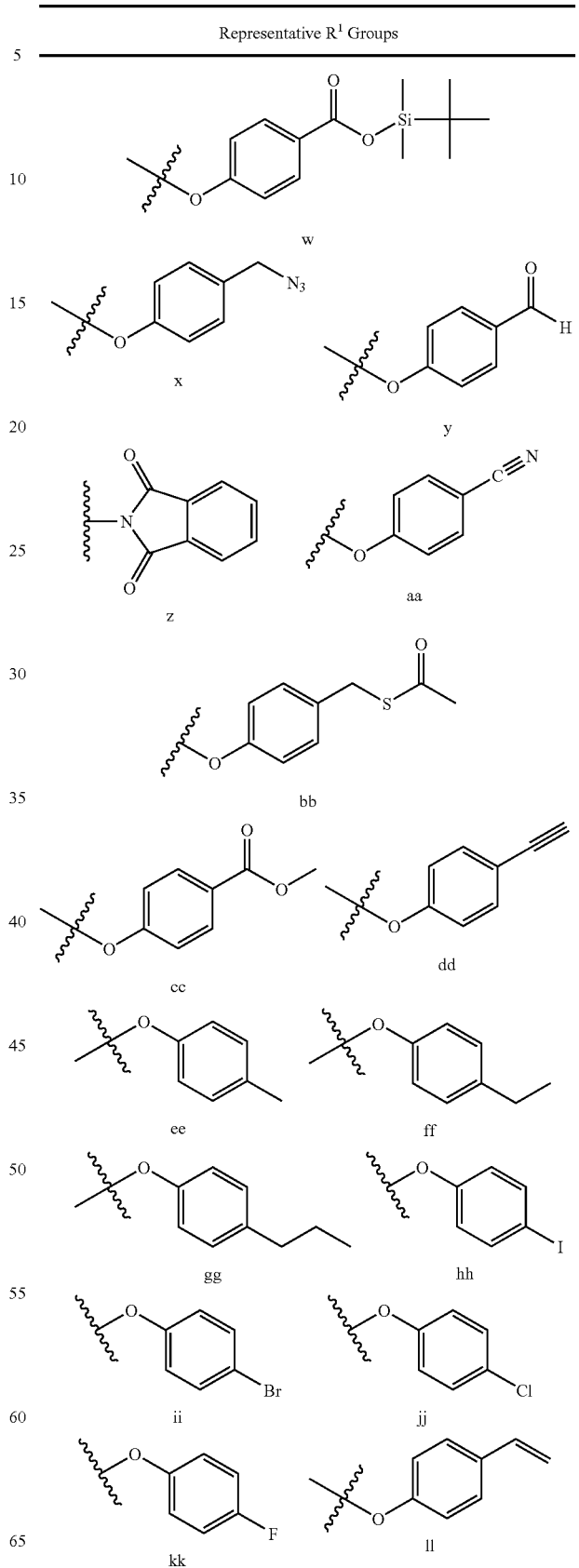

TABLE 8a-continued
Representative R¹ Groups
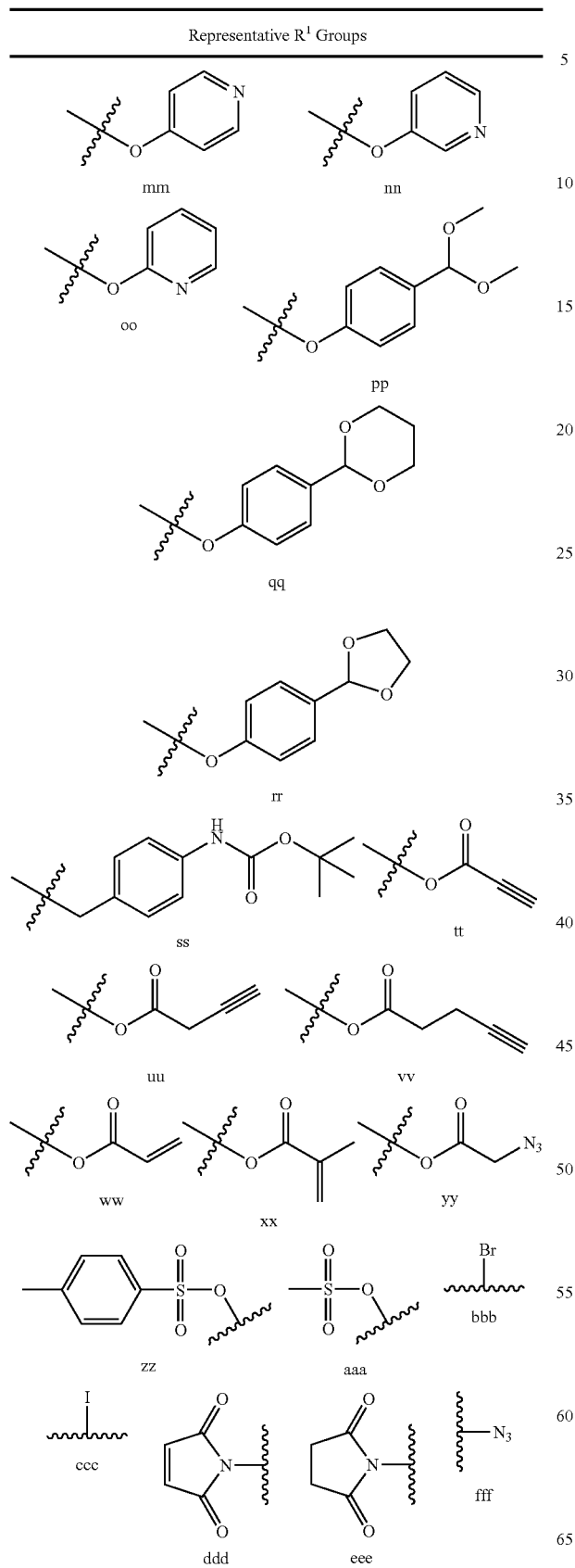
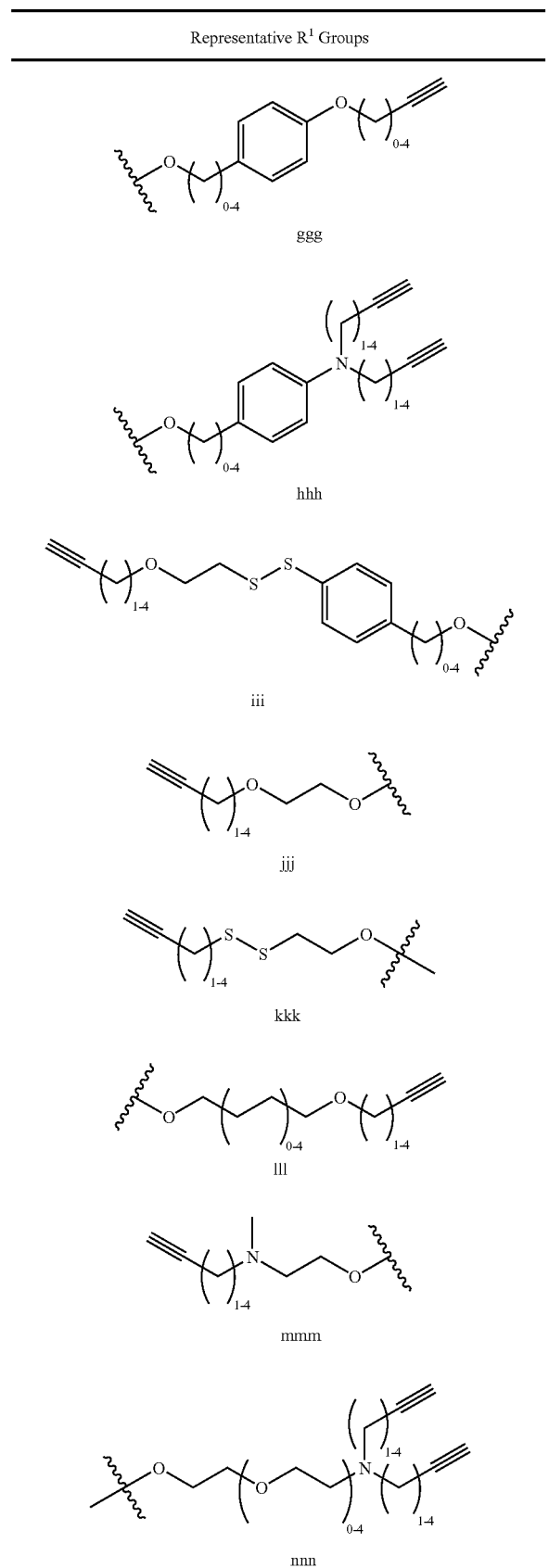

TABLE 8a-continued

Representative R¹ Groups ooo ppp qqq rrr sss ttt

In certain embodiments, the R¹ group of any of formulae I, I-a, II, and III is selected from any of those R¹ groups depicted in Table 8, supra. In other embodiments, the R¹ group of any of formulae I, I-a, II, and III is group k or l. In yet other embodiments, the R¹ group of any of formulae I, I-a, II, and III is n, o, cc, dd, ee, ff, hh, h, ii, jj, ll, or uu. In still other embodiments, the R¹ group of any of formulae I, I-a, II, and III is h, aa, yy, zz, or aaa.

According to another aspect of the present invention, the R¹ group of any of formulae I, I-a, II, and III is q, r, s, t, www, xxx, or yyy.

Exemplary $R^{2a}$ groups of any of formulae I, I-a, II, and III are set forth in Table 9, below.

TABLE 9

Representative $R^{2a}$ Groups i, ii, iii, iv, v, vi, vii, viii, ix, x, x, xi, xii, xiii, xiv TABLE 9-continued
Representative R$^{2a}$ Groups
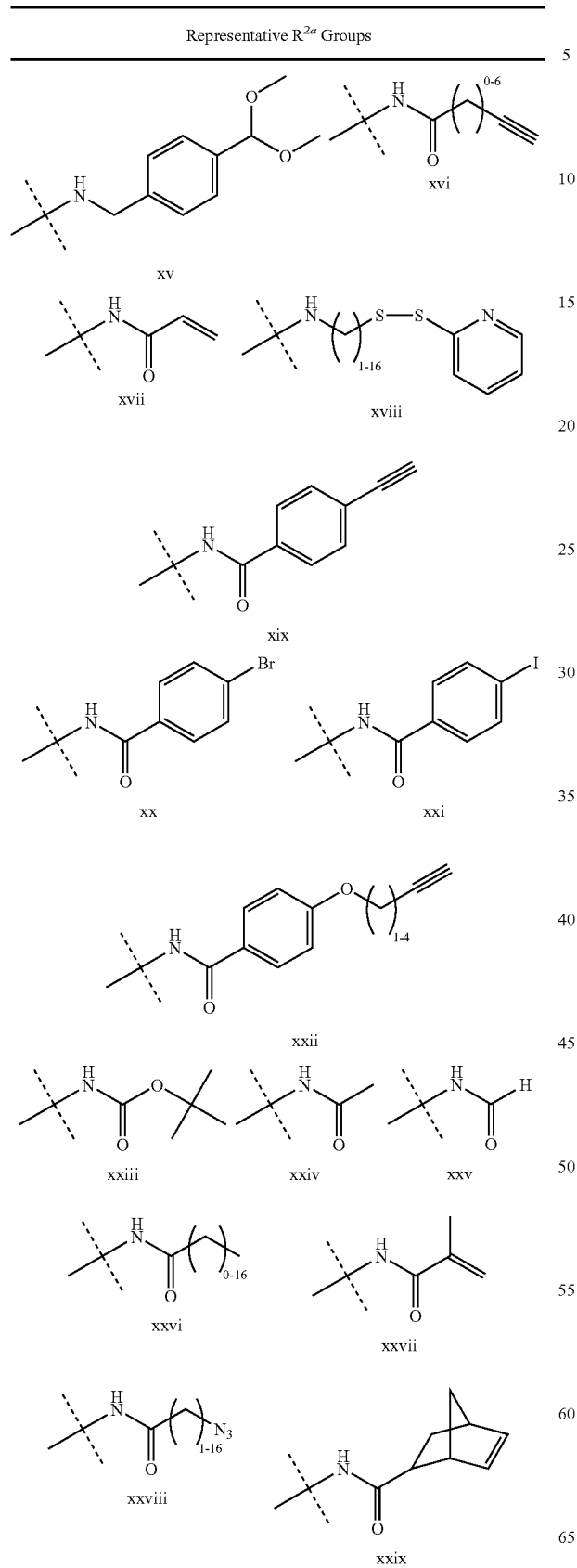
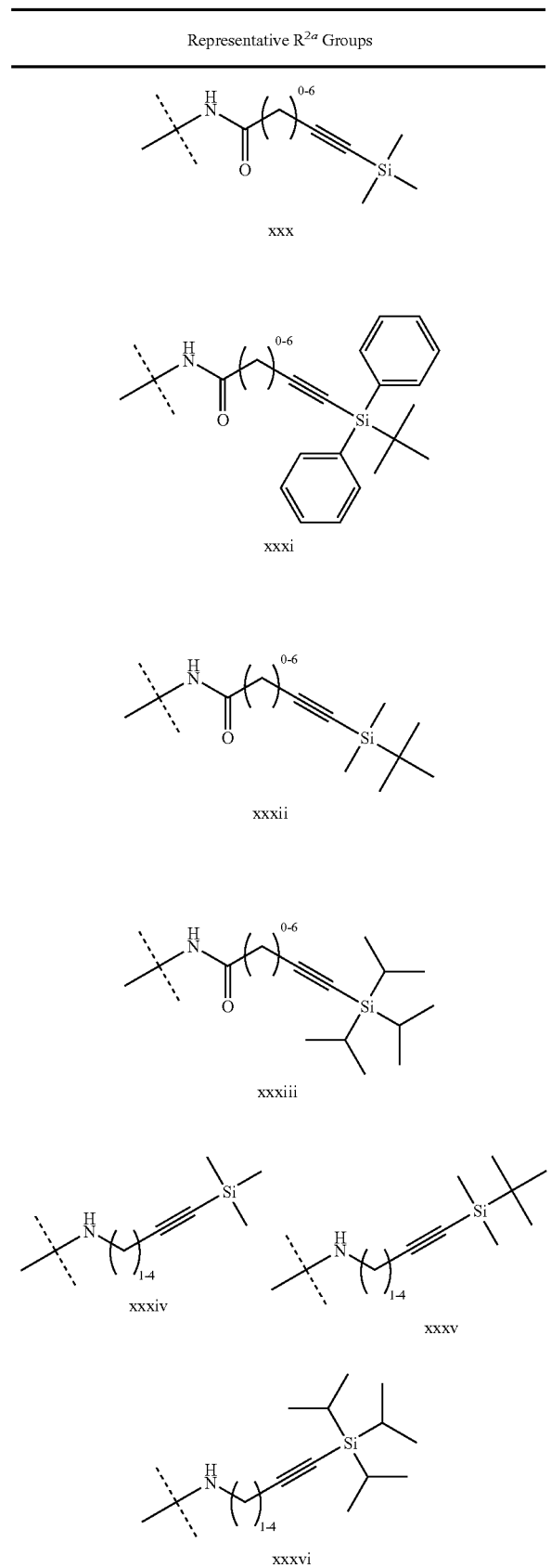

TABLE 9-continued

Representative R²ᵃ Groups

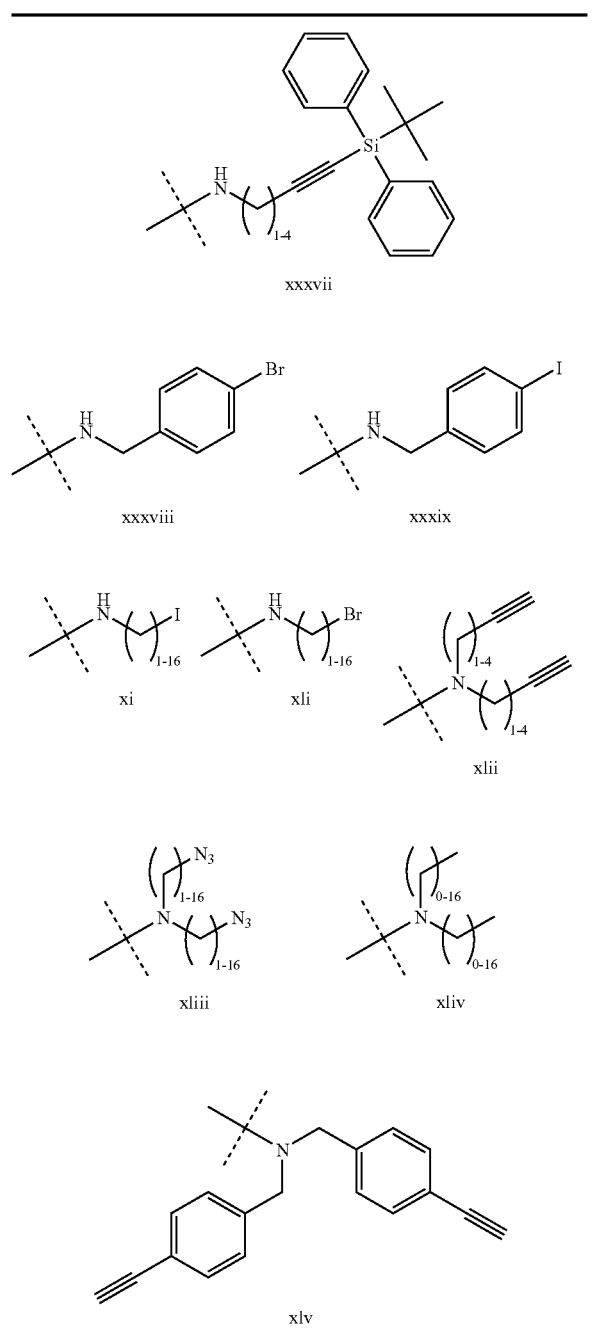

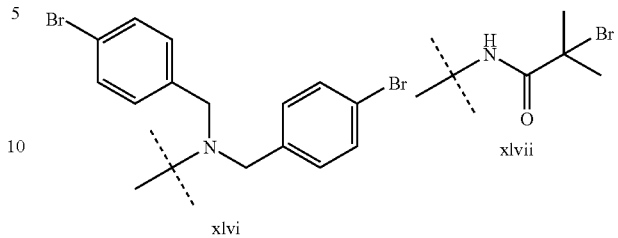

In certain embodiments, the R²ᵃ group of any of formulae I, I-a, II, and III is selected from any of those R²ᵃ groups depicted in Table 9, supra. In other embodiments, the R²ᵃ group of any of formulae I, I-a, II, and III is group v, viii, xvi, xix, xxii, xxx, xxxi, xxxii, xxxiii, xxxiv, xxxv, xxxvi, xxxvii, or xlii. In yet other embodiments, the R²ᵃ group of any of formulae I, I-a, II, and III is xv, xviii, xx, xxi, xxxviii, or xxxix. In certain embodiments, the R²ᵃ group of any of formulae I, I-a, II, and III is xxxiv.

One of ordinary skill in the art would recognize that certain R²ᵃ groups depicted in Table 9 are protected groups, e.g. protected amine, protected hydroxyl, protected thiol, protected carboxylic acid, or protected alkyne groups. Each of these protected groups is readily deprotected (see, for example, Green). Accordingly, the deprotected groups corresponding to the protected groups set forth in Table 9 are also contemplated. According to another embodiment, the R²ᵃ group of any of formulae I, I-a, II, and III is selected from a deprotected group of Table 9.

In certain embodiments, the present invention provides a compound of any of formulae I, I-a, II, and III wherein each variable is as defined herein or described in classes and subclasses both singly and in combination.

C. Drug Loading

According to another aspect, the present invention provides a drug-loaded micelle comprising a multiblock copolymer which comprises a polymeric hydrophilic block, optionally a crosslinkable or crosslinked poly(amino acid) block, and a hydrophobic D,L-mixed poly(amino acid) block, characterized in that said micelle has a drug-loaded inner core, optionally a crosslinked outer core, and a hydrophilic shell. As described herein, micelles of the present invention are especially useful for encapsulating hydrophobic therapeutic agents.

According to another embodiment, the present invention provides a drug-loaded micelle comprising a multiblock copolymer of formula I:

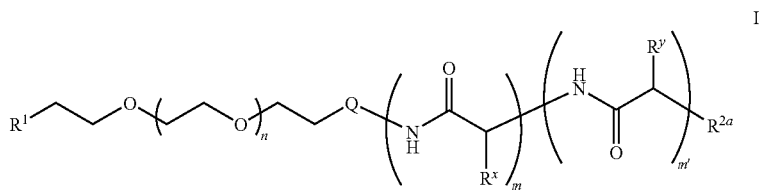

wherein:

n is 10-2500;

m is 0 to 1000;

m' is 2 to 1000;

$R^x$ is a natural or unnatural amino acid side-chain group that is capable of crosslinking;

$R^y$ forms a hydrophobic D,L-mixed poly(amino acid) block;

$R^1$ is —Z(CH$_2$CH$_2$Y)$_p$(CH$_2$)$_t$R$^3$, wherein:

Z is —O—, —S—, —C≡C—, or —CH$_2$—;

each Y is independently —O— or —S—;

p is 0-10;

t is 0-10; and $R^3$ is hydrogen, —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched C$_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:

two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

Embodiments with respect to each of the $R^1$, $R^{2a}$, Q, $R^x$, $R^y$, n, m, and m' groups of formula I, are as described in various classes and subclasses, both singly and in combination, herein.

In certain embodiments, the present invention provides a drug-loaded micelle, as described herein, wherein the drug is docetaxel or taxol.

In certain embodiments, the present invention provides a drug-loaded micelle, as described herein, wherein the drug is SN-38.

In certain embodiments, the present invention provides a drug-loaded micelle, as described herein, wherein the drug is irinotecan.

In certain embodiments, the present invention provides a drug-loaded micelle, as described herein, wherein the drug is letrozole.

In certain embodiments, the present invention provides a drug-loaded micelle, as described herein, wherein the drug is doxorubicin.

One of ordinary skill in the art will recognize that the $R^{2a}$ moiety can interact with the encapsulated drug. In certain embodiments, the $R^{2a}$ moiety is hydrophobic when the encapsulated drug is hydrophobic. Such hydrophobic $R^{2a}$ groups include linear and branched alkanes.

Without wishing to be bound by any particular theory, it is believed that the accomodation of structurally diverse therapeutic agents within a micelle of the present invention is effected by adjusting the hydrophobic D,L-mixed poly(amino acid) block, i.e., the block comprising $R^y$. As discussed above, the hydrophobic mixture of D and L stereoisomers affords a poly(amino acid) block with a random coil conformation thereby enhancing the encapsulation of hydrophobic drugs.

In certain embodiments, micelles of the present invention are loaded with a hydrophobic drug. In accordance with such embodiments, $R^y$ forms a hydrophobic D,L-mixed amino acid block. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates, or mixtures thereof. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboxylate functional groups of $R^y$ are as described herein.

In other embodiments, the $R^y$ group of formula I comprises a mixture of D-hydrophobic and L-hydrophilic amino acid side-chain groups such that the overall poly(amino acid) block comprising $R^y$ is hydrophobic. Such mixtures of amino acid side-chain groups include D-phenylalanine/L-tyrosine, D-phenalanine/L-serine, D-benzyl glutamate/L-tyrosine, D-benzyl glutamate/L-aspartic acid and the like. According to another embodiment, $R^y$ is a hydrophobic amino acid side-chain group selected from D-leucine, D-phenylalanine, D-alanine, D-benzyl aspartate, or D-benzyl glutamate, and one or more of L-tyrosine, L-cysteine, L-aspartic acid, L-glutamic acid, L-DOPA, L-histidine, L-lysine, or L-ornithine.

Hydrophobic small molecule drugs suitable for loading into micelles of the present invention are well known in the art. In certain embodiments, the present invention provides a drug-loaded micelle as described herein, wherein the drug is a hydrophobic drug selected from those described herein, infra.

In certain embodiments, the present invention provides a drug-loaded micelle comprising a diblock copolymer of formula I-a:

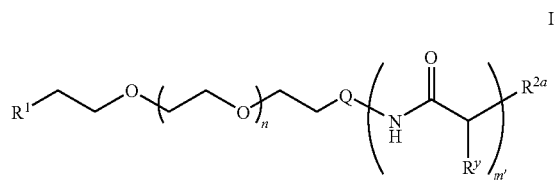

I-a wherein each of the $R^1$, $R^{2a}$, Q, $R^y$, n, and m' groups of formula I-a, are as described in various classes and subclasses, both singly and in combination, herein.

In certain embodiments, the $R^y$ group of formula I-a comprises a mixture of hydrophobic and hydrophilic amino acid side-chain groups such that the overall poly(amino acid) block comprising $R^y$ is hydrophobic. In other embodiments, $R^y$ comprises a mixture of phenylalanine and tyrosine. In other embodiments, $R^y$ comprises a mixture of benzyl glutamate and aspartic acid. In yet other embodiments, $R^y$ comprises a mixture of benzyl glutamate and glutamic acid. By way of example, this particular copolymer is used to encapsulate one or more of docetaxel, CPT, and paclitaxel in the hydrophobic of benzyl glutamate/aspartic acid inner core. Although only sparingly soluble in water, these drugs possess polar functionalities (e.g. amine, alcohol, and phenols), which makes the incorporation of aspartic acid, a polar amino acid, advantageous for effective encapsulation. By utilizing this particular core composition, relatively high docetaxel, CPT, and paclitaxel loadings are achieved.

In certain embodiments, the present invention provides a micelle comprising a compound of formula I-a characterized in that docetaxel, CPT, and paclitaxel are encapsulated in the hydrophobic benzyl glutamate/aspartic acid inner core. In still other embodiments, m' is 10-50 repeat units. In certain embodiments, the phenylalanine/tyrosine ratio of m' is 4:1. In other embodiments the phenylalanine/tyrosine ratio of m' is 9:1. In still other embodiments, the benzyl glutamate/aspartic acid ratio of m' is 3:1. In other embodiments, $R^y$ comprises 4-8 aspartic acid repeat units and 20-32 benzyl glutamate. In still other embodiments, $R^y$ comprises 2-40 tyrosine and 10-100 benzyl glutamate repeat units.

In other embodiments, the present invention provides a drug-loaded micelle comprising a multiblock copolymer of formula II:

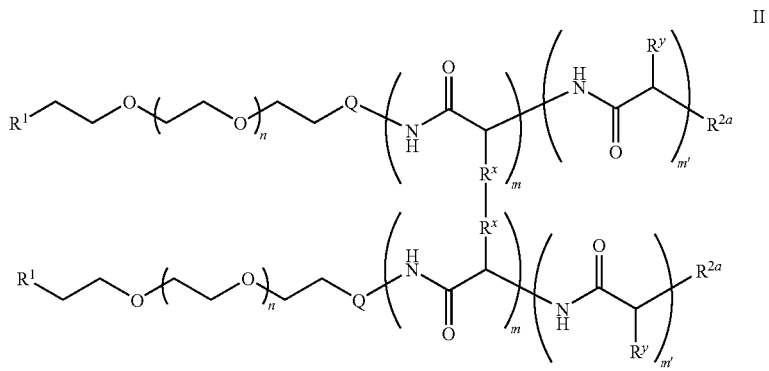

II wherein each of the $R^1$, $R^{2a}$, Q, $R^x$, $R^y$, n, m, and m' groups of formula II, are as described in various classes and subclasses, both singly and in combination, herein.

In still other embodiments, the present invention provides a drug-loaded micelle comprising a multiblock copolymer of formula III:

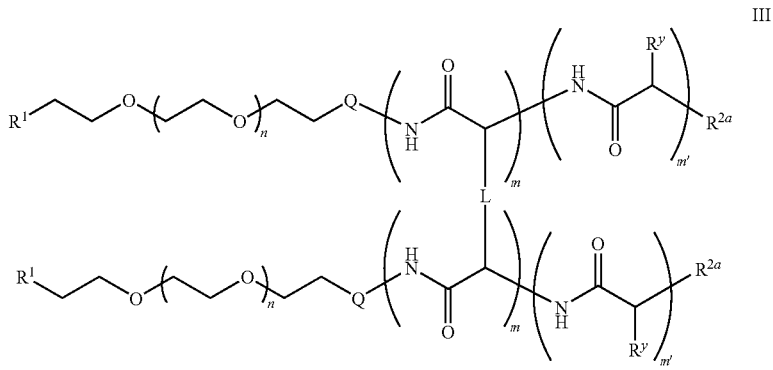

III wherein each of the $R^1$, $R^{2a}$, Q, $R^x$, $R^y$, n, m, L, and m' groups of formula III, are as described in various classes and subclasses, both singly and in combination, herein.

In other embodiments, the $R^y$ group of formula III comprises a mixture of D-hydrophobic and L-hydrophilic amino acid side-chain groups such that the overall poly(amino acid) block comprising $R^y$ is hydrophobic. Such mixtures of amino acid side-chain groups include D-phenylalanine/L-tyrosine, D-phenalanine/L-serine, D-benzyl glutamate/L-tyrosine, D-benzyl glutamate/L-aspartic acid and the like. According to another embodiment, $R^y$ is a hydrophobic amino acid side-chain group selected from D-leucine, D-phenylalanine, D-alanine, D-benzyl aspartate, or D-benzyl glutamate, and one or more of L-tyrosine, L-cysteine, L-aspartic acid, L-glutamic acid, L-DOPA, L-histidine, L-lysine, or L-ornithine.

In certain embodiments, the present invention provides a micelle comprising a compound of formula III characterized in that docetaxel, doxorubicin, CPT, and paclitaxel are encapsulated in the hydrophobic phenylalanine/tyrosine inner core and the poly(aspartic acid) outer core is crosslinked with zinc. In certain embodiments, m and m' add up to about 30 to about 60. In still other embodiments, m is 1-20 repeat units and m' is 10-50 repeat units. In certain embodiments, the phenylalanine/tyrosine ratio of m' is 4:1. In other embodiments the phenylalanine/tyrosine ratio of m' is 9:1. In still other embodiments, the phenylalanine/tyrosine ratio of m' is 3:1. In other embodiments, $R^y$ comprises 4-8 tyrosine repeat units and 20-32 phenylalanine. In still other embodiments, $R^y$ comprises 2-40 tyrosine and 10-100 phenylalanine repeat units.

Hydrophobic small molecule drugs suitable for loading into micelles of the present invention are well known in the art. In certain embodiments, the present invention provides a drug-loaded micelle as described herein, wherein the drug is a hydrophobic drug selected from analgesics, anti-inflammatory agents, antihelminthics, anti-arrhythmic agents, antibacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opiod analgesics, protease inhibitors, sex hormones, stimulants, muscle relaxants, anti-osteoporosis agents, anti-obesity agents, cognition enhancers, anti-urinary incontinence agents, anti-benign prostate hypertrophy agents, essential fatty acids, non-essential fatty acids, and mixtures thereof.

In other embodiments, the hydrophobic drug is selected from one or more analgesics, anti-bacterial agents, anti-viral agents, anti-inflammatory agents, anti-depressants, anti-diabetics, anti-epileptics, anti-hypertensive agents, anti-migraine agents, immunosuppressants, anxiolytic agents, sedatives, hypnotics, neuroleptics, β-blockers, gastro-intestinal agents, lipid regulating agents, anti-anginal agents, Cox-2 inhibitors, leukotriene inhibitors, macrolides, muscle relaxants, opioid analgesics, protease inhibitors, sex hormones, cognition enhancers, anti-urinary incontinence agents, and mixtures thereof.

According to one aspect, the present invention provides a micelle, as described herein, loaded with a hydrophobic drug selected from any one or more of a Exemestane (aromasin), Camptosar (irinotecan), Ellence (epirubicin), Femara (Letrozole), Gleevac (imatinib mesylate), Lentaron (formestane), Cytadren/Orimeten (aminoglutethimide), Temodar, Proscar (finasteride), Viadur (leuprolide), Nexavar (Sorafenib), Kytril (Granisetron), Taxotere (Docetaxel), Taxol (paclitaxel), Kytril (Granisetron), Vesanoid (tretinoin) (retin A), XELODA (Capecitabine), Arimidex (Anastrozole), Casodex/Cosudex (Bicalutamide), Faslodex (Fulvestrant), Iressa (Gefitinib), Nolvadex, Istubal, Valodex (tamoxifen citrate), Tomudex (Raltitrexed), Zoladex (goserelin acetate), Leustatin (Cladribine), Velcade (bortezomib), Mylotarg (gemtuzumab ozogamicin), Alimta (pemetrexed), Gemzar (gemcitabine hydrochloride), Rituxan (rituximab), Revlimid (lenalidomide), Thalomid (thalidomide), Alkeran (melphalan), and derivatives thereof.

D. Polymer Conjugation

In addition to their core-shell morphology, polymer micelles can be modified to enable passive and active cell-targeting to maximize the benefits of current and future therapeutic agents. Because drug-loaded micelles typically possess diameters greater than 20 nm, they exhibit dramatically increased circulation time when compared to stand-alone drugs due to minimized renal clearance. This unique feature of nanovectors and polymeric drugs leads to selective accumulation in diseased tissue, especially cancerous tissue due to the enhanced permeation and retention effect ("EPR"). The EPR effect is a consequence of the disorganized nature of the tumor vasculature, which results in increased permeability of polymer therapeutics and drug retention at the tumor site. In addition to passive cell targeting by the EPR effect, micelles are designed to actively target tumor cells through the chemical attachment of targeting groups to the micelle periphery. The incorporation of such groups is most often accomplished through end-group functionalization of the hydrophilic block using chemical conjugation techniques. Like viral particles, micelles functionalized with targeting groups utilize receptor-ligand interactions to control the spatial distribution of the micelles after administration, further enhancing cell-specific delivery of therapeutics. In cancer therapy, targeting groups are designed to interact with receptors that are over-expressed in cancerous tissue relative to normal tissue such as folic acid, oligopeptides, sugars, and monoclonal antibodies. See Pan, D.; Turner, J. L.; Wooley, K. L. *Chem. Commun.* 2003, 2400-2401; Gabizon, A.; Shmeeda, H.; Horowitz, A. T.; Zalipsky, S. *Adv. Drug Deliv. Rev.* 2004, 56, 1177-1202; Reynolds, P. N.; Dmitriev, I.; Curiel, D. T. Vector. Gene Ther. 1999, 6, 1336-1339; Derycke, A. S. L.; Kamuhabwa, A.; Gijsens, A.; Roskams, T.; De Vos, D.; Kasran, A.; Huwyler, J.; Missiaen, L.; de Witte, P. A. M. T *J. Nat. Cancer Inst.* 2004, 96, 1620-30; Nasongkla, N., Shuai, X., Ai, H.,; Weinberg, B. D. P., J.; Boothman, D. A.; Gao, J. *Angew. Chem. Int. Ed.* 2004, 43, 6323-6327; Jule, E.; Nagasaki, Y.; Kataoka, K. *Bioconj. Chem.* 2003, 14, 177-186; Stubenrauch, K.; Gleiter, S.; Brinkmann, U.; Rudolph, R.; Lilie, H. *Biochem. J.* 2001, 356, 867-873; Kurschus, F. C.; Kleinschmidt, M.; Fellows, E.; Dornmair, K.; Rudolph, R.; Lilie, H.; Jenne, D. E. *FEBS Lett.* 2004, 562, 87-92; and Jones, S. D.; Marasco, W. A. *Adv. Drug Del. Rev.* 1998, 31, 153-170.

Compounds of any of formulae I, I-a, II, and III having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of any of formulae I, I-a, II, and III to a macromolecule via Click chemistry. Yet another embodiment of the present invention provides a macromolecule conjugated to a compound of any of formulae I, I-a, II, and III via the $R^1$ group.

After incorporating the poly (amino acid) block portions into the multi-block copolymer of the present invention resulting in a multi-block copolymer of the form W—X—X', the other end-group functionality, corresponding to the $R^1$ moiety of any of formulae I, I-a, II, and III, can be used to attach targeting groups for cell specific delivery including, but not limited to, attach targeting groups for cell specific delivery including, but not limited to, proteins, oliogopeptides, antibodies, monosaccarides, oligosaccharides, vitamins, or other small biomolecules. Such targeting groups include, but or not limited to monoclonal and polyclonal antibodies (e.g. IgG, IgA, IgM, IgD, IgE antibodies), sugars (e.g. mannose, mannose-6-phosphate, galactose), proteins (e.g. Transferrin), oligopeptides (e.g. cyclic and acylic RGD-containing oligopedptides), and vitamins (e.g. folate). Alternatively, the $R^1$ moiety of any of formulae I, I-a, II, and III is bonded to a biomolecule, drug, cell, or other suitable substrate.

In other embodiments, the $R^1$ moiety of any of formulae I, I-a, II, and III is bonded to biomolecules which promote cell entry and/or endosomal escape. Such biomolecules include, but are not limited to, oligopeptides containing protein transduction domains such as the HIV Tat peptide sequence (GRKKRRQRRR) or oligoarginine (RRRRRRRRR). Oligopeptides which undergo conformational changes in varying pH environments such oligohistidine (HHHHH) also promote cell entry and endosomal escape.

In other embodiments, the $R^1$ moiety of any of formulae I, I-a, II, and III is bonded to detectable moieties, such as fluorescent dyes or labels for positron emission tomography including molecules containing radioisotopes (e.g. $^{18}F$) or ligands with bound radioactive metals (e.g. $^{62}Cu$). In other embodiments, the $R^1$ moiety of any of formulae I, I-a, II, and III is bonded to a contrast agents for magnetic resonance imaging such as gadolinium, gadolinium chelates, or iron oxide (e.g $Fe_3O_4$ and $Fe_2O_3$) particles. In other embodiments, the $R^1$ moiety of any of formulae I, I-a, II, and III is bonded to a semiconducting nanoparticle such as cadmium selenide, cadmium sulfide, or cadmium telluride or bonded to other metal nanoparticles such as colloidal gold. In other embodiments, the $R^1$ moiety of any of formulae I, I-a, II, and III is bonded to natural or synthetic surfaces, cells, viruses, dyes, drugs, chelating agents, or used for incorporation into hydrogels or other tissue scaffolds.

In one embodiment, the $R^1$ moiety of any of formulae I, I-a, II, and III is an alkyne or a terminal alkyne derivative which is capable of undergoing [3+2] cycloaddition reactions with complementary azide-bearing molecules and biomolecules. In another embodiment, the $R^1$ moiety of any of formulae I, I-a, II, and III is an azide or an azide derivative which is capable of undergoing [3+2] cycloaddition reactions with complementary alkyne-bearing molecules and biomolecules (i.e. click chemistry).

Click chemistry has become a popular method of bioconjugation due to its high reactivity and selectivity, even in biological media. See Kolb, H. C.; Finn, M. G.; Sharpless, K. B. *Angew. Chem. Int. Ed.* 2001, 40, 2004-2021; and Wang, Q.; Chan, T. R.; Hilgraf, R.; Fokin, V. V.; Sharpless, K. B.; Finn, M. G. *J. Am. Chem. Soc.* 2003, 125, 3192-3193. In addition, currently available recombinant techniques permit the introduction of azides and alkyne-bearing non-canonical amino acids into proteins, cells, viruses, bacteria, and other biological entities that consist of or display proteins. See Link, A. J.; Vink, M. K. S.; Tirrell, D. A. *J. Am. Chem. Soc.* 2004, 126, 10598-10602; Deiters, A.; Cropp, T. A.; Mukherji, M.; Chin, J. W.; Anderson, C.; Schultz, P. G. *J. Am. Chem. Soc.* 2003, 125, 11782-11783.

In another embodiment, the [3+2] cycloaddition reaction of azide or acetylene-bearing nanovectors and complimentary azide or acetylene-bearing biomolecules are transition metal catalyzed. Copper-containing molecules which catalyze the "click" reaction include, but are not limited to, copper bromide (CuBr), copper chloride (CuCl), copper sulfate ($CuSO_4$), copper iodide (CuI), $[Cu(MeCN)_4](OTf)$, and $[Cu(MeCN)_4](PF_6)$. Organic and inorganic metal-binding ligands can be used in conjunction with metal catalysts and include, but are not limited to, sodium ascorbate, tris(triazolyl)amine ligands, tris(carboxyethyl)phosphine (TCEP), and sulfonated bathophenanthroline ligands.

In another embodiment, the $R^1$ moiety of any of formulae I, I-a, II, and III is an hydrazine or hydrazide derivative which is capable of undergoing reaction with biomolecules containing aldehydes or ketones to form hydrazone linkages. In another embodiment, the $R^1$ moiety of any of formulae I, I-a, II, and III is an aldehyde or ketone derivative which is capable of undergoing reaction with biomolecules containing a hydrazine or hydrazide derivative to form hydrazone linkages.

In another embodiment, the $R^1$ moiety of any of formulae I, I-a, II, and III is a hydroxylamine derivative which is capable of undergoing reaction with biomolecules containing aldehydes or ketones. In another embodiment, the $R^1$ moiety of any of formulae I, I-a, II, and III is an aldehyde or ketone which is capable of undergoing reaction with biomolecules containing a hydroxylamine, or a hydroxylamine derivative.

In yet another embodiment, the $R^1$ moiety of any of formulae I, I-a, II, and III is an aldehyde or ketone derivative which is capable of undergoing reaction with biomolecules containing primary or secondary amines to form imine linkages. In another embodiment, the $R^1$ moiety of any of formulae I, I-a, II, and III is a primary or secondary amine which is capable of undergoing reaction with biomolecules containing an aldehyde or ketone functionality to form imine linkages. It will be appreciated that imine linkages can be further converted to stable amine linkages by treatment with a suitable reducing agent (e.g. lithium aluminum hydride, sodium borohydride, sodium cyanoborohydride, etc.)

In yet another embodiment, the $R^1$ moiety of any of formulae I, I-a, II, and III is an amine (primary or secondary) or alcohol which is capable of undergoing reaction with biomolecules containing activated esters (e.g. 4-nitrophenol ester, N-hydroxysuccinimide, pentafluorophenyl ester, ortho-pyridylthioester), to form amide or ester linkages. In still other embodiments, the $R^1$ moiety of any of formulae I, I-a, II, and III is an activated ester which is capable of undergoing reaction with biomolecules possessing amine (primary or secondary) or alcohols to form amide or ester linkages.

In still other embodiments, the $R^1$ moiety of any of formulae I, I-a, II, and III is an amine or alcohol which is bound to biomolecules with carboxylic acid functionality using a suitable coupling agent. In still other embodiments, the $R^1$ moiety of any of formulae I, I-a, II, and III is a carboxylic acid functionality which is bound to biomolecules containing amine or alcohol functionality using a suitable coupling agent. Such coupling agents include, but are not limited to, carbodiimides (e.g. 1-ethyl-3-(3-dimethylaminopropyl)-carbodiimide (EDC), diisopropyl carbodiimide (DIC), dicyclohexyl carbodiimide (DCC)), aminium or phosphonium derivatives (e.g. PyBOP, PyAOP, TBTU, HATU, HBTU), or a combination of 1-hydroxybenzotriazole (HOBt) and a aminium or phosphonium derivative.

In another embodiment, the $R^1$ moiety of any of formulae I, I-a, II, and III is an electrophile such as maleimide, a maleimide derivative, or a bromoacetamide derivative, which is capable of reaction with biomolecules containing thiols or amines. In another embodiment, the $R^1$ moiety of any of formulae I, I-a, II, and III is a nucleophile such as an amine or thiol which is capable or reaction with biomolecules containing electrophilic functionality such as maleimide, a maleimide derivative, or a bromoacetamide derivative.

In still other embodiments, the $R^1$ moiety of any of formulae I, I-a, II, and III is a ortho-pyridyl disulfide moiety which undergoes disulfide exchange with biomolecules containing thiol functionality. In still other embodiments, the $R^1$ moiety of any of formulae I, I-a, II, and III is a thiol or thiol derivative these different $R^1$ groups. Such conjugation reactions are well known to one of ordinary skill in the art and include those described herein.

4. General Methods for Providing Compounds of the Present Invention

Multiblock copolymers of the present invention are prepared by methods known to one of ordinary skill in the art and those described in detail in U.S. patent application Ser. No. 11/325,020 filed Jan. 4, 2006 and published as US 20060172914 on Aug. 3, 2006, the entirety of which is hereby incorporated herein by reference. Generally, such multiblock copolymers are prepared by sequentially polymerizing one or more cyclic amino acid monomers onto a hydrophilic polymer having a terminal amine salt wherein said polymerization is initiated by said amine salt. In certain embodiments, said polymerization occurs by ring-opening polymerization of the cyclic amino acid monomers. In other embodiments, the cyclic amino acid monomer is an amino acid NCA, lactam, or imide.

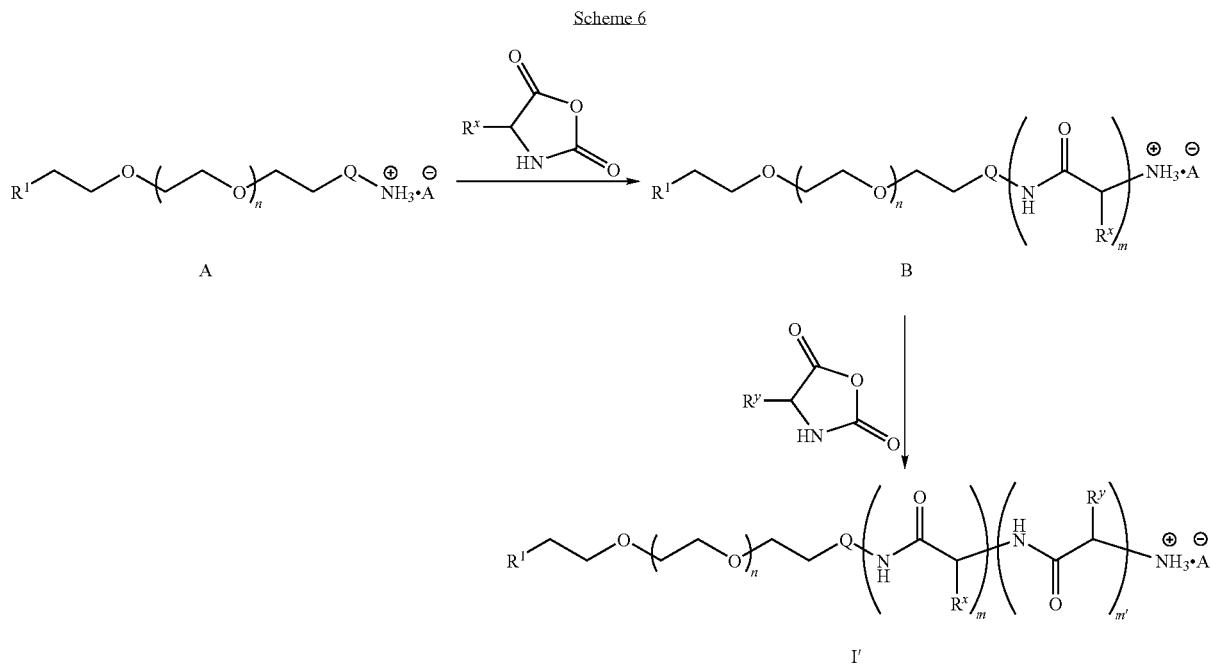

Scheme 6 which undergoes disulfide exchange with biomolecules containing ortho-pyridyl disulfide functionality. It will be appreciated that such exchange reactions result in a disulfide linkage which is reversible in the presence of a suitable reducing agent (e.g. glutathione, dithiothreitol (DTT), etc.).

In certain embodiments, micelles of the present invention are mixed micelles comprising one or more compounds of formula I, I-a, II, or III. It will be appreciated that mixed micelles having different $R^1$ groups, as described herein, can be conjugated to multiple other compounds and/or macromolecules. For example, a mixed micelle of the present invention can have one $R^1$ group suitable for Click chemistry and another $R^1$ group suitable for covalent attachment via a variety of coupling reactions. Such a mixed micelle can be conjugated to different compounds and/or macromolecules via Scheme 6 above depicts a general method for preparing multiblock polymers of the present invention. A macroinitiator of formula A is treated with a first amino acid NCA to form a compound of formula B having a first amino acid block. The second amino acid NCA is added to the living polymer of formula B to form a compound of formula I' having two differing amino acid blocks. Each of the $R^1$, A, n, Q, $R^x$, $R^y$, m, and m' groups depicted in Scheme 6 are as defined and described in classes and subclasses, singly and in combination, herein.

One step in the preparation of a compound of formula I comprises terminating the living polymer chain-end of the compound of formula I' with a suitable polymerization terminator to afford a compound of formula I. One of ordinary skill in the art would recognize that the polymerization terminator provides the $R^{2a}$ group of formula I. Accordingly, embodiments directed to the $R^{2a}$ group of formula I as set forth above and herein, are also directed to the suitable polymerization terminator itself, and similarly, embodiments directed to the suitable polymerization terminator, as set forth above and herein, are also directed to the $R^{2a}$ group of formula I.

As described above, compounds of formula I are prepared from compounds of formula I' by treatment with a suitable terminating agent. One of ordinary skill in the art would recognize that compounds of formula I are also readily prepared directly from compounds of formula I'. In such cases, and in certain embodiments, the compound of formula I' is treated with a base to form the freebase compound prior to, or concurrent with, treatment with the suitable terminating agent. For example, it is contemplated that a compound of formula I' is treated with a base and suitable terminating agent in the same reaction to form a freebase of that compound. In such cases, it is also contemplated that the base may also serve as the reaction medium.

One of ordinary skill in the art would also recognize that the above method for preparing a compound of formula I may be performed as a "one-pot" synthesis of compounds of formula I that utilizes the living polymer chain-end to incorporate the $R^2$ group of formula I. Alternatively, compounds of formula I may also be prepared in a multi-step fashion. For example, the living polymer chain-end of a compound of formula I' may be quenched to afford an amino group which may then be further derivatized, according to known methods, to afford a compound of formula I.

One of ordinary skill in the art will recognize that a variety of polymerization terminating agents are suitable for the present invention. Such polymerization terminating agents include any $R^{2a}$-containing group capable of reacting with the living polymer chain-end of a compound of formula I', or the free-based amino group of formula I', to afford a compound of formula I. Thus, polymerization terminating agents include anhydrides, and other acylating agents, and groups that contain a suitable leaving group LG that is subject to nucleophilic displacement.

Alternatively, compounds of formula I' may be coupled to carboxylic acid-containing groups to form an amide thereof. Thus, it is contemplated that the amine group of formula I' or freease thereof, may be coupled with a carboxylic acid moiety to afford compounds of formula I wherein $R^{2a}$ is —NHC(O)$R^4$. Such coupling reactions are well known in the art. In certain embodiments, the coupling is achieved with a suitable coupling reagent. Such reagents are well known in the art and include, for example, DCC and EDC, among others. In other embodiments, the carboxylic acid moiety is activated for use in the coupling reaction. Such activation includes formation of an acyl halide, use of a Mukaiyama reagent, and the like. These methods, and others, are known to one of ordinary skill in the art, e.g., see, "Advanced Organic Chemistry," Jerry March, 5$^{th}$ Ed., pp. 351-357, John Wiley and Sons, N.Y.

A "suitable leaving group that is subject to nucleophilic displacement" is a chemical group that is readily displaced by a desired incoming chemical moiety. Suitable leaving groups are well known in the art, e.g., see, March. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyloxy(mesyloxy), tosyloxy, triflyloxy, nitrophenylsulfonyloxy(nosyloxy), and bromo-phenylsulfonyloxy(brosyloxy).

According to an alternate embodiment, the suitable leaving group may be generated in situ within the reaction medium. For example, a leaving group may be generated in situ from a precursor of that compound wherein said precursor contains a group readily replaced by said leaving group in situ.

Alternatively, when the $R^{2a}$ group of formula I is a mono- or di-protected amine, the protecting group(s) is removed and that functional group may be derivatized or protected with a different protecting group. It will be appreciated that the removal of any protecting group of the $R^{2a}$ group of formula I is performed by methods suitable for that protecting group. Such methods are described in detail in Green.

In other embodiments, the $R^{2a}$ group of formula I is incorporated by derivatization of the amino group of formula I', or freebase thereof, via anhydride coupling, optionally in the presence of base as appropriate. One of ordinary skill in the art would recognize that anhydride polymerization terminating agents containing an azide, an aldehyde, a hydroxyl, an alkyne, and other groups, or protected forms thereof, may be used to incorporate said azide, said aldehyde, said protected hydroxyl, said alkyne, and other groups into the $R^{2a}$ group of compounds of formula I. It will also be appreciated that such anhydride polymerization terminating agents are also suitable for terminating the living polymer chain-end of a compound of formula I', or freebase thereof. Such anhydride polymerization terminating agents include, but are not limited to, those set forth in Table 10 below.

TABLE 10

Representative Anhydride Polymerization Terminating Agents

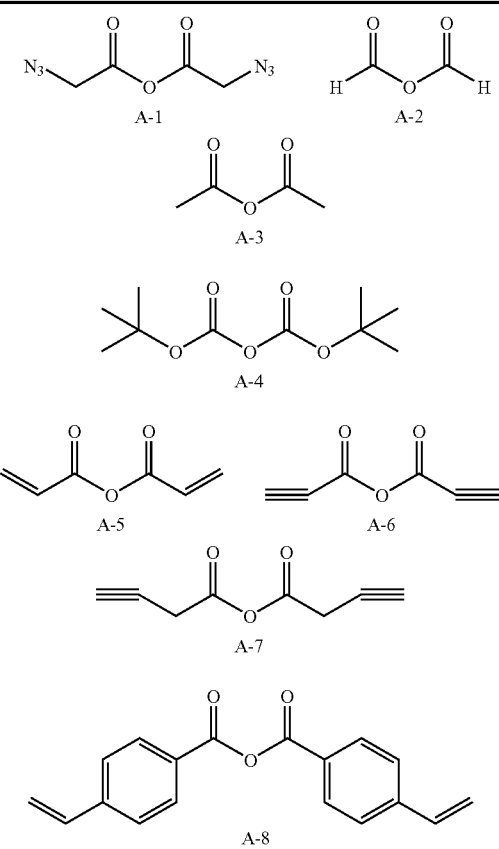

TABLE 10-continued

Representative Anhydride Polymerization Terminating Agents

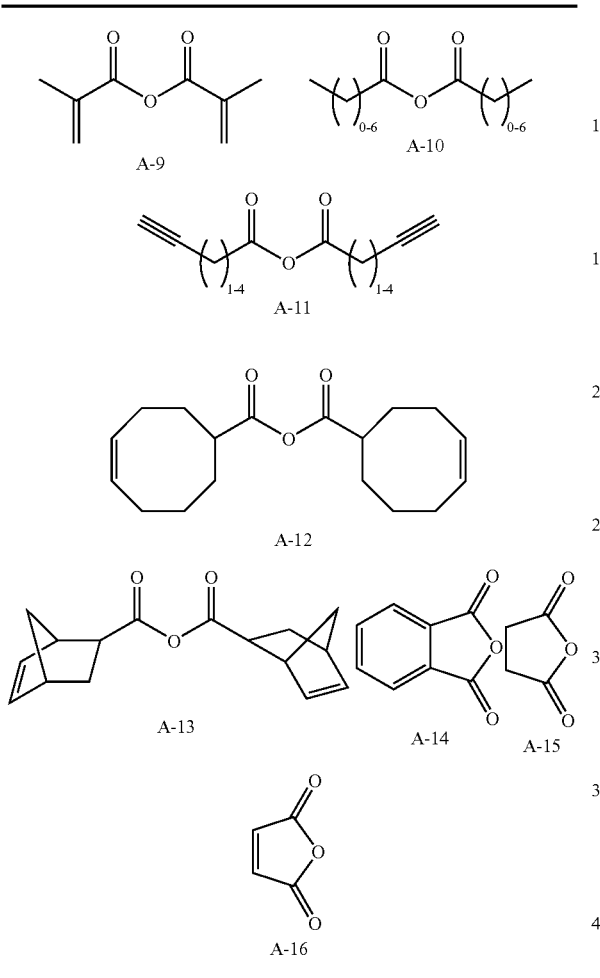

In other embodiments, the $R^4$ moiety of the $R^{2a}$ group of formula III is incorporated by derivatization of the amino group of formula I', or freebase thereof, via reaction with a polymerization terminating agent having a suitable leaving group. It will also be appreciated that such polymerization terminating agents are also suitable for terminating the living polymer chain-end of a compound of formula I', or freebase thereof. Examples of these polymerization terminating agents include, but are not limited to, those set forth in Table 11, below.

TABLE 11

Representative Polymerization Terminating Agents

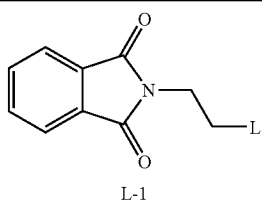

L-1

TABLE 11-continued

Representative Polymerization Terminating Agents

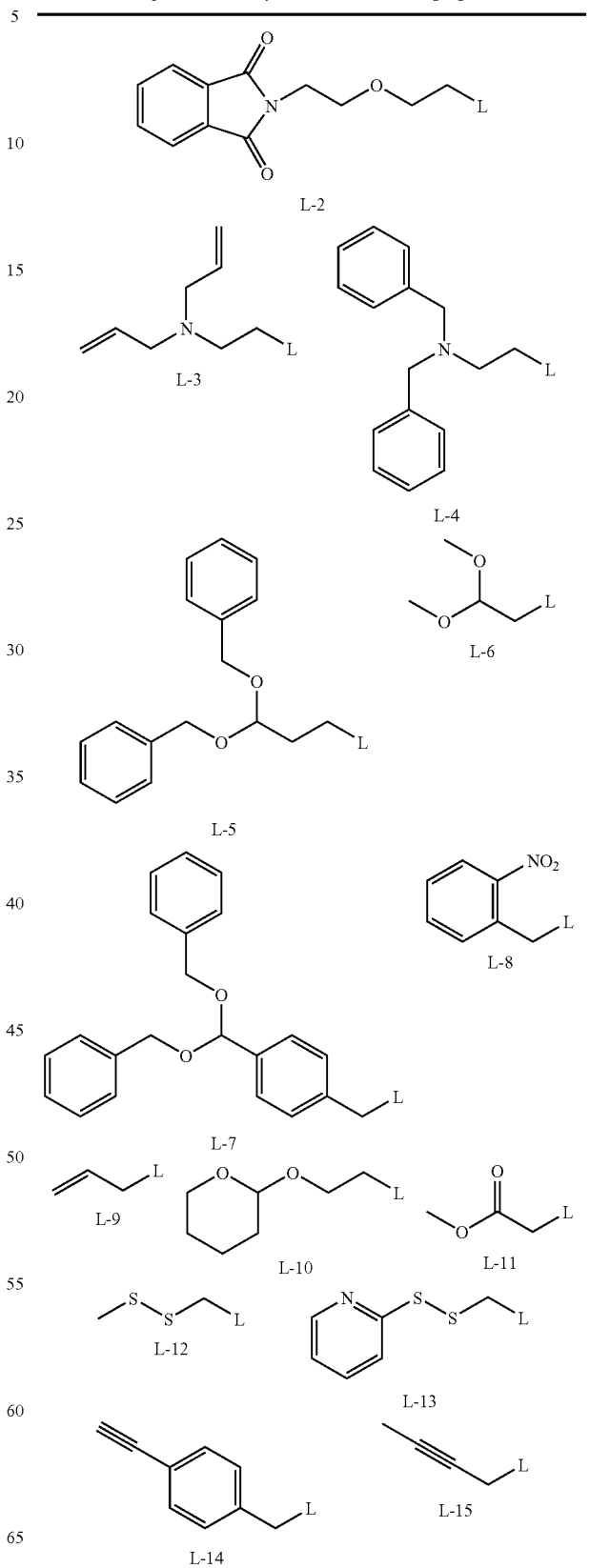

TABLE 11-continued

Representative Polymerization Terminating Agents

TABLE 11-continued

Representative Polymerization Terminating Agents

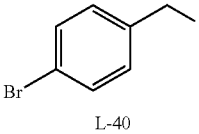

L-40

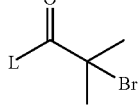

L-41

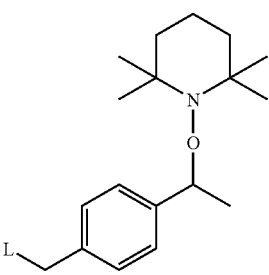

L-42 wherein each L is a suitable leaving group as defined above and in classes and subclasses as described above and herein.

In certain embodiments, the hydrophilic polymer block is poly(ethylene glycol) (PEG) having a terminal amine salt ("PEG macroinitiator"). This PEG macroinitiator initiates the polymerization of NCAs to provide the multiblock copolymers of the present invention. Such polymers having a terminal amine salt may be prepared from synthetic polymers having a terminal amine. Such synthetic polymers having a terminal amine group are known in the art and include PEG-amines. PEG-amines may be obtained by the deprotection of a suitably protected PEG-amine. Preparation of such suitably protected PEG-amines, and methods of deprotecting the same, is described in detail in U.S. patent application Ser. No. 11/256,735, filed Oct. 24, 2005 and published as US 20060142506 on Jun. 29, 2006, the entirety of which is hereby incorporated herein by reference.

As described in US 20060142506, suitably protected PEG-amines may be formed by terminating the living polymer chain end of a PEG with a terminating agent that contains a suitably protected amine. The suitably protected amine may then be deprotected to generate a PEG that is terminated with a free amine that may subsequently be converted into the corresponding PEG-amine salt macroinitiator. In certain embodiments, the PEG-amine salt macroinitiator of the present invention is prepared directly from a suitably protected PEG-amine by deprotecting said protected amine with an acid. Accordingly, in other embodiments, the terminating agent has suitably protected amino group wherein the protecting group is acid-labile.

Alternatively, suitable synthetic polymers having a terminal amine salt may be prepared from synthetic polymers that contain terminal functional groups that may be converted to amine salts by known synthetic routes. In certain embodiments, the conversion of the terminal functional groups to the amine salts is conducted in a single synthetic step. In other embodiments, the conversion of the terminal functional groups to the amine salts is achieved by way of a multi-step sequence. Functional group transformations that afford amines, amine salts, or protected amines are well known in the art and include those described in Larock, R. C., "Comprehensive Organic Transformations," John Wiley & Sons, New York, 1999.

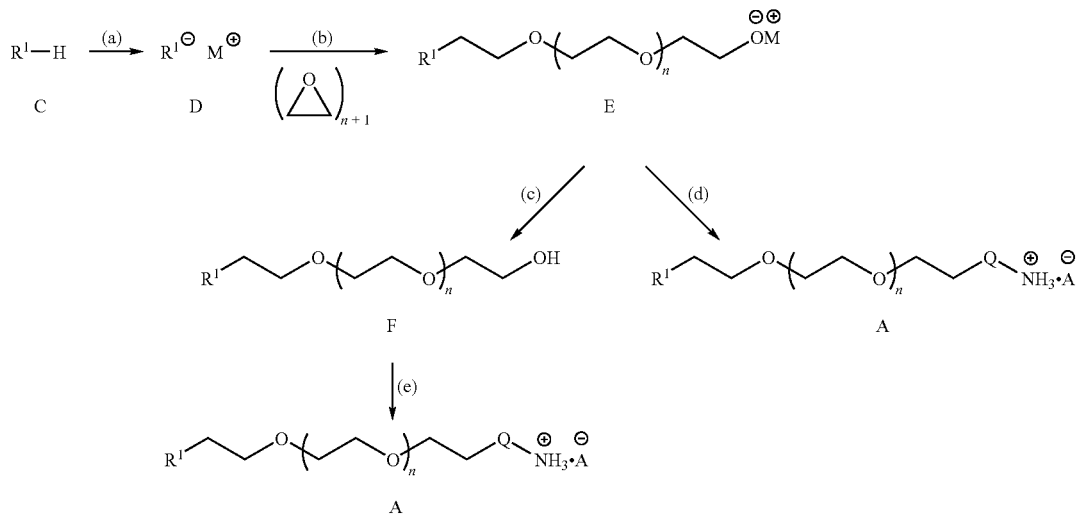

Scheme 7

Scheme 7 above shows one exemplary method for preparing the bifunctional PEGs used to prepare the multiblock copolymers of the present invention. At step (a), the polymerization initiator is treated with a suitable base to form D. A variety of bases are suitable for the reaction at step (a). Such bases include, but are not limited to, potassium naphthalenide, diphenylmethyl potassium, triphenylmethyl potassium, and potassium hydride. At step (b), the resulting anion is treated with ethylene oxide to form the polymer E. Polymer E can be transformed at step (d) to a compound of formula A directly by terminating the living polymer chain-end of E with a suitable polymerization terminator to afford a compound of formula A. Alternatively, polymer E may be quenched at step (c) to form the hydroxyl compound F. Compound F is then derivatized to afford a compound of formula A by methods known in the art, including those described herein. Each of the $R^1$, A, n, and Q groups depicted in Scheme 7 are as defined and described in classes and subclasses, singly and in combination, herein.

Although certain exemplary embodiments are depicted and described above and herein, it will be appreciated that compounds of the invention can be prepared according to the methods described generally above using appropriate starting materials by methods generally available to one of ordinary skill in the art. Additional embodiments are exemplified in more detail herein.

Methods of preparing micelles are known to one of ordinary skill in the art. Micelles can be prepared by a number of different dissolution methods. In the direct dissolution method, the block copolymer is added directly to an aqueous medium with or without heating and micelles are spontaneously formed up dissolution. The dialysis method is often used when micelles are formed from poorly aqueous soluble copolymes. The copolymer is dissolved in a water miscible organic solvent such as N-methyl pyrollidinone, dimethylformamide, dimethylsulfoxide, tetrahydrofuran, or dimethylacetamide, and this solution is then dialyzed against water or another aqueous medium. During dialysis, micelle formation is induced and the organic solvent is removed. Alternatively, the block copolymer can be dissolved in in a water miscible organic solvent such as N-methyl pyrollidinone, dimethylformamide, dimethylsulfoxide, tetrahydrofuran, or dimethylacetamide and added dropwise to water or another aqueous medium. The micelles can then be isolated by filtration or lyophilization.

Emulsification methods can also be employed for micelle formation. For example, the block copolymer is dissolved in a water-immiscible, volatile solvent (e.g. dichloromethane) and added to water with vigorous agitation. As the solvent is removed by evaporation, micelles spontaneously form. Prepared micelles can then be filtered and isolated by lyophilization.

In one embodiment, drug-loaded miclles possessing carboxylic acid functionality in the outer core are crosslinked by addition of zinc chloride to the micelle solution along with a small amount of sodium hydroxide to neutralize any hydrochloric acid by-product. In this basic pH environment, the reaction of zinc chloride with the poly(aspartic acid) crosslinking block should be rapid and irreversible.

In another embodiment, drug loaded micelles possessing amine functionality in the outer core are crosslinked by the addition of a bifunctional, or multi-functional aldehyde-containing molecule which forms pH-reversible imine crosslinks. In another embodiment, drug loaded micelles possessing aldehyde functionality in the outer core are crosslinked by the addition of a bifunctional, or multi-functional amine-containing molecule which forms pH-reversible imine crosslinks.

In another embodiment, drug loaded micelles possessing alcohol or amine functionality in the outer core are crosslinked by the addition of a bifunctional, or multi-functional carboxylic acid-containing molecules and a coupling agent to form amide or ester crosslinks. In yet another embodiment, drug loaded micelles possessing carboxylic acid functionality in the outer core are crosslinked by the addition of a bifunctional, or multi-functional amine or alcohol-containing molecules and a coupling agent to form amide or ester crosslinks. Such coupling agents include, but are not limited to, carbodiimides (e.g. 1-ethyl-3-(3-dimethylaminopropyl)-carbodiimide (EDC), diisopropyl carbodiimide (DIC), dicyclohexyl carbodiimide (DCC)), aminium or phosphonium derivatives (e.g. PyBOP, PyAOP, TBTU, HATU, HBTU), or a combination of 1-hydroxybenzotriazole (HOBt) and a aminium or phosphonium derivative.

In another embodiment, drug loaded micelles possessing aldehyde or ketone functionality in the outer core are crosslinked by the addition of a bifunctional, or multifunctional hydrazine or hydrazide-containing molecule to form pH-reversible hydrazone crosslinks. In still other embodiments, drug loaded micelles hydrazine or hydrazide-functionality in the outer core are crosslinked by the addition of a bifunctional, or multifunctional aldehyde or ketone-containing molecule to form pH-reversible hydrazone crosslinks.

In another embodiment, drug loaded micelles possessing thiol functionality in the outer core are crosslinked by the addition of an oxidizing agent (e.g. metal oxides, halogens, oxygen, peroxides, ozone, peroxyacids, etc.) to form disulfide crosslinks. It will be appreciated that disulfide crosslinks are reversible in the presence of a suitable reducing agent (e.g. glutathione, dithiothreitol (DTT), etc.).

In yet another embodiment, drug loaded micelles possessing both carboxylic acid and thiol functionality in the outer core can be dual crosslinked by the addition of an oxidizing agent (e.g. metal oxides, halogens, oxygen, peroxides, ozone, peroxyacids, etc.) to form disulfide crosslinks followed by the addition of zinc chloride to the micelle solution along with a small amount of sodium bicarbonate to neutralize any hydrochloric acid by-product. It will be appreciated that such a dual-crosslinked micelle is reversible only in the presence of acid and a reducing agent (e.g. glutathione, dithiothreitol (DTT), etc.).

According to another aspect, the present invention provides a method for preparing a micelle comprising a multiblock copolymer which comprises a polymeric hydrophilic block, optionally a crosslinkable or crosslinked poly(amino acid block), and a hydrophobic D,L-mixed poly(amino acid) block, characterized in that said micelle has an inner core, an optionally crosslinkable or crosslinked outer core, and a hydrophilic shell, said method comprising the steps of:

(a) providing a multiblock copolymer of formula I:

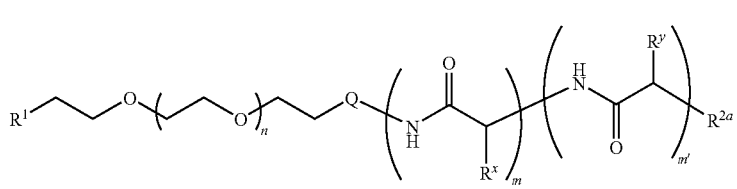

wherein each of the $R^1$, $R^{2a}$, Q, $R^x$, $R^y$, n, m, and m' groups of formula I, are as described in various classes and subclasses, both singly and in combination, herein, (b) combining said compound of formula I with a therapeutic agent; and (c) treating the resulting micelle with a crosslinking reagent to crosslink $R^x$.

In one embodiment, drugs are loaded into the micelle inner core by adding an aliquot of a copolymer solution in water to the drug to be incorporated. For example, a stock solution of the drug in a polar organic solvent is made and allowed to evaporate, and then the copolymer/water solution is added. In another embodiment, the drug is incorporated using an oil in water emulsion technique. In this case, the drug is dissolved in an organic solvent and added dropwise to the micelle solution in water, and the drug is incorporated into the micelle during solvent evaporation. In another embodiment, the drug is dissolved with the copolymer in a common polar organic solvent and dialyzed against water or another aqueous medium. See Allen, C.; Maysinger, D.; Eisenberg A. *Colloid Surface B* 1999, 16, 3-27.

In still another embodiment, the loading and crosslinking of drug-filled micelles is carried out by dissolving neutral doxorubicin, camptothecin, docetaxel, or paclitaxel and the block copolymer in a polar solvent such as acetone or ethanol, followed by slow addition to water or buffer solution. Due to the limited solubility of these agents in water, the drug is forced into the core of the micelle, effectively encapsulating the drug.

5. Uses, Methods, and Compositions

As described herein, micelles of the present invention can encapsulate a wide variety of therapeutic agents useful for treating a wide variety of diseases. In certain embodiments, the present invention provides a drug-loaded micelle, as described herein, wherein said micelle is useful for treating the disorder for which the drug is known to treat. According to one embodiment, the present invention provides a method for treating one or more disorders selected from pain, inflammation, arrhythmia, arthritis (rheumatoid or osteoarthritis), atherosclerosis, restenosis, bacterial infection, viral infection, depression, diabetes, epilepsy, fungal infection, gout, hypertension, malaria, migraine, cancer or other proliferative disorder, erectile dysfunction, a thyroid disorder, neurological disorders and hormone-related diseases, Parkinson's disease, Huntington's disease, Alzheimer's disease, a gastro-intestinal disorder, allergy, an autoimmune disorder, such as asthma or psoriasis, osteoporosis, obesity and comorbidities, a cognitive disorder, stroke, AIDS-associated dementia, amyotrophic lateral sclerosis (ALS, Lou Gehrig's disease), multiple sclerosis (MS), schizophrenia, anxiety, bipolar disorder, tauopothy, a spinal cord or peripheral nerve injury, myocardial infarction, cardiomyocyte hypertrophy, glaucoma, an attention deficit disorder (ADD or ADHD), a sleep disorder, reperfusion/ischemia, an angiogenic disorder, or urinary incontinence, comprising administering to a patient a micelle comprising a multiblock copolymer which comprises a polymeric hydrophilic block, optionally a crosslinkable or crosslinked poly(amino acid block), and a hydrophobic D,L-mixed poly(amino acid block), characterized in that said micelle has a drug-loaded inner core, optionally a crosslinkable or crosslinked outer core, and a hydrophilic shell, wherein said micelle encapsulates a therapeutic agent suitable for treating said disorder.

In other embodiments, the present invention provides a method for treating one or more disorders selected from autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease, comprising administering to a patient a multiblock copolymer which comprises a polymeric hydrophilic block, optionally a crosslinkable or crosslinked poly(amino acid block), and a hydrophobic D,L-mixed poly(amino acid block), characterized in that said micelle has a drug-loaded inner core, optionally a crosslinkable or crosslinked outer core, and a hydrophilic shell, wherein said micelle encapsulates a therapeutic agent suitable for treating said disorder.

In certain embodiments, drug-loaded micelles of the present invention are useful for treating cancer. Accordingly, another aspect of the present invention provides a method for treating cancer in a patient comprising administering to a patient a multiblock copolymer which comprises a polymeric hydrophilic block, optionally a crosslinkable or crosslinked poly(amino acid block), and a hydrophobic D,L-mixed poly(amino acid block), characterized in that said micelle has a drug-loaded inner core, optionally a crosslinkable or crosslinked outer core, and a hydrophilic shell, wherein said micelle encapsulates a chemotherapeutic agent. According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia, comprising administering a micelle in accordance with the present invention wherein said micelle encapsulates a chemotherapeutic agent suitable for treating said cancer.

P-glycoprotein (Pgp, also called multidrug resistance protein) is found in the plasma membrane of higher eukaryotes where it is responsible for ATP hydrolysis-driven export of hydrophobic molecules. In animals, Pgp plays an important role in excretion of and protection from environmental toxins; when expressed in the plasma membrane of cancer cells, it can lead to failure of chemotherapy by preventing the hydrophobic chemotherapeutic drugs from reaching their targets inside cells. Indeed, Pgp is known to transport hydrophobic chemotherapeutic drugs out of tumor cells. According to one aspect, the present invention provides a method for delivering a hydrophobic chemotherapeutic drug to a cancer cell while preventing, or lessening, Pgp excretion of that chemotherapeutic drug, comprising administering a drug-loaded micelle comprising a multiblock polymer of the present invention loaded with a hydrophobic chemotherapeutic drug. Such hydrophobic chemotherapeutic drugs are well known in the art and include those described herein.

Compositions

According to another embodiment, the invention provides a composition comprising a micelle of this invention or a pharmaceutically acceptable derivative thereof and a pharmaceutically acceptable carrier, adjuvant, or vehicle. In certain embodiments, the composition of this invention is formulated for administration to a patient in need of such composition. In other embodiments, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In certain embodiments, pharmaceutically acceptable compositions of the present invention are enterically coated.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the drug can be administered to a patient receiving these compositions.

It will be appreciated that dosages typically employed for the encapsulated drug are contemplated by the present invention. In certain embodiments, a patient is administered a drug-loaded micelle of the present invention wherein the dosage of the drug is equivalent to what is typically administered for that drug. In other embodiments, a patient is administered a drug-loaded micelle of the present invention wherein the dosage of the drug is lower than is typically administered for that drug.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

In order that the invention described herein may be more fully understood, the following examples are set forth. It will be understood that these examples are for illustrative purposes only and are not to be construed as limiting this invention in any manner.

EXEMPLIFICATION

Preparation of Bifunctional PEGs and Multiblock Copolymers of the Present Invention As described generally above, multiblock copolymers of the present invention are prepared using the heterobifunctional PEGs described herein and in U.S. patent application Ser. No. 11/256,735, filed Oct. 24, 2005, published as WO2006/047419 on May 4, 2006 and published as US 20060142506 on Jun. 29, 2006, the entirety of which is hereby incorporated herein by reference. The preparation of multiblock polymers in accordance with the present invention is accomplished by methods known in the art, including those described in detail in U.S. patent application Ser. No. 11/325,020, filed Jan. 4, 2006, published as WO2006/74202 on Jul. 13, 2006 and published as US 20060172914 on Aug. 3, 2006, the entirety of which is hereby incorporated herein by reference.

In each of the Examples below, where an amino acid, or corresponding NCA, is designated "D", then that amino acid, or corresponding NCA, is of the D-configuration. Where no such designation is recited, then that amino acid, or corresponding NCA, is of the L-configuration.

Example 1

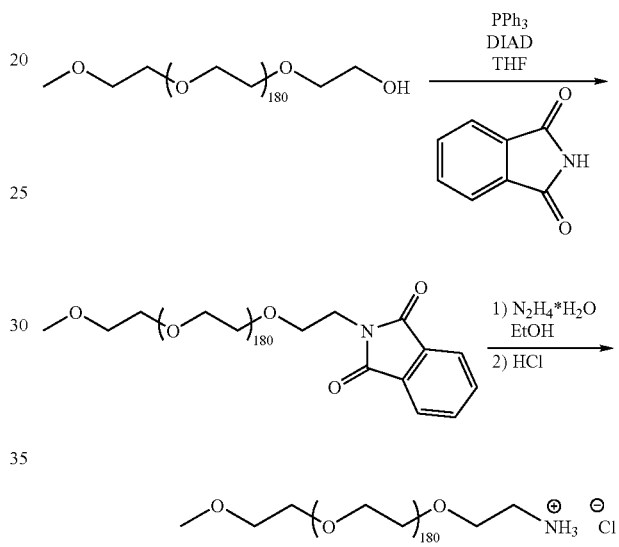

Synthesis of mPEG-hydrochloride—To a 500 mL 2-neck round bottom flask was added mPEG (40 g, 5 mmol), phthalimide (4.41 g, 30 mmol) and triphenyl phosphine (6.55 g, 25 mmol). The reagents were dissolved in anhydrous THF (300 mL) and stirred at room temperature. Once a homogeneous solution was present, DIAD (4.04 g, 20 mmol) was added and the solution stirred for 16 h. The solvent was evaporated and the residue purified by solid phase extraction (3% MeOH in $CHCl_3$ (1 L) followed by 10% MeOH in $CHCl_3$ (1 L) which contained the polymer product). The solvent was removed and the resulting liquid dissolved in ethanol (200 mL) and hydrazine hydrate (10 mL). The solution was stirred at reflux for 14 h, allowed to cool, then concentrated HCl (15 mL) was added dropwise to the solution. The solution was filtered and the solvent evaporated. The residue was dissolved in water and the polymer product extracted with $CHCl_3$ (4×500 mL). The combined organic layers were dried over $MgSO_4$, filtered and the solvent evaporated. The resulting liquid was diluted with a minimal amount of methanol and precipitated in to diethyl ether. A white powder (28.2 g, 71%) was isolated following filtration. $^1H$ NMR (400 MHz, DMSO-$d_6$, δ) 7.79 br-s, 3.7-3.3 br-m, 2.96 t. GPC (DMF, PEG standards) $M_n$=7,800; PDI=1.03.

Example 2

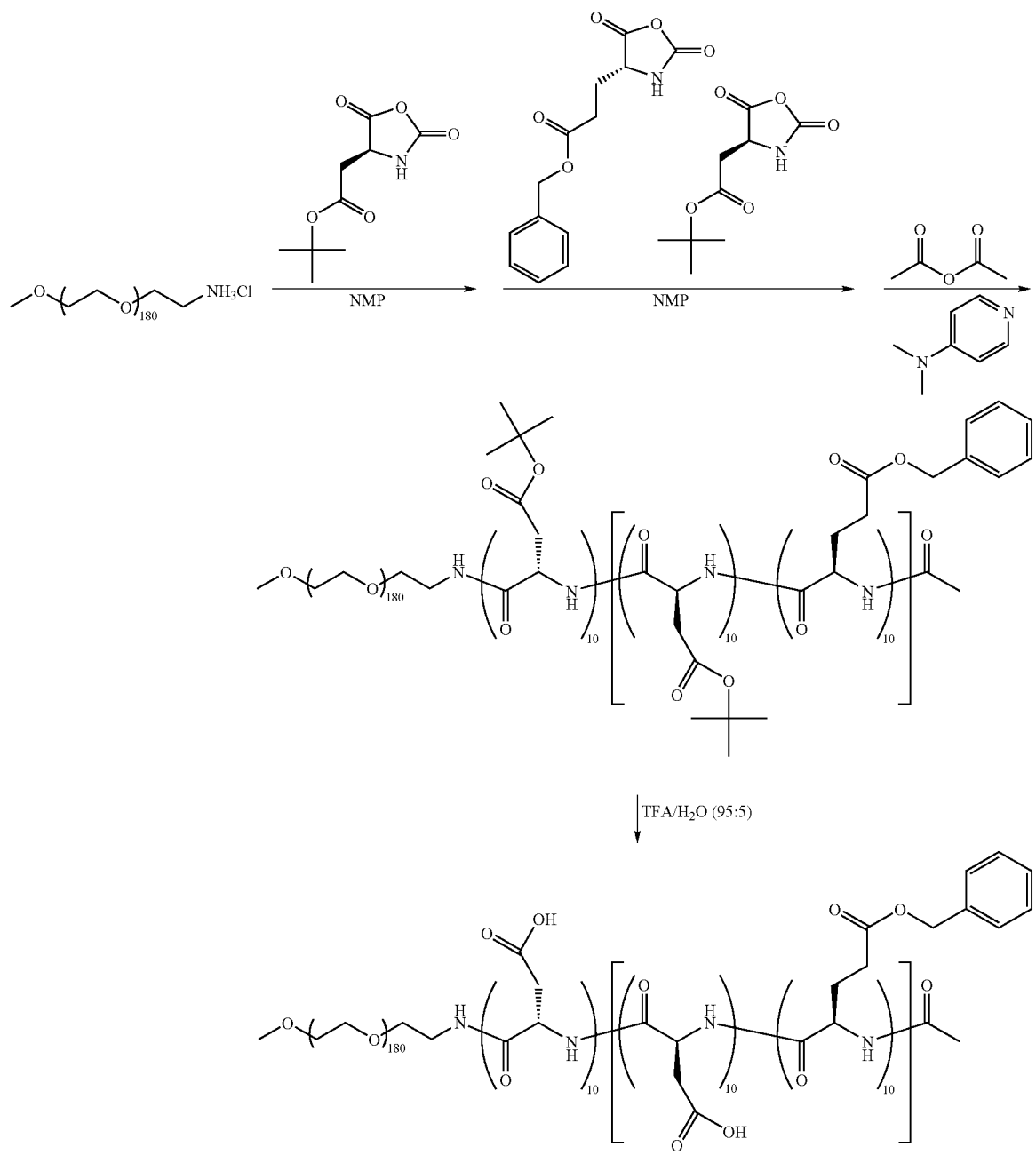

Synthesis of mPEG-PAsp-(PAsp-co-DBzGlu)-Ac—To a 100 mL round bottom flask was added mPEG-hydrochloride (1.0 g, 0.13 mmol) and t-butyl aspartic acid NCA (0.28 g, 1.3 mmol). The reagents were dried under vacuum for 1 hour, then NMP (10 mL) added. The solution was degassed under vacuum the backfilled with $N_2$, and stirred at 80° C. After 48 h, D-benzyl glutamate NCA (0.34 g, 1.3 mmol) and t-butyl aspartic acid NCA (0.28 g, 1.3 mmol) was dissolved in NMP (5 mL) and added to the reaction. After an additional 48 h, the solution was allowed to cool, then DMAP (0.16 g, 1.3 mmol) and acetic anhydride (0.13 g, 1.3 mmol) added to the stirred solution. After 1 hour, the solution was precipitated into diethyl ether/hexanes (3:2, 300 mL). A white solid was recovered after filtration, which was dissolved in TFA/$H_2O$ (95:5, 40 mL) and stirred for 4 hours at room temperature. The solvent was evaporated and the residue precipitated into ether (300 mL). A white powder (0.7 g, 52% yield) was recovered following filtration. $^1$H NMR (400 MHz, DMSO-$d_6$, δ) 12.37, 8.23, 7.97, 7.55, 7.34, 6.97, 5.06, 4.51, 4.27, 3.7-3.3, 3.19, 2.67, 2.35, 2.01, 1.83.

Example 3

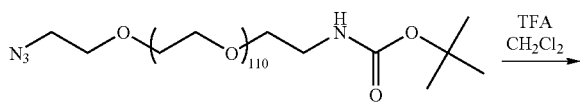

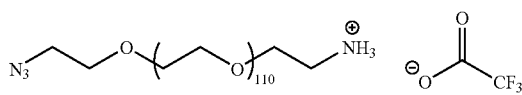

Synthesis of Azide-PEG-TFA salt—Azide-PEG-BOC was dissolved in 1:1 TFA/CH$_2$Cl$_2$ (15 mL) and stirred at room temperature for 1 hour. The solvent was evaporated and the residue precipitated into ether. A white powder was recovered by filtration, which was redissolved in a minimal amount of methanol (40 mL) and again precipitated into ether. A white powder (2.6 g, 87% yield) was recovered after filtration. $^1$H NMR (400 MHz, DMSO-d$_6$, δ) 7.72, 3.3-3.7, 2.98. GPC (DMF, PEG Standards) M$_n$=4,800; PDI=1.04.

Example 4

Synthesis of Azide-PEG-P(D/LBzGlu)-Ac—To a 100 mL round bottom flask was added Azide-PEG-TFA salt (1.89 g, 0.38 mmol), D-benzyl glutamate NCA (1 g, 3.8 mmol), and L-benzyl glutamate NCA (1 g, 3.8 mmol). The reagents were dried under vacuum for 1 hour, then NMP (40 mL) added. The solution was degassed under vacuum the backfilled with N$_2$, and stirred at 60° C. After 24 h, the solution was allowed to cool, then DMAP (0.16 g, 1.3 mmol), pyridine (1 mL) and acetic anhydride (1 mL) added to the stirred solution. After 1 hour, the solution was precipitated into diethyl ether/hexanes (3:2, 300 mL). A white powder (1.9 g, 54% yield) was recovered following filtration. $^1$H NMR (400 MHz, DMSO-d$_6$, δ) 9.08, 8.01, 7.35, 5.08, 4.47, 4.23, 3.3-3.7, 2.68, 2.15, 1.81.

Example 5

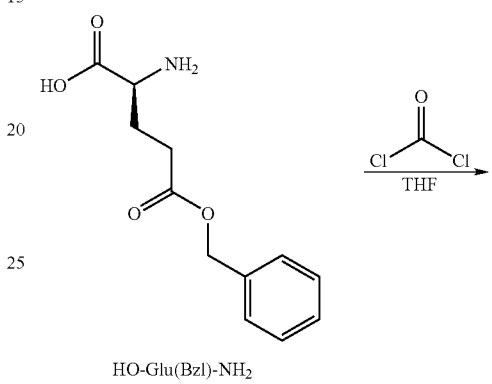

HO-Glu(Bzl)-NH$_2$

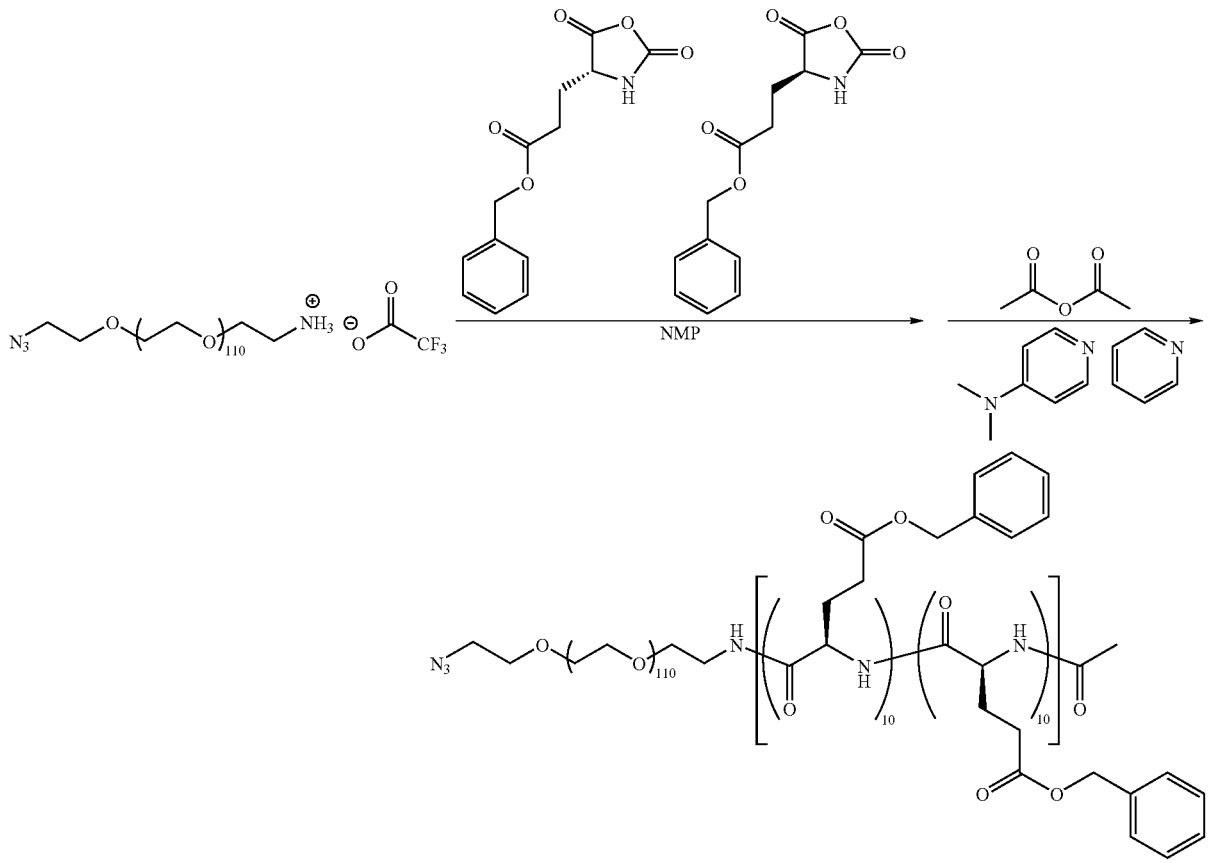

-continued

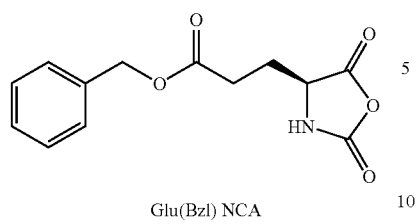

Glu(Bzl) NCA

Synthesis of Glu(Bzl) NCA—HO-Glu(Bzl)-NH$_2$ (30.0 g, 126.0 mmol) was suspended in 300 mL of anhydrous THF and heated to 50° C. Phosgene (20% in toluene) (81.3 mL, 164.6 mmol) was added to the amino acid suspension by syringe, and the amino acid dissolved over the course of approx. 30 minutes, forming a clear solution. The solution was concentrated by rotory evaporation, dissolved in ~150 mL of anhydrous THF, and transferred to an Erlenmeyer flask. Hexane was added and the product was allowed to crystallize overnight. The NCA was isolated by filtration and dried in vacuo. 29.8 g (90% yield) of Glu(Bzl) NCA was isolated as a white, crystalline solid. $^1$H NMR (CDCl$_3$) δ 7.36 (5H), 6.22 (1H), 5.14 (2H), 4.35 (1H), 2.61 (2H), 2.29 (1H), 2.14 (1H) ppm.

Example 6

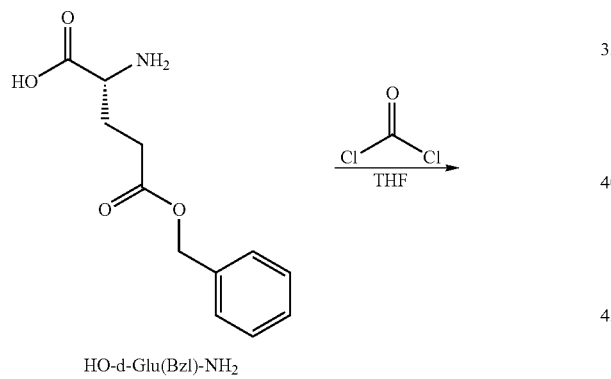

HO-d-Glu(Bzl)-NH$_2$ d-Glu(Bzl) NCA

Synthesis of d-Glu(Bzl) NCA—d-Glu(Bzl) NCA was synthesized as described in Example 3 from HO-d-Glu(Bzl)-NH$_2$ (30.7 g, 129.2 mmol) and 83.1 mL (168.0 mmol) of phosgene (20% in toluene). 31.8 g (94% yield) of product was isolated as a white, crystalline solid. $^1$H NMR (CDCl$_3$) δ 7.36 (5H), 6.22 (1H), 5.14 (2H), 4.35 (1H), 2.61 (2H), 2.29 (1H), 2.14 (1H) ppm.

Example 7

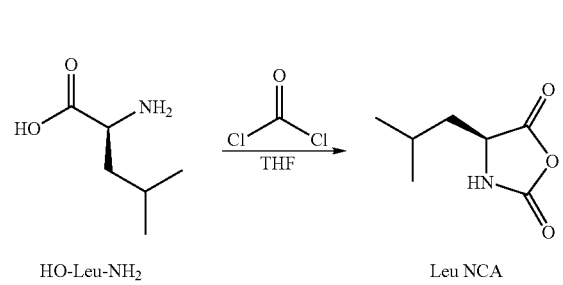

HO-Leu-NH$_2$    Leu NCA

Synthesis of Leu NCA—HO-Leu-NH$_2$ (10.0 g, 76.2 mmol) was suspended in 150 mL of anhydrous THF and heated to 50° C. Phosgene (20% in toluene) (76.0 mL, 152.4 mmol) was added to the amino acid suspension. The amino acid dissolved over the course of approx. 1 hr, forming a clear solution. The solution was concentrated on the rotovap, transferred to a beaker, and hexane was added to precipitate the product. The white solid was isolated by filtration and dissolved in toluene. The solution was filtered over a bed of Celite to remove any insoluble material. An excess of hexane was added to the filtrate to precipitate the product. The NCA was isolated by filtration and dried in vacuo. 9.0 g (75% yield) of Leu NCA was isolated as a white, crystalline solid. $^1$H NMR (d$_6$-DMSO) δ 9.13 (1H), 4.44 (1H), 1.74 (1H), 1.55 (2H), 0.90 (6H) ppm.

Example 8

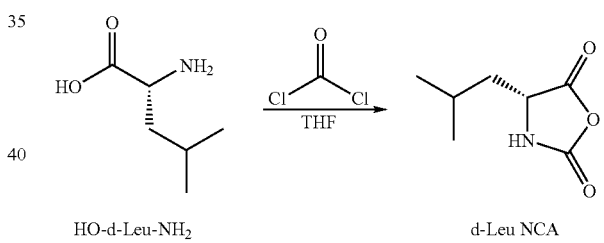

HO-d-Leu-NH$_2$    d-Leu NCA

Synthesis of d-Leu NCA—d-Leu NCA was synthesized as described in Example 1 from HO-d-Leu-NH$_2$ (20.0 g, 152.5 mmol) and 99.3 mL (198.3 mmol) of phosgene (20% in toluene). 13.8 g (58% yield) of NCA was isolated as a white, crystalline solid. $^1$H NMR (d$_6$-DMSO) δ 9.13 (1H), 4.44 (1H), 1.74 (1H), 1.55 (2H), 0.90 (6H) ppm.

Example 9

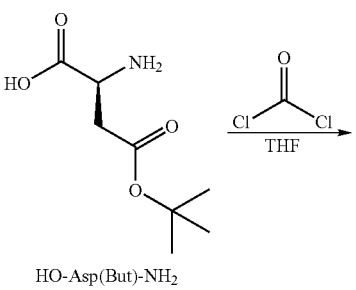

HO-Asp(But)-NH$_2$

-continued

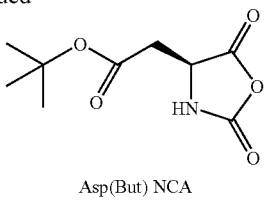

Asp(But) NCA

Synthesis of Asp(But) NCA—HO-Asp(But)-NH$_2$ (20.0 g, 105.7 mmol) was suspended in 300 mL of anhydrous THF and heated to 50° C. Phosgene (20% in toluene) (105 mL, 211.4 mmol) was added to the amino acid suspension, and the amino acid dissolved over the course of approx. 1 hr, forming a clear solution. The solution was concentrated on by rotary evaporation, transferred to a beaker, and hexane was added to precipitate the product. The white solid was isolated by filtration and dissolved in anhydrous THF. The solution was filtered over a bed of Celite to remove any insoluble material. An excess of hexane was added on the top of the filtrate and the bilayer solution was left in the freezer overnight. The NCA was isolated by filtration and dried in vacuo. 15.0 g (66% yield) of Asp(But) NCA was isolated as a white, crystalline solid. $^1$H NMR (d$_6$-DMSO) δ 8.99 (1H), 4.61 (1H), 2.93 (1H), 2.69 (1H), 1.38 (9H) ppm.

Example 10

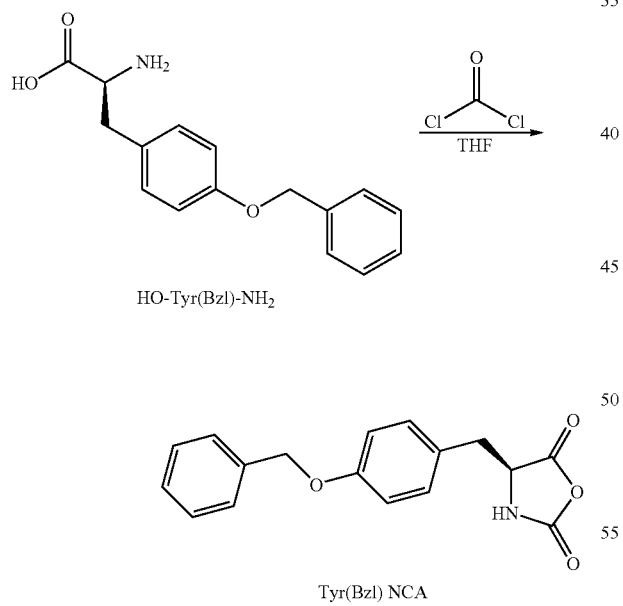

HO-Tyr(Bzl)-NH$_2$

Tyr(Bzl) NCA

Synthesis of Tyr(Bzl) NCA—HO-Tyr(Bzl)-NH$_2$ (20.0 g, 105.7 mmol) was suspended in 300 mL of anhydrous THF and heated to 50° C. Phosgene (20% in toluene) (73.7 mL, 147.4 mmol) was added the amino acid suspension. The amino acid dissolved over the course of approx. 1 hr, forming a pale yellow solution. The solution was concentrated on the rotovap, transferred to a beaker, and hexane was added to precipitate the product. The off-white solid was isolated by filtration and dissolved in anhydrous THF. The solution was stirred over carbon black and subsequently filtered over a bed of Celite. An excess of hexane was added to the filtrate to precipitate the product. The NCA was isolated by filtration and dried in vacuo. 14.3 g (65% yield) of Tyr(Bzl) NCA was isolated as a off-white, solid. $^1$H NMR (d$_6$-DMSO) δ 9.07 (1H), 7.49-7.29 (5H), 7.12-7.07 (2H), 6.98-6.94 (2H), 5.06 (2H), 4.74 (1H), 3.05-2.88 (2H) ppm.

Example 11

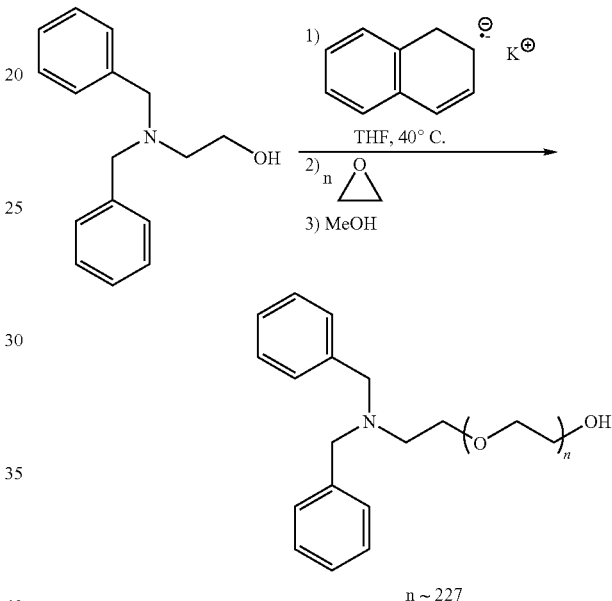

n ~ 227

Synthesis of (Dibenzyl)-N-PEG10K-OH—N,N-dibenzyl-2-aminoethanol (4.3 g, 17.6 mmol) was weighed into an oven-dried 2 L jacketed, round-bottom flask. An oven-dried jacketed addition funnel was attached to the reaction flask and three vacuum/argon cycles was applied to the setup. Anhydrous tetrahydrofuran (THF) (1.2 L) was introduced to the round bottom flask directly from a solvent purification system under an overpressure of argon. N,N-dibenzyl-2-aminoethanol was then converted to N,N-dibenzyl-2-aminoethoxide by titration by potassium naphthalenide (0.2 M solution into THF) until a dark green color persisted in solution for a few seconds. Ethylene oxide (184.0 ml, 4.0 mol) was condensed at −30° C. in the jacketed addition funnel and subsequently added to the alkoxide solution which had been cooled to −1° C. The reactor was pressurized with argon and sealed and then warmed to 10° C. and stirred for 4 hours, then warmed to 20° C. and stirred for 12 hours, and then warmed to 40° C. and stirred for 3 days. An excess of methanol was used to terminate the polymerization. The solution was concentrated by rotary evaporation and used as such for deprotection of the amine end-group (see Example 12). $^1$H NMR (d$_6$-DMSO) δ 7.4-7.2 (10H), 4.55 (1H), 3.83-3.21 (910 H) ppm

Example 12

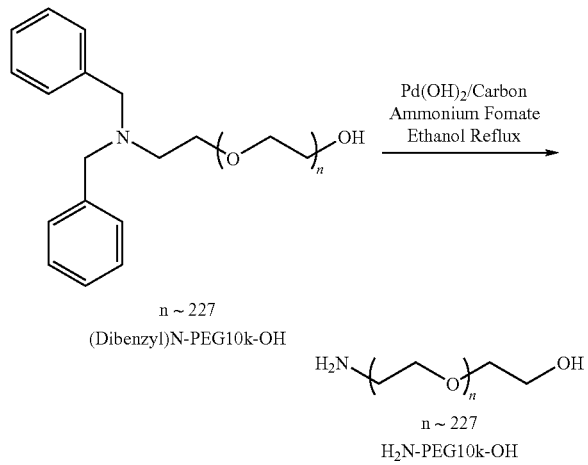

Synthesis of H₂N-PEG10K-OH—(Bzl)₂-N-PEG10K-OH (176.0 g, 17.6 mmol), Pd(OH)₂/C (32.0 g, 45.6 mmol), ammonium formate (80.0 g, 1.3 mol), and ethanol (1.2 L) were combined in a 2 L round-bottom flask, heated to 80° C., and stirred overnight. The reaction was cooled to room temperature and potassium carbonate (5 g) was added and stirred for 30 min. The solution was filtered through a bed of Celite and concentrated by rotary evaporation. The white solid was then dissolved in 800 ml of a 50/50 brine/saturated potassium carbonate mixture and extracted three times with dichloromethane. Dichloromethane fractions were combined, dried over MgSO₄, concentrated to a volume of approximately 800 ml by rotary evaporation and used as-is for Boc protection (see Example 13). ¹H NMR (d₆-DMSO) 4.55 (1H), 3.83-3.21 (910 H), 2.96 (2H) ppm

Example 13

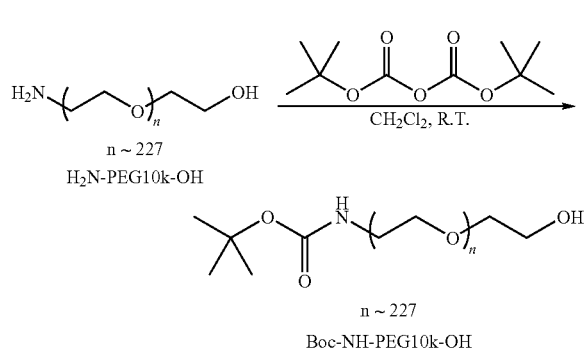

Reaction of di-tert-butyl dicarbonate with H₂N-PEG10K-OH—Di-tert-butyl dicarbonate (38.4 g, 176.0 mmol) was added to a solution of H₂N-PEG10K-OH (175 g, 17.5 mmol) in dichloromethane (~800 mL) and allowed to stir at room temperature overnight. The resulting product was concentrated by rotary evaporation and purified via silica gel chromatography (97/3→85/15 dichloromethane/methanol). The PEG containing fractions were combined, concentrated by rotary evaporation, and precipitated into a 10-fold excess of diethyl ether. The product was isolated by filtration and dried in vacuo to give 104 g (59% yield) of Boc-HN-PEG10K—OH as an off-white powder. ¹H NMR (d₆-DMSO) δ 6.75 (1H), 4.55 (1H), 3.83-3.21 (910 H), 3.06 (2H), 1.37 (9H) ppm

Example 14

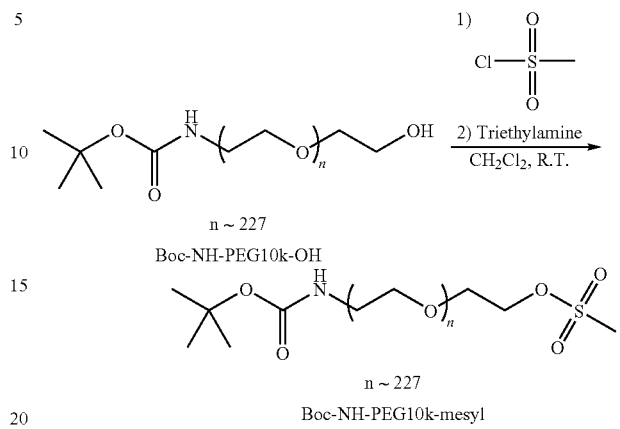

Synthesis of Boc-HN-PEG10K-Mesylate—BocHN-PEG10K-OH (104 g, 10.4 mmol) was dried by azeotropic distillation from toluene and dissolved in 600 mL of dry dichloromethane under nitrogen. The solution was cooled to 0° C. using an ice/water bath and methanesulfonyl chloride (2.4 mL, 31.2 mmol) was added by syringe. Triethylamine (2.9 mL, 20.8 mmol) was subsequently added by syringe and the reaction was allowed to warm to room temperature and stirred overnight. The solution was evaporated to dryness by rotary evaporation and used as-is for sodium azide substitution (see Example 11). ¹H NMR (d₆-DMSO) δ 6.75 (1H), 4.36 (2H), 3.83-3.21 (910 H), 3.06 (2H), 1.37 (9H) ppm.

Example 15

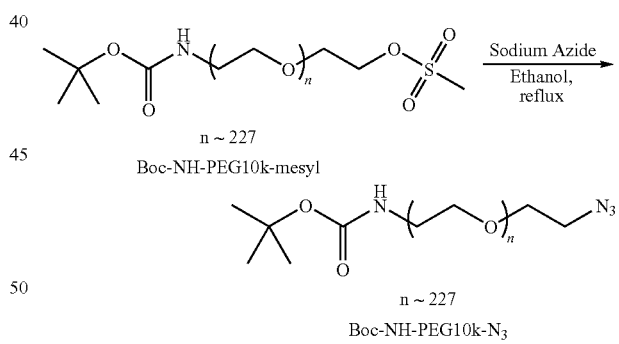

Synthesis of Boc-NH-PEG10K-N₃—BocHN-PEG10K-Mesylate (~104 g, 10.4 mmol) and sodium azide (6.8 g, 104.0 mmol) were dissolved in 800 mL ethanol, heated to 80° C., and stirred overnight. After cooling to room temperature, the contents were concentrated to dryness by rotary evaporation and dissolved in 250 mL of dichloromethane. The product was subsequently purified by silica gel chromatography (97/3→85/15 dichloromethane/methanol). The PEG containing fractions were combined, concentrated by rotary evaporation, and precipitated into a 10-fold excess of diethyl ether. The polymer was isolated by filtration as a white powder (90 g, 86% yield). ¹H NMR (d₆-DMSO) δ 6.75 (1H), 3.83-3.21 (910 H), 3.06 (2H), 1.37 (9H) ppm.

Example 16

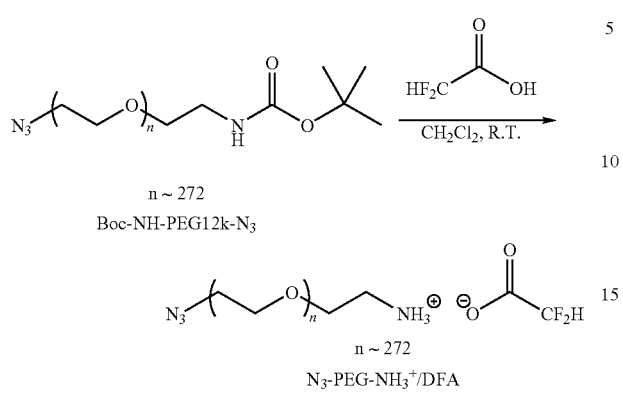

Synthesis of $N_3$-PEG12K-$NH_3$ DFA salt—$N_3$-PEG12K-NHBoc (15.0 g, 1.3 mmol) was dissolved in 100 mL of a $CH_2Cl_2$/DFA solution (70/30) and was allowed to stir at room temperature overnight. The product was precipitated into diethyl ether, dissolved in dichloromethane, and reprecipitated into diethyl ether. The product was isolated by filtration and dried in vacuo to yield 13.5 g (90% yield) of an off-white powder. $^1$H NMR ($d_6$-DMSO) 7.77 (3H), 5.97 (1H), 3.83-3.21 (1050 H), 2.98 (2H) ppm

Example 17

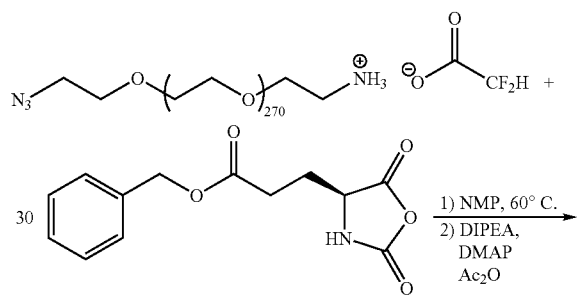

Synthesis of $N_3$-PEG12K-b-P(L-Glu(Bzl)$_{30}$)-Ac—$N_3$-PEG-$NH_3$ DFA salt, 12 kDa (5.0 g, 0.42 mmol) was weighed into an oven-dried, round-bottom flask, dissolved in toluene, and dried by azeotropic distillation. Excess toluene was removed under vacuum. L-Glu(Bzl) NCA (3.3 g, 12.5 mmol) was added to the flask, the flask was evacuated under reduced pressure, and subsequently backfilled with nitrogen gas. Dry N-methylpyrrolidone (NMP) (42.0 mL) was introduced by syringe and the solution was heated to 60° C. The reaction mixture was allowed to stir for 96 hours at 60° C. under nitrogen gas. The solution was cooled to room temperature and diisopropylethylamine (DIPEA) (1.0 mL), dimethylaminopyridine (DMAP) (100 mg), and acetic anhydride (1.0 mL) were added. Stirring was continued for 1 hour at room temperature. The polymer was precipitated into diethyl ether and isolated by filtration. The solid was then dissolved in dichloromethane and reprecipitated into diethyl ether. The product was isolated by filtration and dried in vacuo to give 6.5 g (86% yield) of block copolymer as an off-white powder. $^1$H NMR (400 MHz, DMSO-$d_6$, δ) 7.9-8.4, 7.35, 5.04, 4.25, 3.10-3.90, 1.75-2.60 ppm.

Example 18

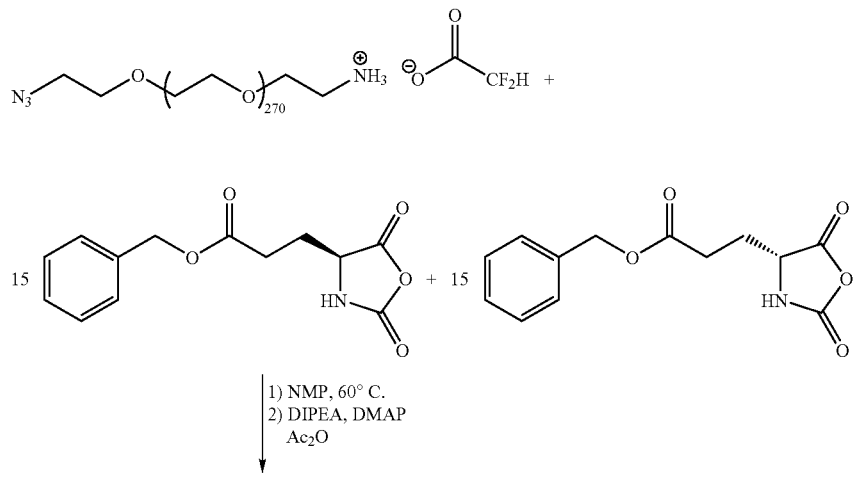

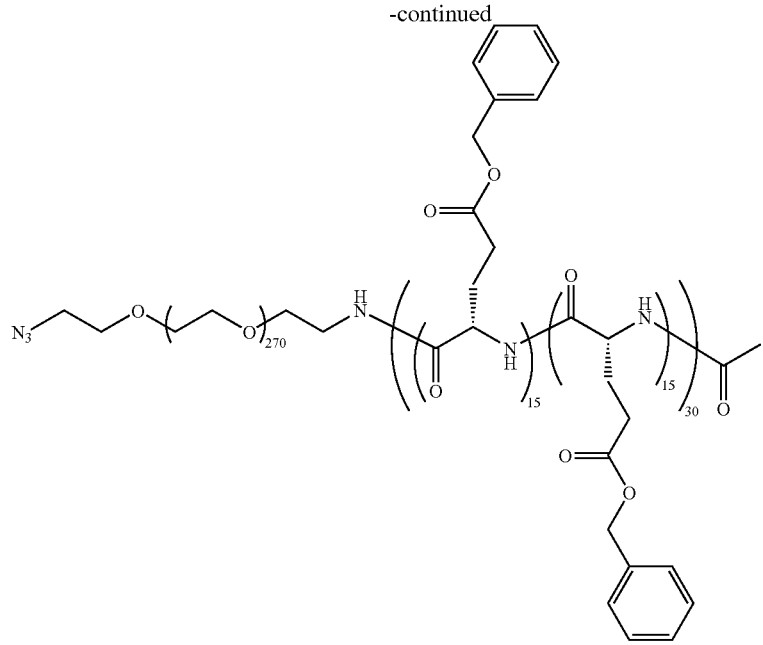
Synthesis of N₃-PEG12K-b-Poly(L-Glu(Bzl))₁₅-co-D-Glu(Bzl))₁₅)-Ac—N₃-PEG12K-b-Poly(L-Glu(Bzl))₁₅-co-D-Glu(Bzl))₁₅) was synthesized as described in Example 13 from N₃-PEG-NH₃ DFA salt, 12 kDa (5.0 g, 0.42 mmol), L-Glu(Bzl) NCA (1.7 g, 6.3 mmol), and D-Glu(Bzl) NCA (1.7 g, 6.3 mmol). 6.2 g (82% yield) of block copolymer was isolated as an off-white powder. $^1$H NMR (d$_6$-DMSO) δ 8.10, 7.30, 5.03, 4.30, 3.30-3.70, 2.33, 1.75-2.00 ppm.
Example 19
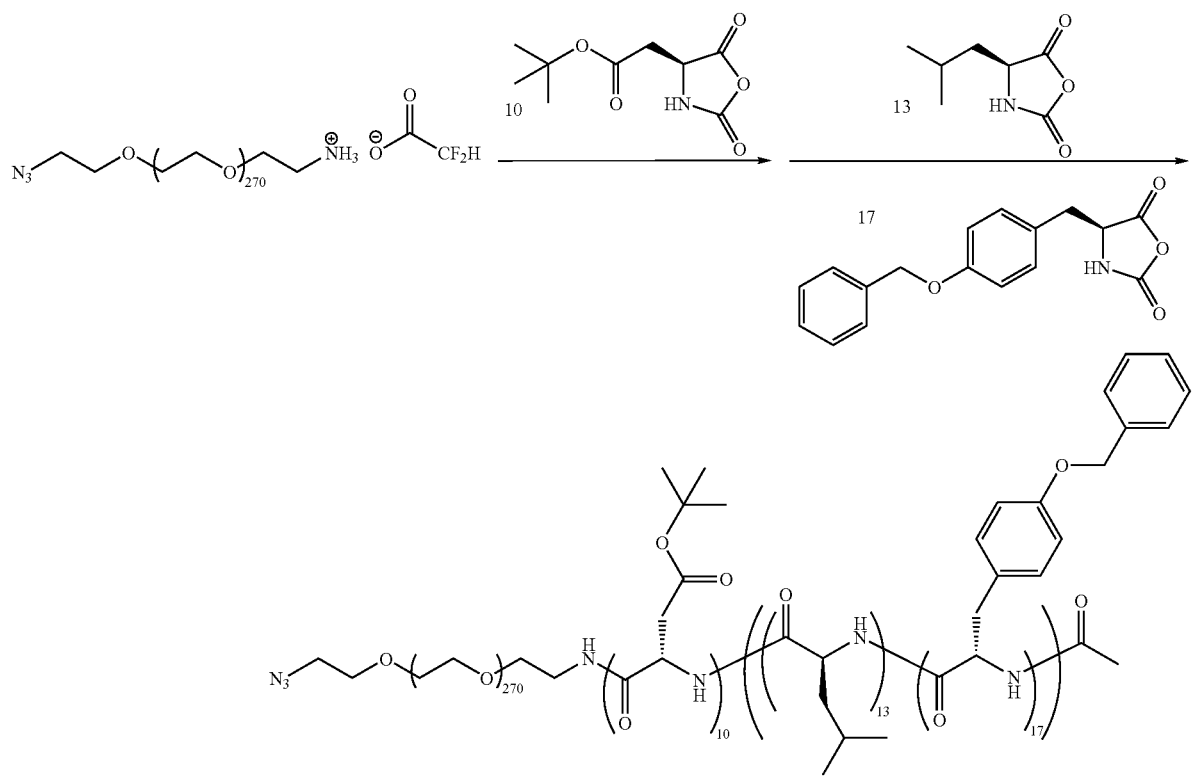

Synthesis of $N_3$-PEG12K-b-Poly(Asp(But)$_{10}$)-b-Poly(L-Leu$_{13}$-co-L-Tyr(Bzl)$_{17}$)-Ac—$N_3$-PEG-$NH_3$ DFA salt, 12 kDa (5.0 g, 0.42 mmol) was weighed into an oven-dried, round-bottom flask, dissolved in toluene, and dried by azeotropic distillation. Excess toluene was removed under vacuum. Asp(But) NCA (0.9 g, 4.2 mmol) was added to the flask, the flask was evacuated under reduced pressure, and backfilled with nitrogen gas. Dry NMP (29.0 mL) was introduced by syringe and the solution was heated to 60° C. The reaction mixture was allowed to stir for 36 hours at 60° C. under nitrogen gas. In an oven-dried round-bottom flask, L-Leu NCA (0.9 g, 5.4 mmol) and Tyr(Bzl) NCA (2.1 g, 7.1 mmol) were combined and dissolved in 15 ml of dry NMP under nitrogen gas. This solution was then transferred to the polymerization by syringe and allowed to stir for an additional 72 hours at 60° C. under nitrogen gas. The solution was cooled to room temperature and DIPEA (1.0 mL), DMAP (100 mg), and acetic anhydride (1.0 mL) were added. Stirring was continued for 1 hour at room temperature. The polymer was precipitated into diethyl ether and isolated by filtration. The solid was then dissolved in dichloromethane and reprecipitated into diethyl ether. The product was isolated by filtration and dried in vacuo to give 7.6 g (94% yield) of block copolymer as an off-white powder. $^1$H NMR (400 MHz, DMSO-$d_6$, δ) 7.80-8.40, 6.60-7.40, 4.95, 4.40, 3.2-3.7, 2.70, 1.36, 0.80 ppm.

Example 20

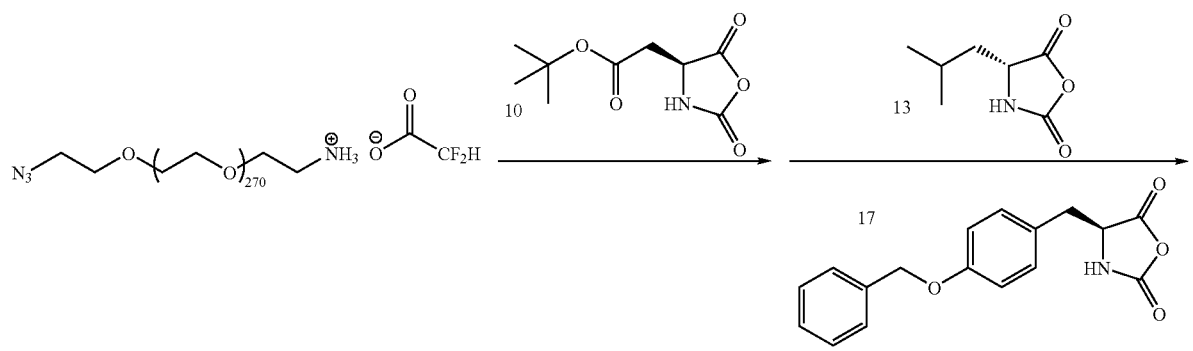

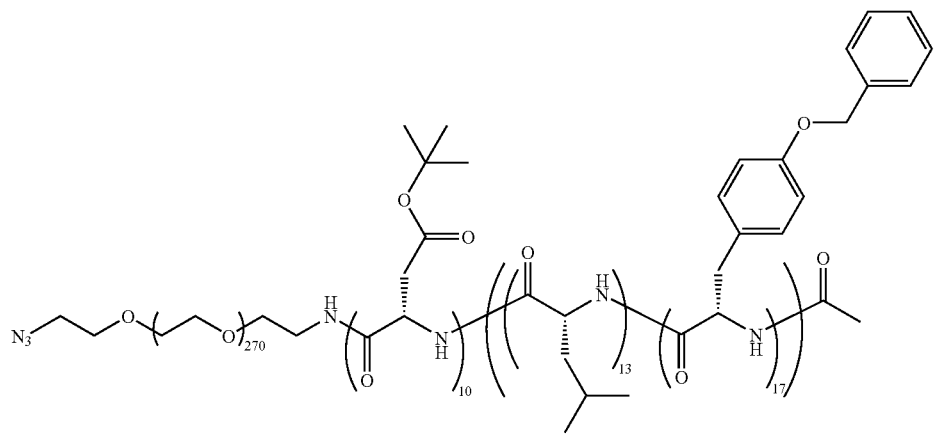

Synthesis of N₃-PEG12K-b-Poly(Asp(But)₁₀)-b-Poly(D-Leu₁₃-co-L-Tyr(Bzl)₁₇)-Ac N₃-PEG12K-b-Poly(Asp(But))₁₀-b-Poly(D-Leu₁₃-co-L-Tyr(Bzl)₁₇) was synthesized as described in Example 15 from N₃-PEG-NH₃ DFA salt, 12 kDa (5.0 g, 0.42 mmol), Asp(But) NCA (0.9 g, 4.2 mmol), D-Leu NCA (0.9 g, 5.4 mmol), and Tyr(Bzl) NCA (2.1 g, 7.1 mmol). 7.1 g (88% yield) of block copolymer was isolated as an off-white powder. ¹H NMR (d₆-DMSO) δ 7.70-8.40, 7.35, 7.09, 6.82, 4.96, 4.50, 4.00-4.20, 3.20-3.7, 2.90, 2.70, 1.36, 0.40-0.90 ppm.

Example 21 mL of a 0.5 M solution of pentamethyl-benzene (PMB) in trifluoroacetic acid (TFA). The reaction was allowed to stir for 2.5 hours at room temper-ature with precipitate forming after approximately 1 hour. The polymer was precipitated into diethyl ether, filtered, dissolved in dichloromethane, and reprecipitated into diethyl ether. The product was isolated by filtration and dried in vacuo to 5.3 g (79% yield) of block copolymer as an off-white powder. ¹H NMR (d₆-DMSO) δ

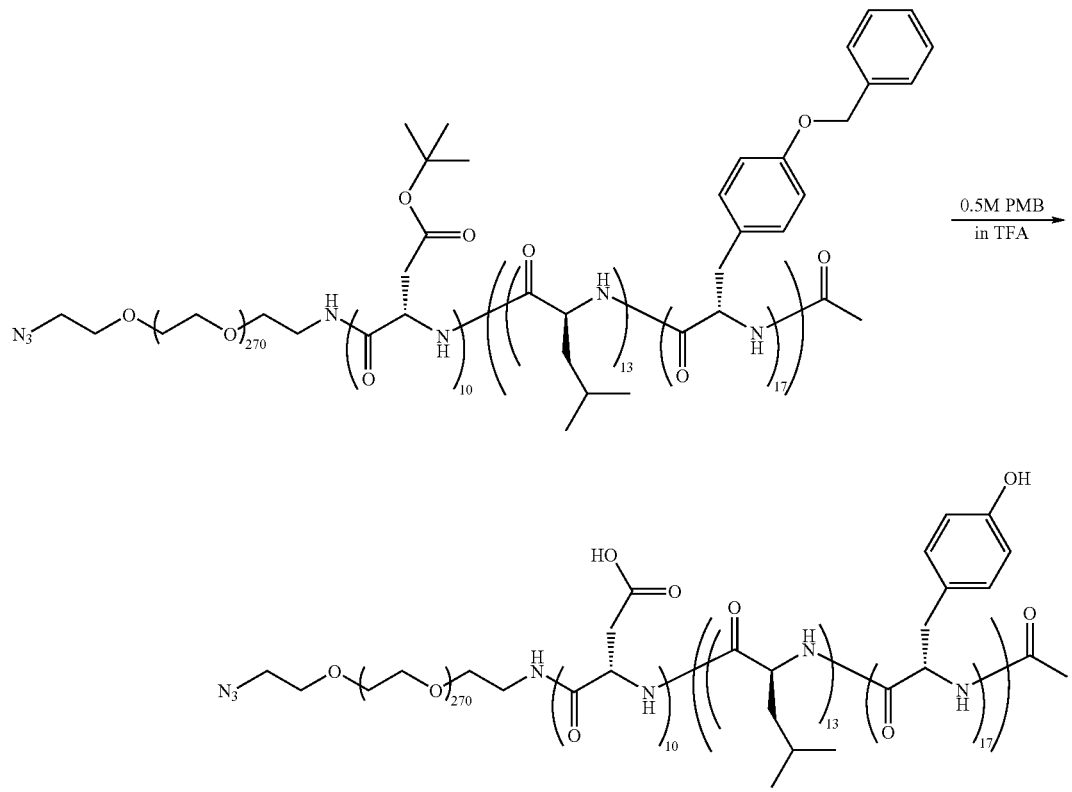

Synthesis of N₃-PEG12K-b-Poly(Asp)₁₀-b-Poly(L-Leu₁₃-co-L-Tyr₁₇)-Ac N₃-PEG12K-b-Poly(Asp(But)₁₀)-b-Poly(L-Leu₁₃-co-L-Tyr(Bzl)₁₇) (7.55 g) was dis-solved in 80

12.35, 9.15, 7.60-8.60, 7.00, 6.60, 4.50, 3.20-3.70, 2.85, 1.40-2.00, 0.82 ppm.

Example 22

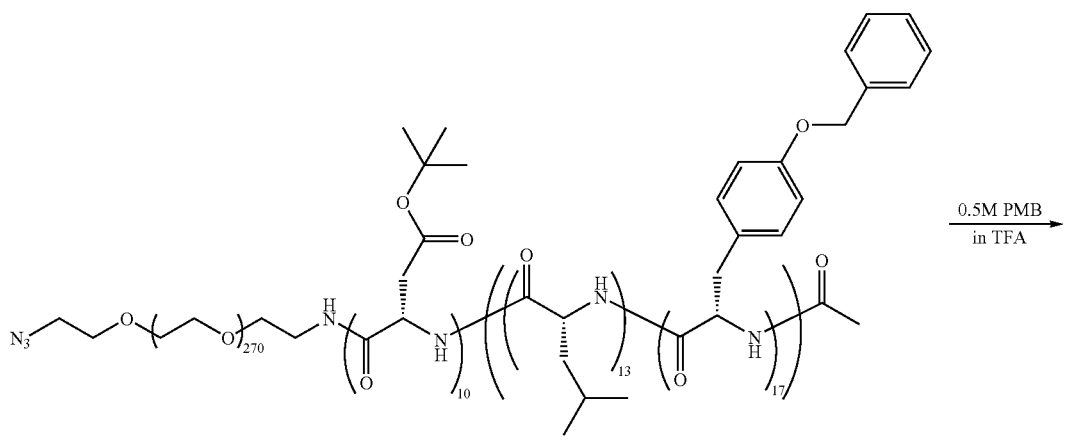

-continued

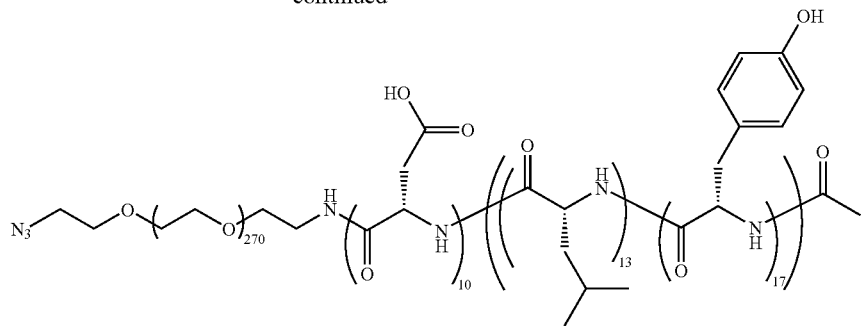

Synthesis of N$_3$-PEG12K-b-Poly(Asp)$_{10}$-b-Poly(D-Leu$_{13}$-co-L-Tyr$_{17}$)-Ac N$_3$-PEG12K-b-Poly(Asp)$_{10}$-b-Poly(D-Leu$_{13}$-co-L-Tyr$_{17}$) was synthesized as described in Example 21 from N$_3$-PEG12K-b-Poly(Asp(But)$_{10}$)-b-Poly(D-Leu$_{13}$-co-L-Tyr(Bzl)$_{17}$) (7.05 g) and 80 mL of a 0.5 M solution of pentamethylbenzene (PMB) in TFA. 5.9 g (94% yield) of block copolymer was isolated as an off-white powder. $^1$H NMR (d$_6$-DMSO) δ 12.35, 9.10, 7.60-8.60, 6.96, 6.60, 4.50, 4.40, 4.10-4.25, 3.20-3.70, 2.85, 2.70, 0.40-1.40 ppm.

Example 23

Figure 2:
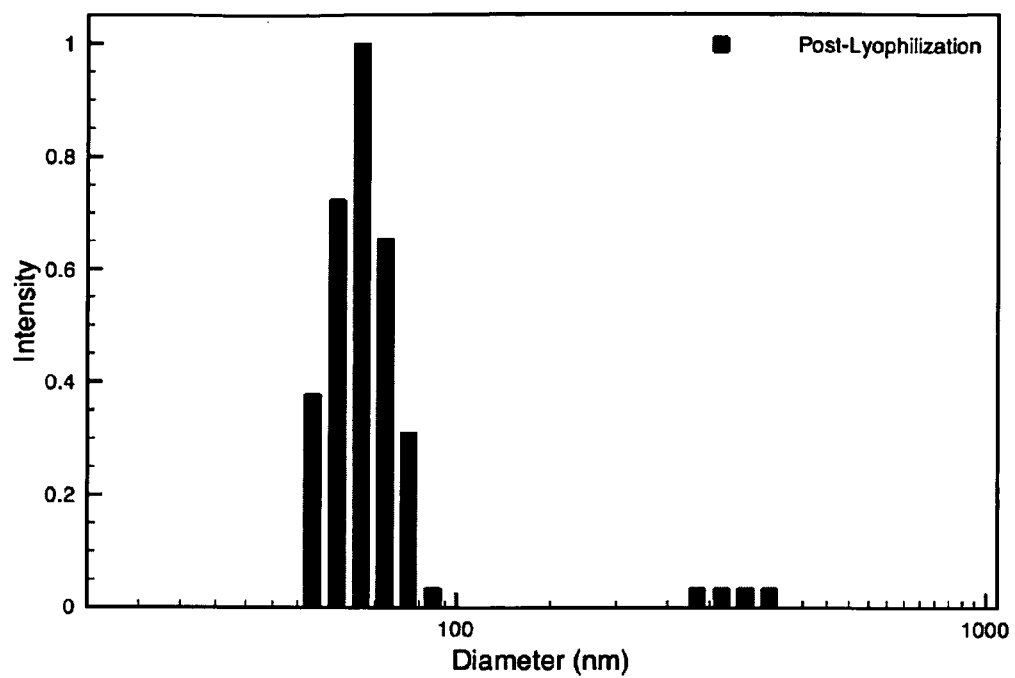
FIG. 2 depicts the results of dynamic light scattering of $Fe_2O_3$ encapsulated micelles.

Encapsulation of Fe$_3$O$_4$—A solution consisting of 4 nm Fe$_3$O$_4$ nanoparticles (2.5 mg) (prepared according to Sun, S.; Zeng, H. "Size-Controlled Synthesis of Magnetite Nanoparticles" *J. Am. Chem. Soc.* 2002, 124, 8204-8205.) and mPEG-PAsp-(PAsp-co-DBzGlu)-Ac (25 mg) dissolved in CHCl$_3$ (1 mL) was added dropwise to a vortexing flask containing water (20 mL). The mixture was vortexed until a homogenous solution was formed. The homogenous solution was analyzed by dynamic light scattering (FIG. 1) then lyophilized and the dry powder was stored at 4° C. A small portion of the powder (5 mg) was reconstituted in water (1 mL) and again analyzed by dynamic light scattering (FIG. 2). Diameter=60+/−8.8 nm pre-lyophilization, 65+/−9.7 nm post-lyophilization.

Example 24

Encapsulation of Fe$_3$O$_4$—A solution consisting of 4 nm Fe$_3$O$_4$ nanoparticles (1.25 mg) in CHCl$_3$ (1 mL) was added dropwise to a vortexing flask containing mPEG-PAsp-(PAsp-co-DBzGlu)-Ac (25 mg) dissolved in water (20 mL). The mixture was vortexed until a homogenous solution was formed. The homogenous solution was lyophilized and the dry powder was stored at 4° C.

Example 25

Figure 3:
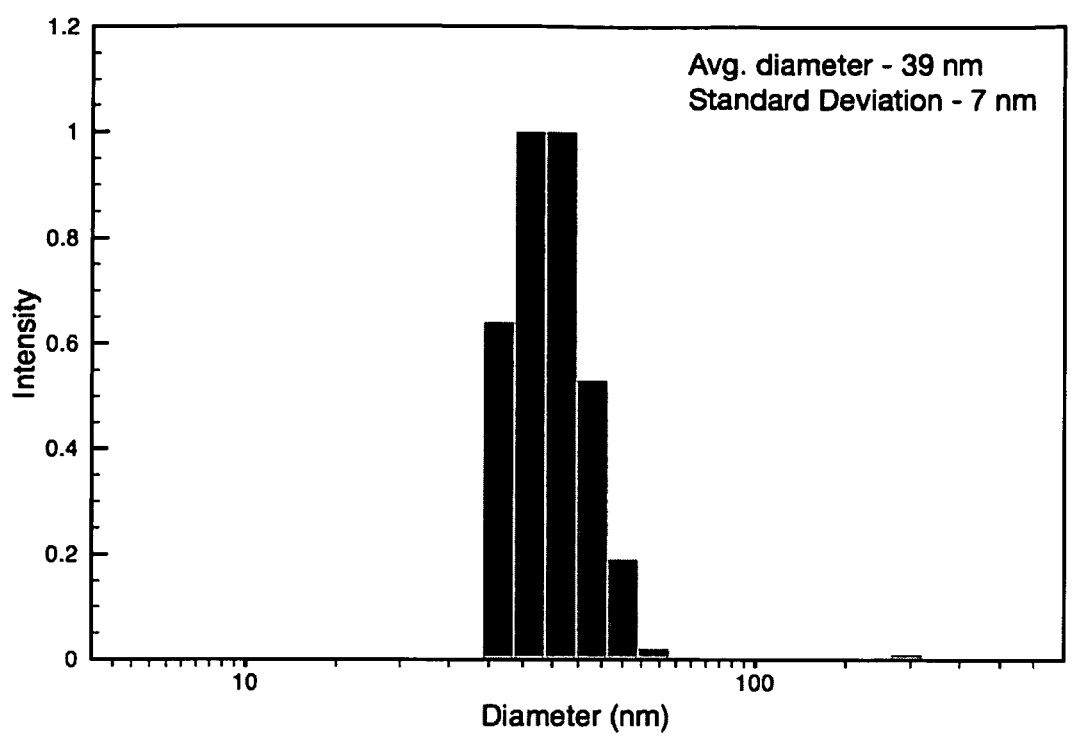
FIG. 3 depicts the results of dynamic light scattering of Docetaxel encapsulated micelles.

Encapsulation of Docetaxel—A solution consisting of Docetaxel (2.5 mg) and mPEG-PAsp-(PAsp-co-DBzGlu)-Ac (25 mg) dissolved in CHCl$_3$ (1 mL) was added dropwise to a vortexing flask containing water (20 mL). The mixture was vortexed until a homogenous solution was formed. The homogenous solution was lyophilized and the dry powder was stored at 4° C. A small portion of the powder (5 mg) was reconstituted in water and again analyzed by dynamic light scattering (FIG. 3). Diameter=39+/−7 nm post-lyophilization.

Example 26

Encapsulation of Docetaxel—A solution consisting of Docetaxel (1.25 mg) in CHCl$_3$ was added dropwise to a vortexing flask containing mPEG-PAsp-(PAsp-co-DBzGlu)-Ac (25 mg) dissolved in water (20 mL). The mixture was vortexed until a homogenous solution was formed. The homogenous solution was lyophilized and the dry powder was stored at 4° C.

Example 27

Encapsulation of Fe$_3$O$_4$—A solution consisting of 4 nm Fe$_3$O$_4$ nanoparticles (1.25 mg) in CHCl$_3$ was added dropwise to a vortexing flask containing mPEG-PAsp-(PAsp-co-DBzGlu)-Ac (25 mg) dissolved in $10^{-4}$ ZnCl$_2$ aqueous solution (20 mL). The mixture was vortexed until a homogenous solution was formed. The homogenous solution was lyophilized and the dry powder was stored at 4° C.

Example 28

Figure 4:
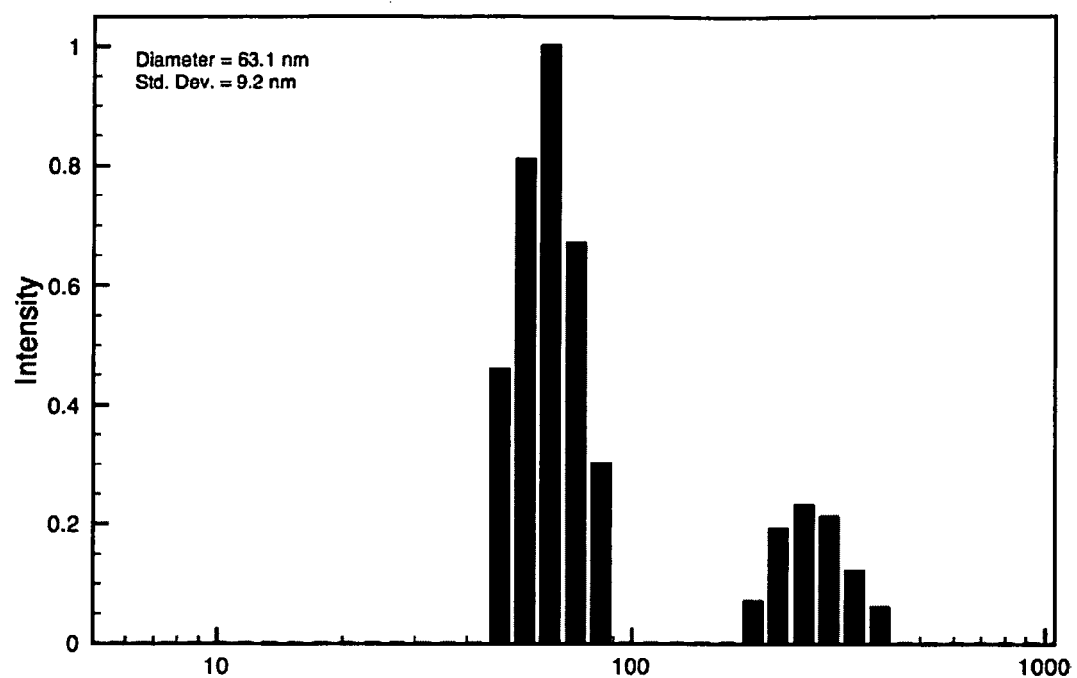
FIG. 4 depicts the results of dynamic light scattering of Letrozole encapsulated micelles.

Encapsulation of Letrozole—A solution consisting of Letrozole (1.25 mg) in CHCl$_3$ was added dropwise to a vortexing flask containing mPEG-PAsp-(PAsp-co-DBzGlu)-Ac (25 mg) dissolved in water (20 mL). The mixture was vortexed until a homogenous solution was formed. The homogenous solution was lyophilized and the dry powder was stored at 4° C. A small portion of the powder (5 mg) was reconstituted in water and again analyzed by dynamic light scattering (FIG. 4). Diameter=63.1+/−9.2 nm post-lyophilization.

Example 29

Cell Culture—MCF-7, BT474, LNCaP, amd MG-63 cells were maintained in RPMI 1640 supplemented with 10% FBS, 2 mM L-glutamine, 100 IU penilcillin/mL and 100 µg/mL streptomycin/mL. MDA-MB-231 and Saos2 cells were maintained in DMEM with 10% FBS, 2 mM L-glutamine 100 IU penicillin/mL and 100 µg/mL streptomycin/mL. MCF10A cells were maintained in a 50:50 mix of DMEM and Ham's F12 supplemented with 5% FBS, 2 mM L-glutamine, 10 ng/mL EGF, 500 ng/mL hydrocortisone, 0.01 mg/mL insulin, 100 IU penicillin/mL and 100 µg/mL streptomycin/mL. Cells were maintained at 37 degrees Celsius with 5% CO2 and were subcultured weekly.

Figure 5:
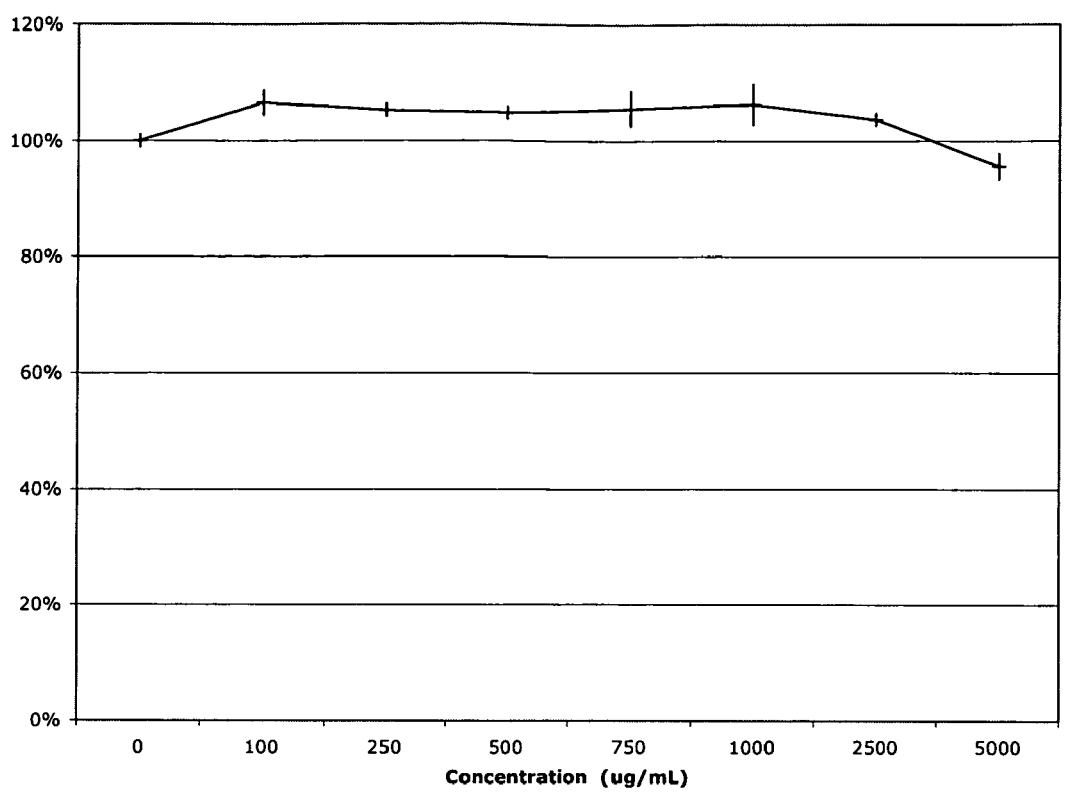
FIG. 5 depicts the results of a cytotoxicity assay on a micelle of the present invention.

Polymer cytotoxicity Assay—$1.2\times10^4$ MDA-MB-231 cells were plated in 96-well plates. Twenty-four hours later, media was replaced with micelle diluted in growth media at a final concentration of 0, 100, 250, 500, 750, 1000, 2500 or 5000 µg/mL mPEG-PAsp-(PAsp-co-DBzGlu)-Ac. After 72 hours, cell viability was determined using the Cell-Titer Glo reagent according to the manufacturer's protocol (Promega, Madison, Wis.). Data were collected using a plate reader with luminescence detection (BMG Labtech, Durham, N.C.). Experiments were performed in triplicate and shown in FIG. 5.

Example 30

Figure 6:
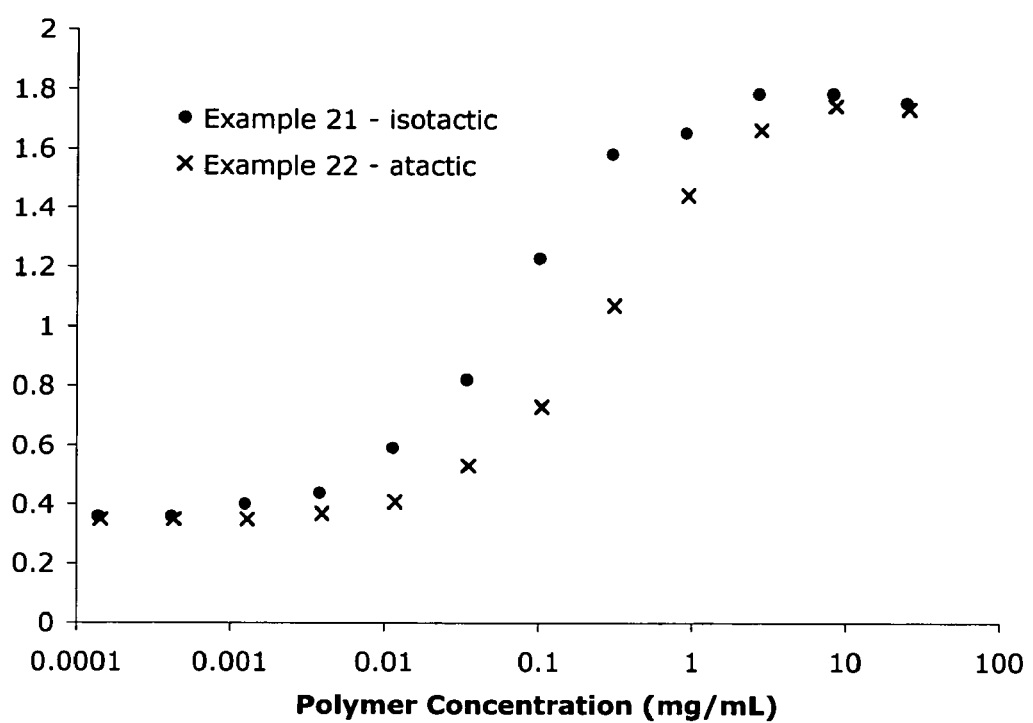
FIG. 6 depicts the CMC curves of $N_3$-PEG12K-b-Poly$(Asp)_{10}$-b-Poly(L-Leu$_{13}$-co-L-Tyr$_{17}$)-Ac (Example 21) and $N_3$-PEG12K-b-Poly$(Asp)_{10}$-b-Poly(D-Leu$_{13}$-co-L-Tyr$_{17}$)-Ac (Example 22).
Figure 7:
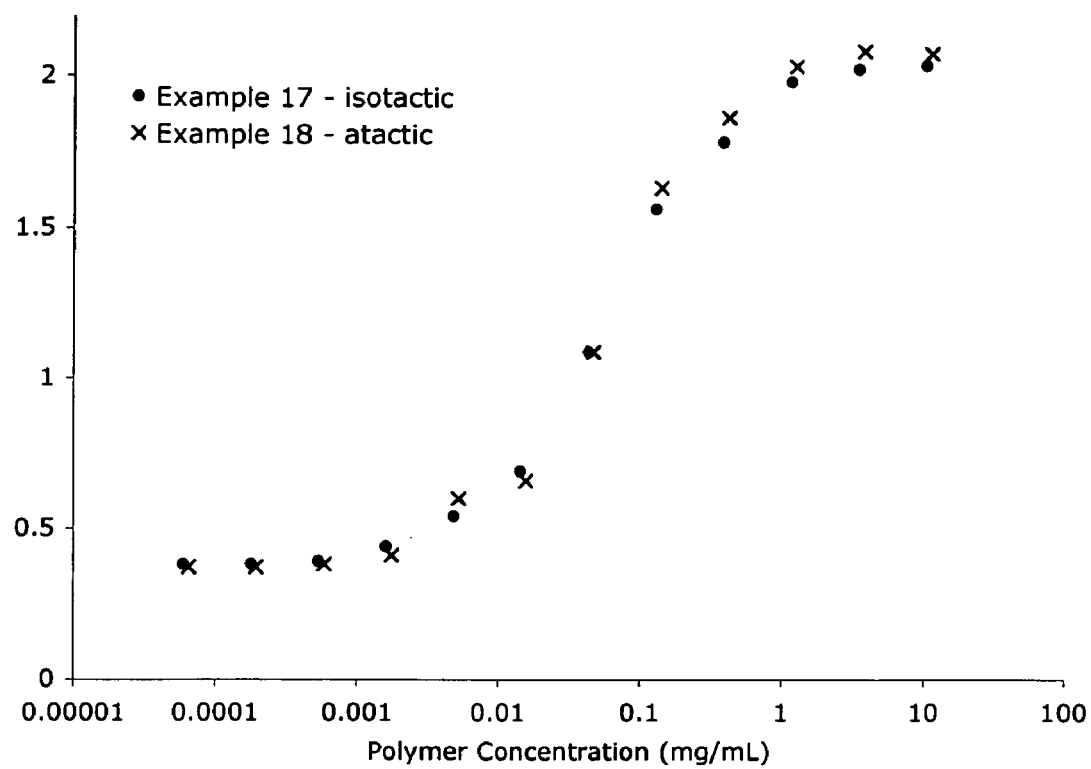
FIG. 7 depicts the CMC curves of $N_3$-PEG12K-b-P(L-Glu(Bzl))$_{30}$)-Ac (Example 17) and $N_3$-PEG12K-b-Poly(L-Glu(Bzl))$_{15}$-co-D-Glu(Bzl))$_{15}$)-Ac (Example 18).
Figure 8:
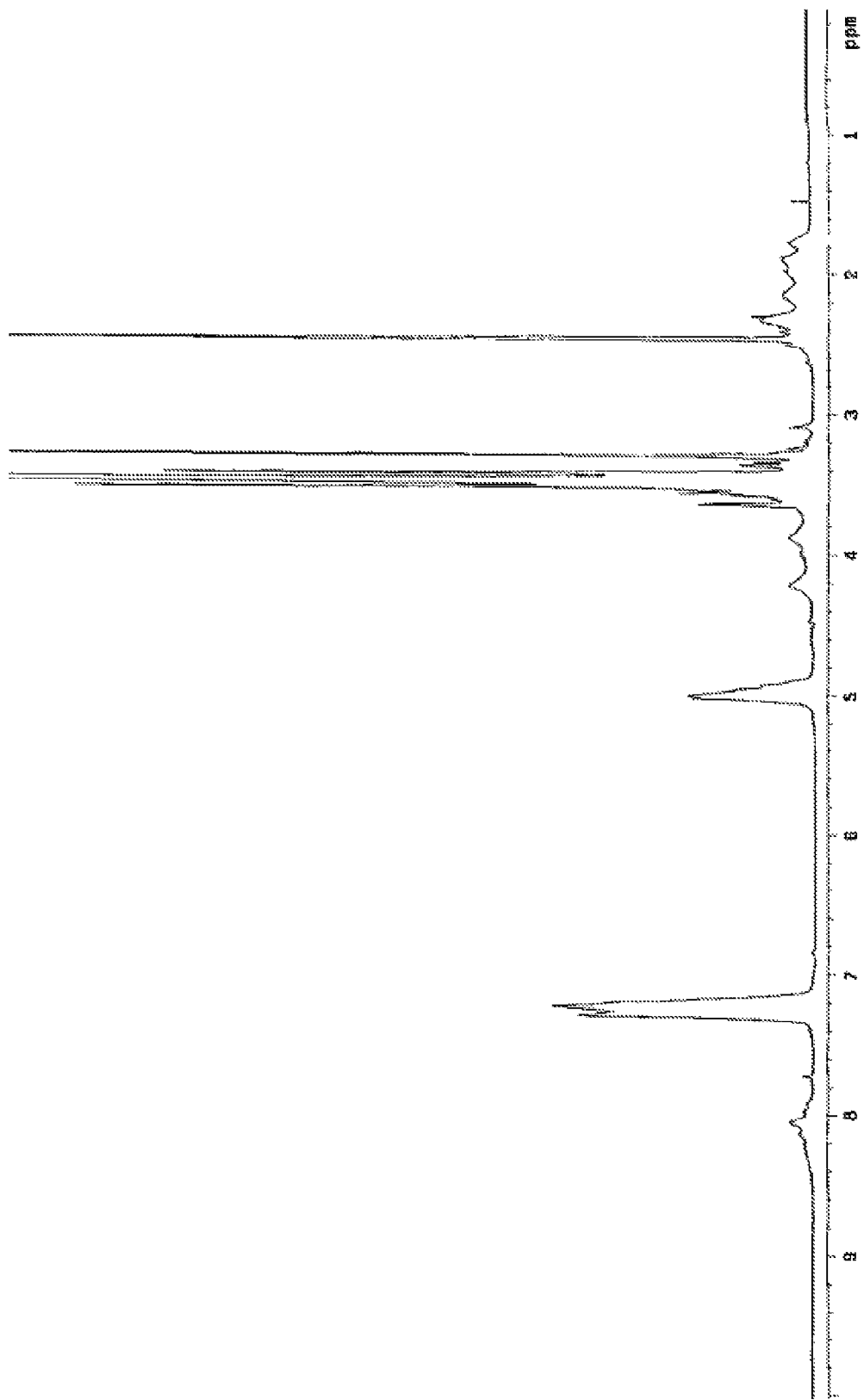
FIG. 8 depicts the solution $^1$H NMR of $N_3$-PEG12K-b-P(L-Glu(Bzl))$_{30}$)-Ac (Example 17) in DMSO-$d_6$.
Figure 9:
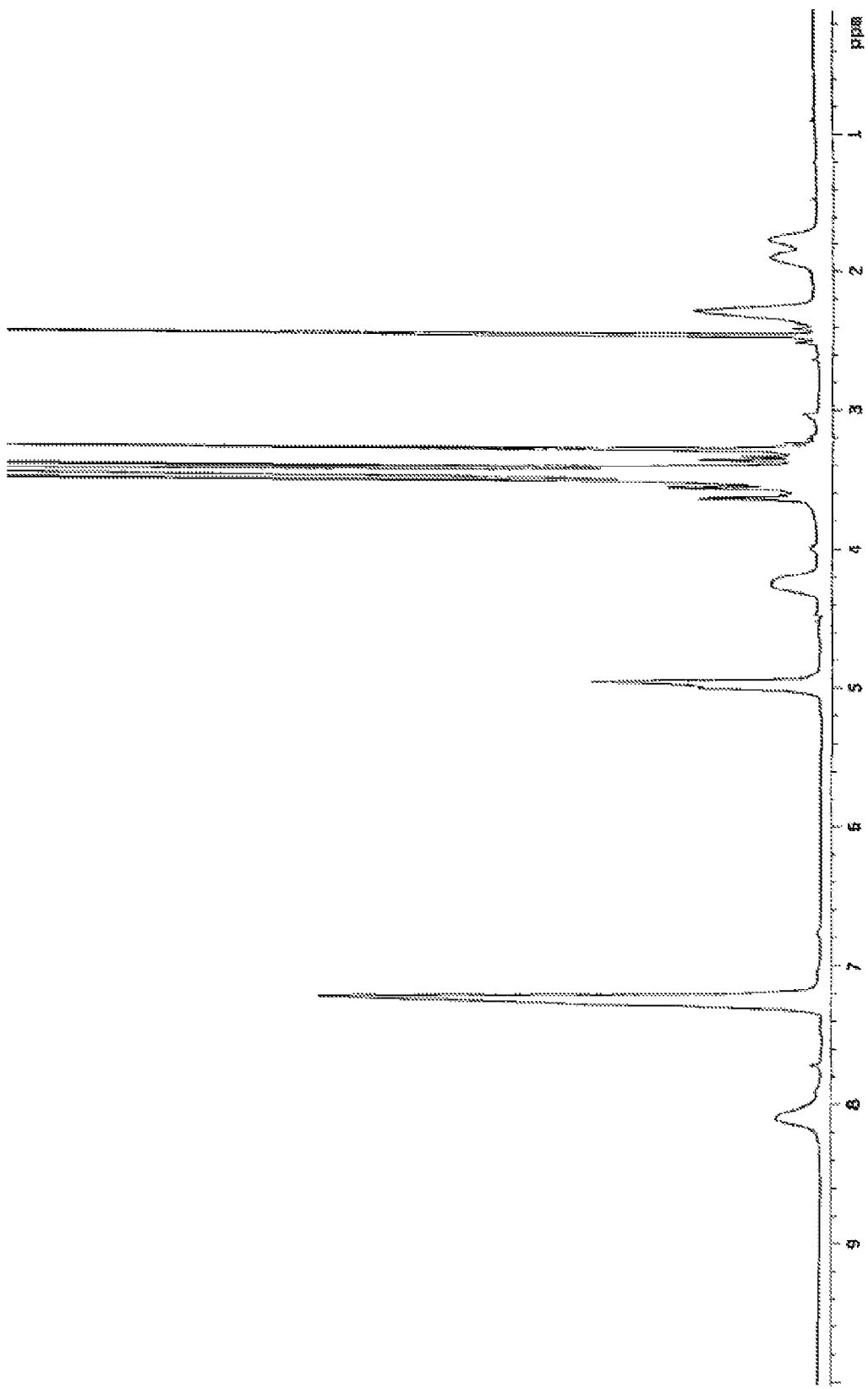
FIG. 9 depicts the solution $^1$H NMR of $N_3$-PEG12K-b-Poly(L-Glu(Bzl))$_{15}$-co-D-Glu(Bzl))$_{15}$)-Ac (Example 18) in DMSO-$d_6$.
Figure 10:
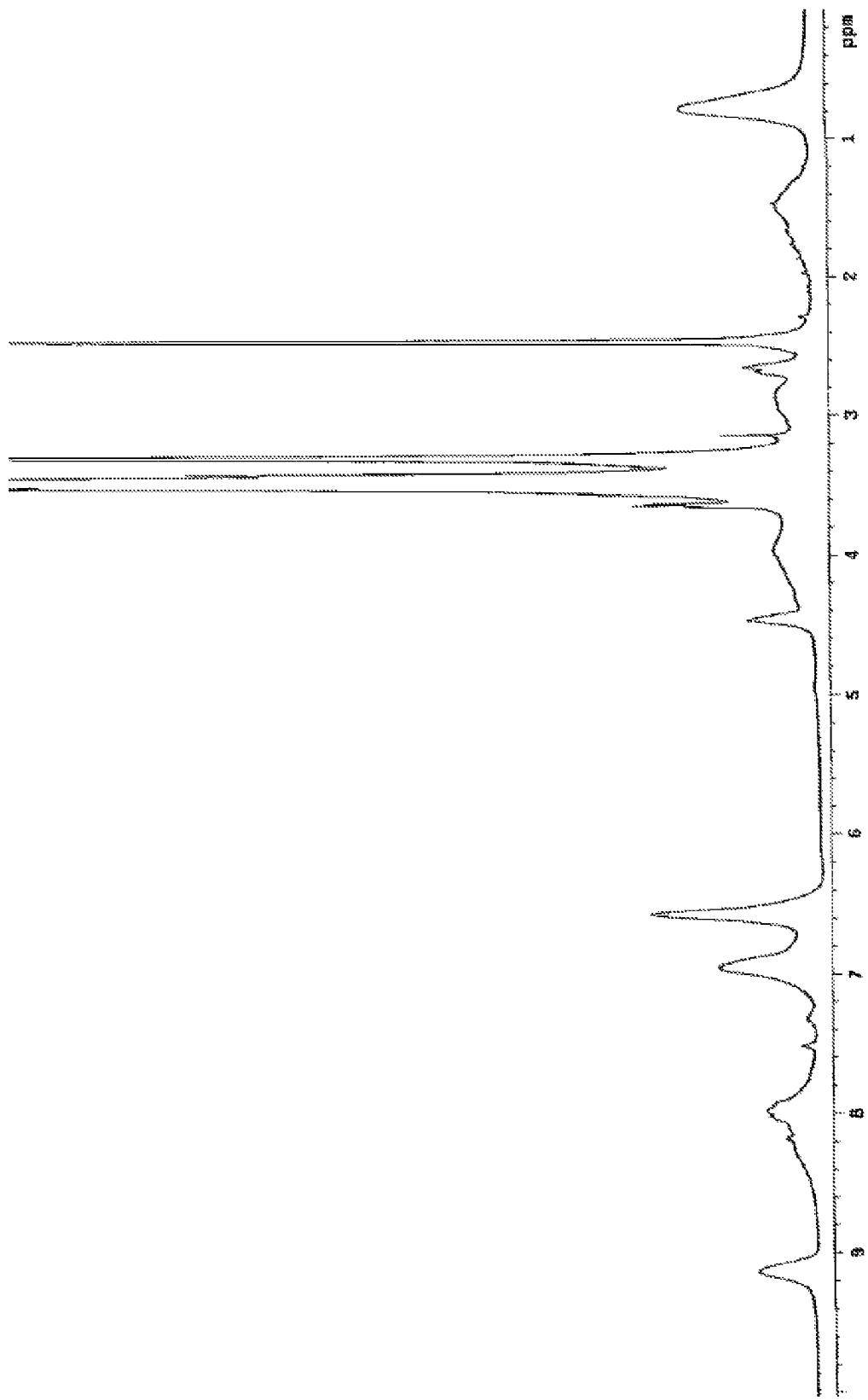
FIG. 10 depicts the solution $^1$H NMR of $N_3$-PEG12K-b-Poly$(Asp)_{10}$-b-Poly(L-Leu$_{13}$-co-L-Tyr$_{17}$)-Ac (Example 21) in DMSO-$d_6$.
Figure 11:
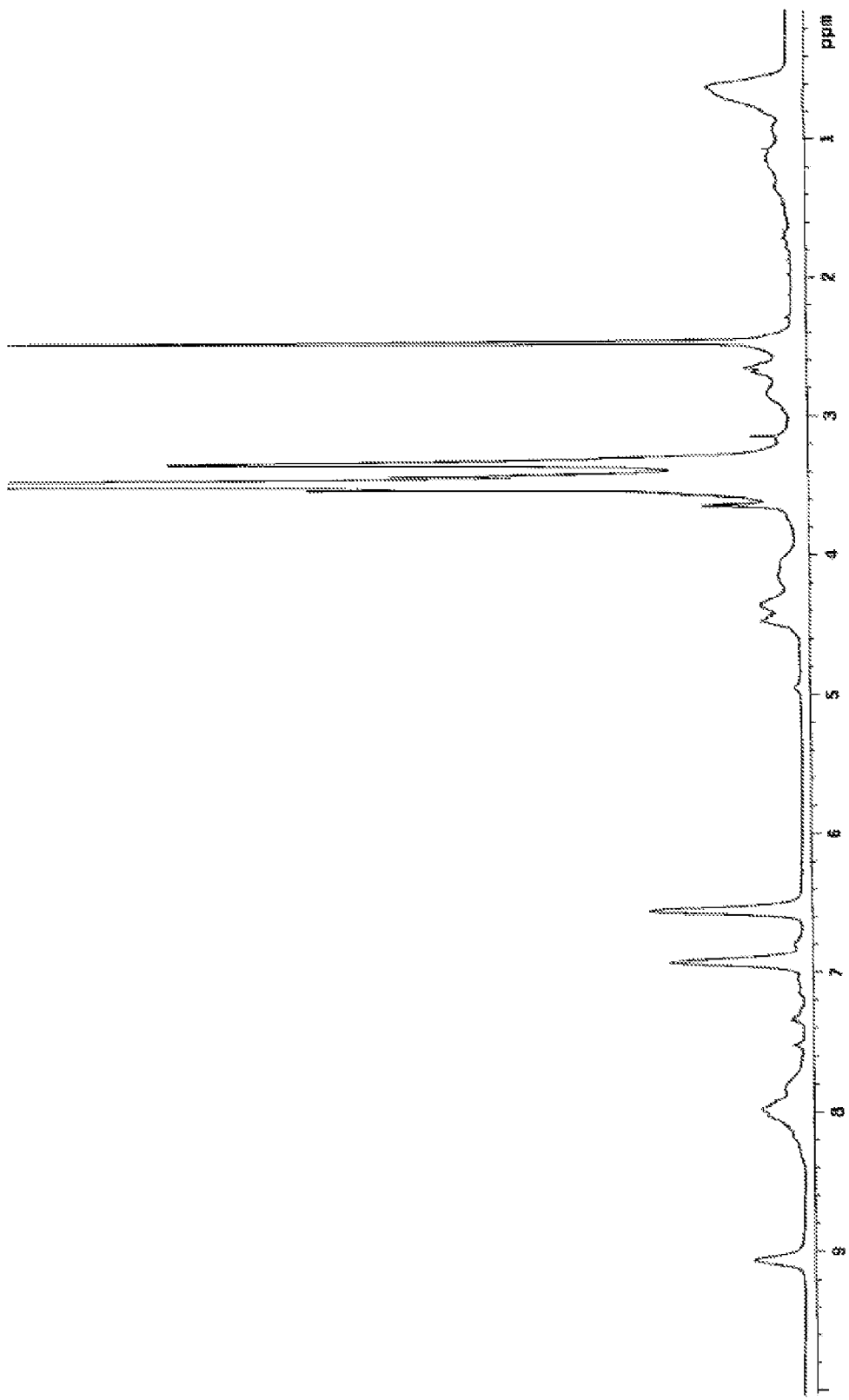
FIG. 11 depicts the solution $^1$H NMR of $N_3$-PEG12K-b-Poly$(Asp)_{10}$-b-Poly(D-Leu$_{13}$-co-L-Tyr$_{17}$)-Ac (Example 22) in DMSO-$d_6$.
Figure 12:
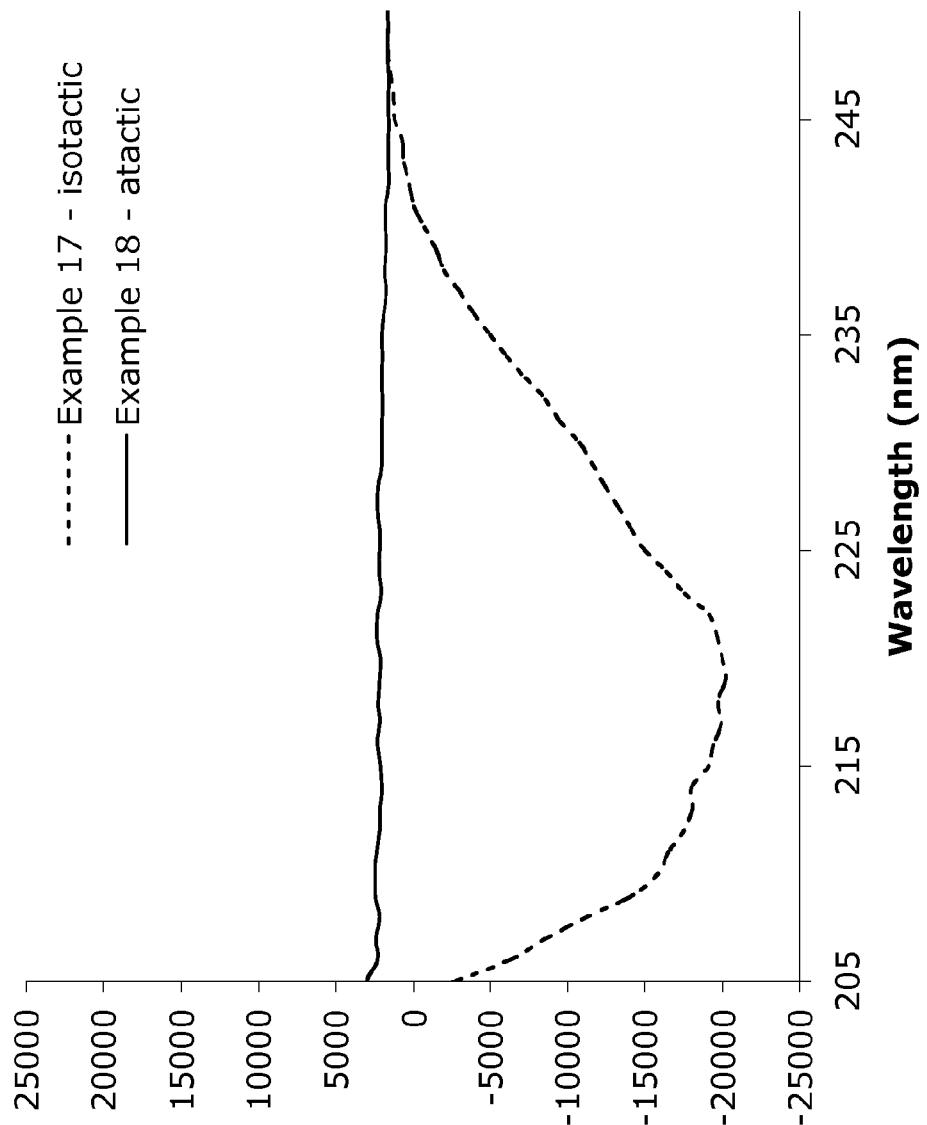
FIG. 12 depicts the circular dichroism spectra of $N_3$-PEG12K-b-P(L-Glu(Bzl))$_{30}$)-Ac (Example 17) and $N_3$-PEG12K-b-Poly(L-Glu(Bzl))$_{15}$-co-D-Glu(Bzl))$_{15}$)-Ac (Example 18).

CMC Determination—The CMC of micelles prepared from block copolymers were determined using the method described by Eisnberg. (Astafieva, I.; Zhong, X. F.; Eisenberg, A. "Critical Micellization Phenomena in Block Copolymer Polyelectrolyte Solutions" *Macromolecules* 1993, 26, 7339-7352.) To perform these experiments, a constant concentration of pyrene ($5\times10^{-7}$ M) was equilibrated with varying concentrations of block copolymer (ca. $2\times10^2$-$1\times10^{-4}$ mg/mL) in phosphate buffered saline at room temperature for 16 hours. Excitation spectra (recorded on a Perkin Elmer LS-55 spectrophotometer with excitation between 328 and 342 nm, emission at 390 nm, 2.5 nm slit width, 15 nm/min scan speed) were recorded for each polymer concentration and the fluorescence intensities recorded at 333 and 338 nm. Eisenberg has shown that the vibrational fine structure of pyrene is highly sensitive to the polarity of its environment. Specifically, the (0,0) excitation band of pyrene will shift from 333 nm in an aqueous environment to 338.5 nm in a hydrophobic environment. The ratio of peak intensities (1338/1333) reveals the hydrophobicity of the environment surrounding the pyrene. Values of 2.0 correspond to a hydrophobic environment such as polystyrene or poly(benzyl glutamate), whereas values of 0.35 correspond to an aqueous environment. Plotting this ratio vs. log of the block copolymer concentration allows for the graphical interpretation of the CMC value. A more quantitative number can be obtained by fitting a logarithmic (y=a ln(x)+b) regression to the data points between the two plateaus (at 2 and 0.35). The CMC can be found by setting y=0.35 and solving for x (concentration in mg/mL). FIG. 6 and FIG. 7 show exemplary CMC curves for polymers found in Example 17, Example 18, Example 21, and Example 22.

CMC of $N_3$-PEG12K-b-Poly(Asp)$_{10}$-b-Poly(L-Leu$_{13}$-co-L-Tyr$_{17}$)-Ac (Example 21)=0.0061 mg/mL=$3.4\times10^{-7}$ M CMC of $N_3$-PEG12K-b-Poly(Asp)$_{10}$-b-Poly(D-Leu$_{13}$-co-L-Tyr$_{17}$)-Ac (Example 22)=0.0207 mg/mL=$1.2\times10^{-6}$ M CMC of $N_3$-PEG12K-b-P(L-Glu(Bzl)$_{30}$)-Ac (Example 17)=0.0054 mg/mL=$2.8\times10^{-7}$ M CMC of $N_3$-PEG12K-b-Poly(L-Glu(Bzl))$_{15}$-co-D-Glu(Bzl)$_{15}$)-Ac (Example 18)=0.0068 mg/mL=$3.6\times10^{-7}$ M In addition to CMC data, information regarding the overall hydrophobicity of the core can be obtained from these pyrene fluorescence experiments. A higher $I_{338}/I_{333}$ ratio corresponds to a more hydrophobic micelle core. This data is represented in Table 12.

Example 31

Core Mobility Determination—The mobility and rigidity of the micelle core was determined using the methods described by Yamamoto (J. Cont. Rel., 2007, 123, 11-18). 1,3-bis(1-pyrenyl)propane(dipyrene) is a fluorescent probe that forms an intramolecular excimer complex when the atmosphere surrounding the molecule is sufficiently mobile. The ratio between the excimer complex emission at 480 nm and the pyrene monomer emission at 398 nm gives information regarding the mobility, where a very low ratio (0.0-0.2) represents a rigid, low mobility core and a higher ratio value (0.4-0.7) represents a flexible, mobile core. Block copolymers were dissolved in phosphate buffered saline at 5 mg/mL and equilibrated with $5.5\times10^{-6}$ M dipyrene for 16 hours. The fluorescence emission spectra (recorded on a Perkin Elmer LS-55 spectrophotometer with emission between 360 and 500 nm, excitation at 333 nm, 5 nm slit width, 120 nm/min scan speed) were recorded for each sample and the peak intensities at 398 and 480 nm were recorded. The mobility can be inferred from the $I_{480}/I_{398}$ ratio as described above, and is recorded in Table 12.

Example 32

Diameters of polymer micelles were determined by dynamic light scattering. Lyopholyzed polymers were dissolved at 5 mg/mL in phosphate buffered saline at pH 7.4 and equilibrated overnight. Each sample was analyzed in a PSS NICOMP 380 with a 690 nm laser at a 90 degree angle. DLS sizing data was recorded from the volume weighted Gaussian distribution. Results are summarized in Table 12.

TABLE 12

| Polymer | CMC (ug/mL) | Hydrophobicity Value (I338/I333) | Mobility (I480/I398) | Micelle Diameter (nm) |
|---|---|---|---|---|
| Example 17-isotactic | 5.4 | 2.02 | 0.23 | 87.3 |
| Example 18-atactic | 6.8 | 2.08 | 0.61 | 42.7 |
| Example 21-isotactic | 6.1 | 1.83 | 0.33 | 40.1 |
| Example 22-atactic | 20.7 | 1.82 | 0.51 | 19.2 |

The results summarized in Table 12 show a marked difference in the physical properties of the micelles formed by isotactic polymers of all L stereochemistry vs. atactic polymers of mixed stereochemistry. As expected, the overall hydrophobicity of the core is similar for both stereoisomers since the chemical composition remains unchanged. However, there are significant differences in the CMC values for the triblock copolymers, as well as differences in both the mobility and in the micelle diameter for both sets of polymers. It is believed that the random stereochemistry leads to a random coil conformation, allowing for greater degrees of freedom, thus increasing the mobility of the core.

Example 33

Solution $^1$H NMR analysis of these polymers was performed on a Varian VNMRS 400 MHz NMR. Samples were prepared at 40 mg/mL in DMSO-$d_6$. Example spectra are shown in FIGS. 8-11. A difference in polymer solution conformation can be observed between the isotactic and atactic polymers, as the all L configured isotactic polymers have broad peak shapes, while the atactic polymers have well defined resonances, again indicating a random coil conformation in the atactic polymer.

Example 34

Figure 13:
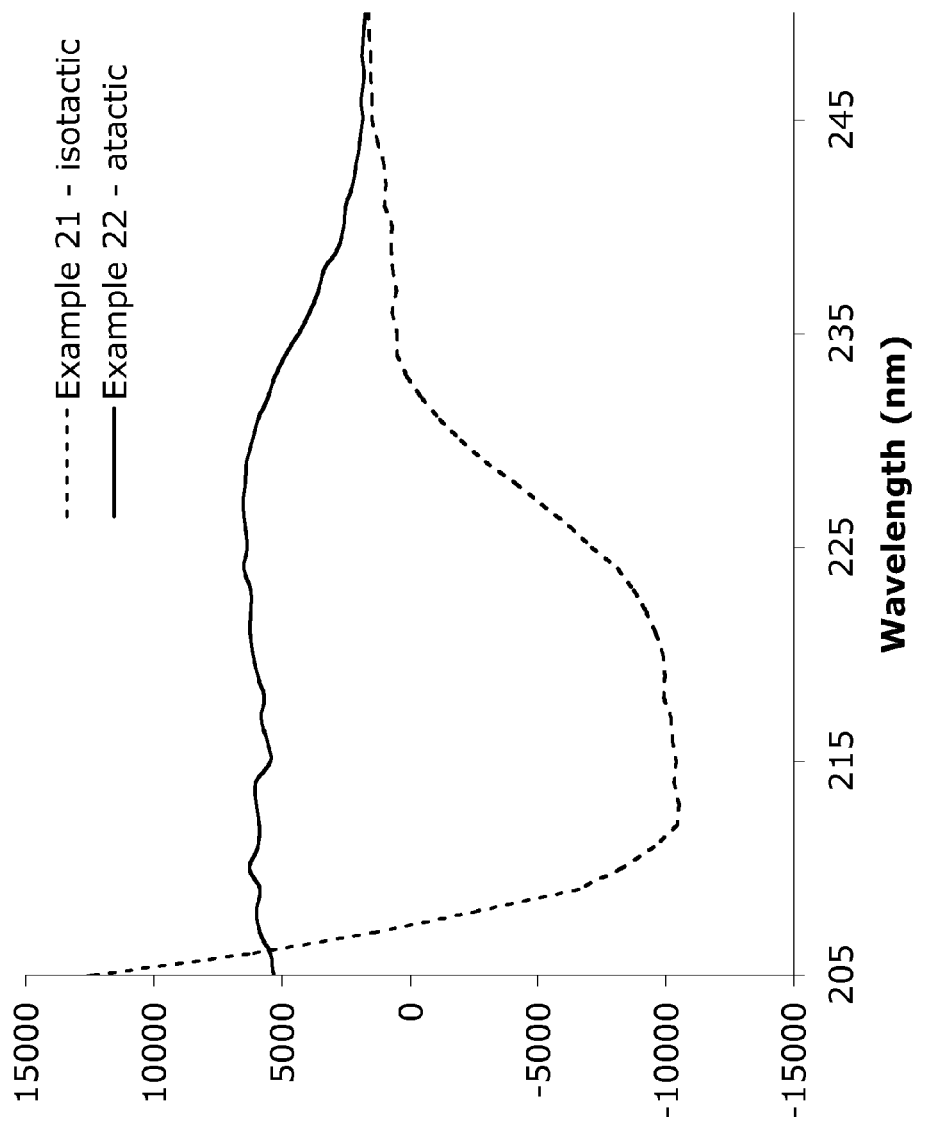
FIG. 13 depicts the circular dichroism spectra of $N_3$-PEG12K-b-Poly$(Asp)_{10}$-b-Poly(L-Leu$_{13}$-co-L-Tyr$_{17}$)-Ac (Example 21) and $N_3$-PEG12K-b-Poly$(Asp)_{10}$-b-Poly(D-Leu$_{13}$-co-L-Tyr$_{17}$)-Ac (Example 22).

Circular Dichroism (CD) Spectroscopy—Block copolymers were dissolved in phosphate buffered saline at 0.1 mg/mL. CD/UV spectra were recorded on a AVIV 215 spectrophotometer. ΔA (millidegrees) was recorded in a 1 cm cuvette at 25° C. from 200-250 nm, and the data was averaged over three scans, then subtracted from the average of three blank samples. ΔA was converted to molar elipticity using the AVIV software and the number of amino acid residues per polymer chain. Data is plotted in FIG. 13 and FIG. 14. It was found that the isotactic polymers found in Example 17 and Example 21 exhibited CD spectra consistent with a helical secondary structure, while the actactic, mixed stereochemistry polymers of Example 18 and Example 22 exhibited little to no CD response, consistent with disruption of any secondary structure.

Example 35

Drug Loading Efficiency—The drug loading efficiency of Example 17, Example 18, Example 21, and Example 22 were evaluated for docetaxel, irinotecan, and SN-38. Target loadings of 10 wt % were attempted for docetaxel, 15 wt % for irinotecan, and 2 wt % for SN-38. The drugs were encapsulated with the following general procedure:

A solution consisting of the desired active (e.g. 10 mg docetaxel, 15 mg irinotecan, or 2 mg SN-38) and the desired polymer (ca. 100 mg) in CHCl$_3$ was added drop-wise to a vortexing flask containing water (20 mL). The mixture was vortexed until a homogenous solution was formed, or until the organic phase had completely evaporated. This solution was filtered through a 0.22 μm filter, then lyophilized and the dry powder stored at 4° C.

Actual drug loading was determined by HPLC with the following methods:

Docetaxel loading was determined by weighing ca. 10-20 mg of drug loaded micelle into a 10 mL volumetric flask and filling to volume with 0.5% acetic acid in methanol. 10 μL of this solution was injected onto a Waters 2695 HPLC with a 996 photodiode array detector and ES Industries Chromegabond Alkyl-Phenyl column (300 mm) eluting with 35% acetonitrile in water at 1 mL/min. Docetaxel eluted at 20.5 minutes under these conditions. Quantitation was performed from a calibration curve constructed from known concentrations of docetaxel standard injections from chromatograms extracted at 227 nm. Area under the curve (AUC) can be converted to concentration with the following equation:

$$\frac{\mu g}{10 \; \mu L} = \frac{AUC}{1100928} = \frac{mg}{10 \; mL}$$

Irinotecan loading was determined by weighing ca. 10-20 mg of drug loaded micelle into a 10 mL volumetric flask and filling to volume with 5 mL of 100 mM sodium acetate buffer at pH 3.1 and 5 mL acetonitrile. 10 μL of this solution was injected onto a Waters 2695 HPLC with a 996 photodiode array detector and ES Industries Chromegabond Alkyl-Phenyl column (300 mm) eluting with 40% 100 mM sodium acetate buffer (pH 3.1) and 60% acetonitrile at 1 mL/min. Irinotecan eluted at 6.5 minutes under these conditions. Quantitation was performed from a calibration curve constructed from known concentrations of irinotecan standard injections from chromatograms extracted at 227 nm. Area under the curve (AUC) can be converted to concentration with the following equation:

$$\frac{\mu g}{10 \; \mu L} = \frac{AUC}{3110806} = \frac{mg}{10 \; mL}$$

SN-38 loading was determined by weighing ca. 10-20 mg of drug loaded micelle into a 10 mL volumetric flask and filling to volume with 2 mL of DMSO and 8 mL of acetonitrile. 10 μL of this solution was injected onto a Waters 2695 HPLC with a 996 photodiode array detector and ES Industries Chromegabond Alkyl-Phenyl column (300 mm) eluting with 50% 25 mM monobasic sodium phosphate buffer (pH 3.1) and 50% acetonitrile at 1 mL/min. SN-38 eluted at 4.0 minutes under these conditions. Quantitation was performed from a calibration curve constructed from known concentrations of SN-38 standard injections from chromatograms extracted at 265 nm. Area under the curve (AUC) can be converted to concentration with the following equation:

$$\frac{\mu g}{10 \; \mu L} = \frac{AUC}{3936855} = \frac{mg}{10 \; mL}$$

Drug loadings and drug loading efficiencies are reported in Table 13.

TABLE 13

| Polymer | Feed % | Final % | % Efficiency |
| --- | --- | --- | --- |
| Docetaxel | | | |
| Example 17-isotactic | 9.2 | 8.4 | 91.8 |
| Example 18-atactic | 9.2 | 8.5 | 92.2 |
| Example 21-isotactic | 8.8 | 7.9 | 89.5 |
| Example 22-atactic | 8.9 | 8.3 | 94.0 |
| Irinotecan | | | |
| Example 17-isotactic | 13.1 | 1.6 | 12.2 |
| Example 18-atactic | 13.5 | 13.2 | 97.8 |
| Example 21-isotactic | 13.1 | 8.0 | 61.1 |
| Example 22-atactic | 12.9 | 12.6 | 97.7 |
| SN-38 | | | |
| Example 17-isotactic | 2.3 | 0.02 | 0.7 |
| Example 18-atactic | 2.1 | 0.02 | 0.8 |
| Example 21-isotactic | 2.5 | 0.03 | 1.2 |
| Example 22-atactic | 2.0 | 0.03 | 1.2 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A triblock copolymer of the following structure:

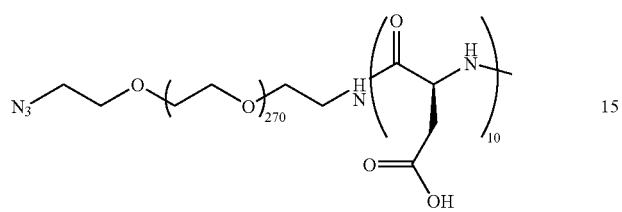

-continued

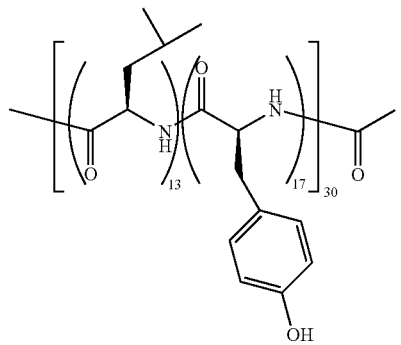

* * * * *